US007851672B2

(12) United States Patent
Davies et al.

(10) Patent No.: US 7,851,672 B2

(45) Date of Patent: Dec. 14, 2010

(54) GENERATION OF PLANTS WITH ALTERED OIL, PROTEIN, OR FIBER CONTENT

(75) Inventors: John P. Davies, Portland, OR (US); Hein Tsoeng (Medard) Ng, Charlottesville, VA (US)

(73) Assignee: Agrinomics LLC, Portland, OR (US)

( * ) Notice: Subject to any disclaimer, the term of this patent is extended or adjusted under 35 U.S.C. 154(b) by 227 days.

(21) Appl. No.: 11/956,196

(22) Filed: Dec. 13, 2007

(65) Prior Publication Data

US 2008/0160158 A1 Jul. 3, 2008

Related U.S. Application Data

(60) Provisional application No. 60/870,345, filed on Dec. 15, 2006.

(51) Int. Cl.

| | |
|---|---|
| ***A01H 1/06*** | (2006.01) |
| ***C12N 15/01*** | (2006.01) |
| ***C07H 21/04*** | (2006.01) |

(52) U.S. Cl. ........................ 800/281; 800/278; 800/295; 800/298; 435/6; 435/441; 536/24.3; 536/23.6

(58) Field of Classification Search ........................ None
See application file for complete search history.

(56) References Cited

U.S. PATENT DOCUMENTS

| | | | | |
|---|---|---|---|---|
| 5,322,783 | A | 6/1994 | Tomes et al. | |
| 5,538,880 | A | 7/1996 | Lundquist et al. | |
| 5,550,318 | A | 8/1996 | Adams et al. | |
| 5,563,055 | A | 10/1996 | Townsend et al. | |
| 5,610,042 | A | 3/1997 | Chang et al. | |
| 5,639,790 | A | 6/1997 | Voelker et al. | |
| 5,704,160 | A | 1/1998 | Bergquist et al. | |
| 5,952,544 | A | 9/1999 | Browse et al. | |
| 6,229,033 | B1 | 5/2001 | Knowlton | |
| 6,248,939 | B1 | 6/2001 | Leto et al. | |
| 7,528,295 | B2 * | 5/2009 | Lightner et al. | 800/298 |
| 2004/0025202 | A1 | 2/2004 | Laurie et al. | |
| 2006/0143729 | A1 | 6/2006 | Alexandrov et al. | |
| 2006/0150283 | A1 * | 7/2006 | Alexandrov et al. | 800/288 |
| 2006/0277630 | A1 | 12/2006 | Lightner et al. | |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | WO 02/072775 | 9/2002 |
| WO | WO 2004/092367 | 10/2004 |
| WO | 2004/093528 | 11/2004 |
| WO | 2004/093532 | 11/2004 |
| WO | 2005/107437 | 11/2005 |
| WO | WO 2006/007432 | 1/2006 |
| WO | 2007/053482 | 5/2007 |

OTHER PUBLICATIONS

Comai et al., "Efficient discovery of DNA polymorphisms in natural populations by Ecotilling," *The Plant Journal*, 37:778-786 (2004).

Zou et al., "Modification of Seed Oil Content and Acyl Composition in the Brassicaceae by Expression of a Yeast *sn*-2 Acyltransferase Gene," *The Plant Cell*, 9:909-923 (1997).

Anoop et al., "Modulation of citrate metabolism alters aluminum tolerance in yeast and transgenic canola overexpressing a mitochondrial citrate synthase," *Plant Physiol.* 132, 2205-2217 (2003).

Bateman et al., "Pfam 3.1: 1313 multiple alignments and profile HMMs match the majority of proteins," *Nucleic Acids Res.*, 27:260-262, 1999.

Beisson, et al., "*Arabidopsis* genes involved in acyl lipid metabolism. A 2003 census of the candidates, a study of the distribution of expressed sequence tags in organs, and a web-based database," *Plant Physiol.*, 132:681-697 (2003).

Bert et al., "Comparative genetic analysis of quantitative traits in sunflower (*Helianthus annuus L.*). 2. Characterisation of QTL involved in developmental and agronomic traits," *Theor. Appl. Genet.*, 107:181-9, (2003).

Browse et al., "Fluxes through the prokaryotic and eukaryotic pathways of lipid synthesis in the '16:3' plant *Arabidopsis thaliana,*" *Biochem J.* 235:25-31 (1986).

Chapple and Carpita, "Plant cell walls as targets for biotechnology," *Current Opinion in Plant Biology*, 1:179-185 (1998).

Christensen et al., *9th International Conference on Arabidopsis Research*, Univ. of Wisconsin-Madison, Jun. 24-28, Abstract 165 (1998).

Christou et al., "Inheritance and expression of foreign genes in transgenic soybean plants," *Proc. Natl. Acad. Sci. USA*, 86:7500-7504 (1989).

Colbert et al., "High-throughput screening for induced point mutations," *Plant Physiol.* 126:480-484 (2001).

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).

Dehesh et al., "Overexpression of 3-ketoacyl-acyl-carrier protein synthase IIIs in plants reduces the rate of lipid synthesis," *Plant Physiol.*, 125:1103-1114 (2001).

Douglas et al., "Nutritional evaluation of low phytate and high protein corns," *Poultry Sci.* 79:1586-1591 (2000).

Eastmond et al., "Re-examining the role of the glyoxylate cycle in oilseeds," *Trends Plant Sci.*, 6:72-78 (2001).

(Continued)

*Primary Examiner*—Eileen B O Hara
(74) *Attorney, Agent, or Firm*—Klarquist Sparkman, LLP.

(57) ABSTRACT

The present invention is directed to plants that display an improved oil quantity phenotype or an improved meal quality phenotype due to altered expression of an HIO nucleic acid. The invention is further directed to methods of generating plants with an improved oil quantity phenotype or improved meal quality phenotype.

6 Claims, No Drawings

OTHER PUBLICATIONS

Eccleston et al., "Expression of lauroyl-acyl carrier protein thioesterase in *brassica napus* seeds induces pathways for both fatty acid oxidation and biosynthesis and implies a set point for triacylglycerol accumulation," *Plant Cell.* 10:613-622 (1998).

Edwards et al., "Protein and energy evaluation of soybean meals processed from genetically modified high-protein soybeans," *Poultry Sci*. 79:525-527 (1999).

Everett et al., "Genetic engineering of sunflower (*Helianthus annuus L.*)," *Bio/Technology*, 5:1201 (1987).

Falco et al., "Transgenic canola and soybean seeds with increased lysine," *Bio/Technology*, 13:577-582 (1995).

Fatland et al., "Molecular biology of cytosolic acetyl-CoA generation," *Biochem Soc Trans*., 28:593-595 (2000).

Fatland et al., "Reverse genetic characterization of cytosolic acetyl-CoA generation by ATP-citrate lyase in *Arabidopsis," Plant Cell*., 17:182-203 (2004).

Feldmann et al., "A Dwarf Mutant of *Arabidopsis* Generated by T-DNA Insertion Mutagenesis," *Science*, 243:1351-1354 (1989).

Focks et al., "wrinkled1: A novel, low-seed-oil mutant of *Arabidopsis* with a deficiency in the seed-specific regulation of carbohydrate metabolism," *Plant Physiol*., 118:91-101 (1998).

Fridborg et al., "The *Arabidopsis* dwarf mutant *shi* exhibits reduced gibberellin responses conferred by overexpression of a new putative zinc finger protein," *Plant Cell*, 11:1019-1032 (1999).

Girke et al., "Microarray analysis of developing *Arabidopsis* seeds," *Plant Physiol*. 124:1570-1581 (2000).

Hayashi et al., "Activation of a plant gene by T-DNA tagging: auxin-independent growth in vitro," *Science*, 258:1350-1353 (1992).

Honig and Rackis, "Determination of the total pepsin-pancreatin indigestible content (dietary fiber) of soybean products, wheat bran, and corn bran," *J. Agri. Food Chem*., 27:1262-1266 (1979).

Jako et al., "Seed-specific over-expression of an *Arabidopsis* cDNA encoding a diacylglycerol acyltransferase enhances seed oil content and seed weight," *Plant Physiol*., 126(2):861-74 (2001).

James and Dooner, "Isolation of EMS-induced mutants in *Arabidopsis* altered in seed fatty acid composition," *Theor. Appl. Genet*., 80:241-245 (1990).

Kardailsky et al., "Activation tagging of the floral inducer FT," *Science*, 286:1962-1965 (1999).

Katavic et al., "Alteration of seed fatty acid composition by an ethyl methanesulfonate-induced mutation in *Arabidopsis thaliana* affecting diacylglycerol acyltransferase activity," *Plant Physiol*., 108:399-409 (1995).

Katavic et al., "Utility of the *Arabidopsis* FAE1 and yeast SLC1-1 genes for improvements in erucic acid and oil content in rapeseed," *Biochem Soc Trans*., 28:935-937 (2000).

Kline et al., "High velocity microprojectiles for delivering nucleic acids into living cells," *Nature*, 327:70-73 (1987).

Larson et al., "Acyl CoA profiles of transgenic plants that accumulate medium-chain fatty acids indicate inefficient storage lipid synthesis in developing oilseeds," *Plant J*., 32:519-527 (2002).

Lemieux et al., "Mutants of *Arabidopsis* with alterations in seed lipid fatty acid composition," *Theor. Appl. Genet*., 80:234-240 (1990).

Lin et al., "The Pex16p homolog SSE1 and storage organelle formation in *Arabidopsis* seeds," *Science*, 284:328-330 (1999).

Lionneton et al., "Development of an AFLP-based linkage map and localization of QTLs for seed fatty acid content in condiment mustard (*Brassica juncea*)," *Genome*, 45:1203-15 (2002).

Liu et al., "A transcriptional switch in the expression of yeast tricarboxylic acid cycle genes in response to a reduction or loss of respiratory function," *Mol Cell Biol*., 19:6720-6728 (1999).

McCallum et al., "Targeted screening for induced mutations," *Nature Biotechnology*, 18:455-457 (2000).

Mekhedov et al., "Toward a functional catalog of the plant genome. A survey of genes for lipid biosynthesis," *Plant Physiol*., 122:389-402 (2000).

Moire et al., "Impact of unusual fatty acid synthesis on futile cycling through beta-oxidation and on gene expression in transgenic plants," *Plant Physiol*., 134:432-442 (2004).

Moore et al., "Chromatography of Amino Acids on Sulfonated Polystyrene Resins," *Anal. Chem*., 30:1185-1190 (1958).

Mulder et al., "The InterPro Database, 2003 brings increased coverage and new features," *Nucleic Acids Res*., 31:315-318, 2003.

Neuhaus et al., "Nonphotosynthetic Metabolism in Plastids," *Annu Rev Plant Physiol Plant Mol Biol*., 51:111-140 (2000).

O'Hara et al., "Fatty acid and lipid biosynthetic genes are expressed at constant molar ratios but different absolute levels during embryogenesis," *Plant Physiol*., 129:310-320 (2002).

Okuley et al., "*Arabidopsis FAD2* gene encodes the enzyme that is essential for polyunsaturated lipid synthesis," *Plant Cell*, 6:147-158 (1994).

Parsons et al., "Nutritional evaluation of soybean meals varying in oligosaccharide content," *Poultry Sci*., 79:1127-1131 (2000).

Pritchard et al., "Germination and storage reserve mobilization are regulated independently in *Arabidopsis," Plant J*., 31:639-647 (2002).

Rangasamy et al., "Genetic enhancement of fatty acid synthesis by targeting rat liver ATP:citrate lyase into plastids of tobacco," *Plant Physiol*., 122:1231-1238 (2000).

Rangasamy et al., "Compartmentation of ATP:citrate lyase in plants," *Plant Physiol*. 122:1225-1230 (2000).

Ratledge et al., "Correlation of ATP/citrate lyase activity with lipid accumulation in developing seeds of *Brassica napus L. Lipids*," 32:7-12 (1997).

Rawsthorne, "Carbon flux and fatty acid synthesis in plants," *Prog Lipid Res*. 41:182-196 (2002).

Ruuska et al., "Contrapuntal networks of gene expression during *Arabidopsis* seed filling," *Plant Cell*., 14:1191-1206 (2002).

Rylott et al., "Co-ordinate regulation of genes involved in storage lipid mobilization in *Arabidopsis thaliana," Biochem Soc Trans*., 29:283-287 (2001).

Schaffer et al., "The late elongated hypocotyl mutation of *Arabidopsis* disrupts circadian rhythms and the photoperiodic control of flowering," *Cell*, 93:1219-1229 (1998).

Schnarrenberger et al., "Evolution of the enzymes of the citric acid cycle and the glyoxylate cycle of higher plants. A case study of endosymbiotic gene transfer," *Eur J Biochem*., 269:868-883 (2002).

Schnurr et al., "Characterization of an acyl-CoA synthetase from *Arabidopsis thaliana," Biochem Soc Trans*., 28:957-958 (2000).

Shewry, "Seed storage proteins: structures and biosynthesis," *Plant Cell*, 7:945-956 (1995).

Shockey et al., "Characterization of the AMP-binding protein gene family in *Arabidopsis thaliana*: will the real acyl-CoA synthetases please stand up?" *Biochem Soc Trans*., 28:955-957 (2000).

Thelen et al., "Biotin carboxyl carrier protein isoforms in Brassicaceae oilseeds," *Biochem Soc Trans*., 28:595-598 (2000).

Weigel et al., "Activation tagging in *Arabidopsis," Plant Physiology*, 122:1003-1013 (2000).

White et al., "A new set of *Arabidopsis* expressed sequence tags from developing seeds. The metabolic pathway from carbohydrates to seed oil," *Plant Physiol*., 124:1582-1594 (2000).

Wilson et al., "A Dissociation insertion causes a semidominant mutation that increases expression of TINY, an *Arabidopsis* gene related to APETALA2," *Plant Cell*, 8:659-671 (1996).

Yadav et al., "Cloning of higher plant omega-3 fatty acid desaturases," *Plant Physiol*., 103:467-476 (1993).

Database EMBL, Accession No. AC012190, Apr. 14, 2005, 23 page.

Database EMBL, Accession No. Q9LPV0, Oct. 1, 2000, 2 pages.

Zhao et al., "Conditional QTL mapping of oil content in rapeseed with respect to protein content and traits related to plant development and grain yield," *Theoretical and Applied Genetics*, 113(1): 33-38 (2006).

Zhao et al., "Oil content in a European x Chinese rapeseed population: QTL with additive and epistatic effects and their genotype-environment interactions," *Crop Science*, 45(1): 51-59 (2005).

* cited by examiner

GENERATION OF PLANTS WITH ALTERED OIL, PROTEIN, OR FIBER CONTENT

CROSS REFERENCE TO RELATED APPLICATION(S)

This application claims the benefit of U.S. Provisional Application No. 60/870,345, filed Dec. 15, 2006, the entirety of which is incorporated herein by reference.

FIELD OF THE DISCLOSURE

The present disclosure is related to modified plants with altered oil, protein, and/or fiber content, as well as methods of making modified plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has not been able to achieve seed oil content above 9%. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80: 234-240; James and Dooner, 1990, *Theor. Appl. Genet.* 80: 241-245). T-DNA mutagenesis screens (Feldmann et al., 1989, *Science* 243: 1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol.* 103: 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology,* 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, 9th *International Conference on Arabidopsis Research,* Univ. of Wisconsin-Madison, June 24-28, Abstract 165).

SUMMARY

Provided herein are modified plants having an altered phenotype. Modified plants with an altered phenotype may include an improved oil quantity and/or an improved meal quality phenotype. The altered phenotype in a modified plant may also include altered oil, protein, and/or fiber content in any part of the modified plant, for example in the seeds. In some embodiments of a modified plant, the altered phenotype is an increase in the oil content of the seed (a high oil phenotype). In other embodiments, the altered phenotype may be an increase in protein content in the seed and/or a decrease in the fiber content of the seed. Also provided is seed meal derived from the seeds of modified plants, wherein the seeds have altered protein content and/or altered fiber content. Further provided is oil derived from the seeds of modified plants, wherein the seeds have altered oil content. Any of these changes can lead to an increase in the AME from the seed or seed meal from modified plants, relative to control or wild-type plants. Also provided herein is meal, feed, or food produced from any part of the modified plant with an altered phenotype.

In certain embodiments, the disclosed modified plants include transgenic plants having a transformation vector comprising a HIO nucleotide sequence (or HIO gene alias) that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Examples of the disclosed transgenic plant are produced by a method that comprises introducing into progenitor cells of the plant a plant transformation vector comprising a HIO nucleotide sequence that encodes, or is complementary to a sequence that encodes, a HIO polypeptide, and growing the transformed progenitor cells to produce a transgenic plant, wherein the HIO polynucleotide sequence is expressed, causing an altered phenotype in the transgenic plant. In some specific, non-limiting examples, the method produces transgenic plants wherein expression of the HIO polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen, radiation, or ultraviolet light. In some embodiments of the method, the plant is bred to generate progeny which inherit the allele and express the altered phenotype. In particular embodiments of the method, the method employs candidate gene/QTL methodology or TILLING methodology.

Also provided herein is a modified plant cell having an altered phenotype. In some embodiments, the modified plant cell includes a transformation vector comprising a HIO nucleotide sequence that encodes or is complementary to a sequence that encodes a HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "altered phenotype" refers to plants, or any part of a plant (for example, seeds, or meal produced from seeds), with an altered oil, protein, and/or fiber content (phenotype). As provided herein, altered oil, protein (for example, digestible protein) and/or fiber content includes either an increased or decreased level of oil, protein (for example, digestible protein) and/or fiber content in plants, seeds or seed meal. Any combination of these changes can lead to an altered phenotype. For example, in one specific non-limiting example, an altered phenotype can refer to increased oil and decreased fiber content. In another specific non-limiting example, an altered phenotype can refer to unchanged protein and decreased fiber content. In another specific non-limiting example, an altered phenotype can refer to increased oil and protein and decreased fiber. In yet other non-limiting examples, an altered phenotype can refer either to increased oil and protein and unchanged fiber content; unchanged oil, increased protein, and decreased fiber content; or increased oil, increased protein, and decreased fiber content. It is also provided that any combination of these changes can lead to an increase in the AME (available metabolizable energy) from the seed or meal generated from the seed. An altered phenotype also includes an improved seed quality (ISQ) phenotype or an improved seed meal quality phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a modified plant with an increase in AME includes modified plants with altered seed oil, digestible protein, total protein and/or fiber content, resulting in an increase in the value of animal feed derived from the seed.

As used herein, the term "content" refers to the type and relative amount of, for instance, a seed or seed meal component.

As used herein, the term "seed oil" refers to the total amount of oil within the seed.

As used herein, the term "seed fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "seed total protein" refers to the total amount of protein within the seed.

As used herein, the term "seed digestible protein" refers to the seed protein that is able to be digested by enzymes in the digestive track of an animal. It is a subset of the total protein content.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog or paralog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-modified or wild-type plant. "Under-expression" refers to decreased expression of a polynucleotide and/or polypeptide sequence, generally of an endogenous gene, relative to its expression in a wild-type plant. The terms "mis-expression"

and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type or native plant is also a control plant. In another embodiment, a wild-type or native plant is a non-transgenic or non-mutated plant. In yet another embodiment, a wild-type or native plant is a non-modified plant.

As used herein, the term "modified" regarding a plant, refers to a plant with an altered phenotype (for example, a plant generated by genetic engineering, mutagenesis, or breeding methods). A genetically engineered plant can also be a transgenic plant. In particular embodiments, modified plants generated by breeding methods are first mutagenized using any one of a variety of mutagens, such as a chemical mutagen, radiation, or ultraviolet light. Modified plants can have any combination of an altered oil content, an altered protein content, and/or an altered fiber content in any part of the transgenic plant, for example the seeds, relative to a similar non-modified plant.

As used herein, the term "altered" refers to a change (either an increase or a decrease) of a plant trait or phenotype (for example, oil content, protein content, and/or fiber content) in a modified plant, relative to a similar non-modified plant. In one specific, non-limiting example, a modified plant with an altered trait includes a plant with an increased oil content, increased protein content, and/or decreased fiber content relative to a similar non-modified plant. In another specific, non-limiting example, a modified plant with an altered trait includes unchanged oil content, increased protein content, and/or decreased fiber content relative to a similar non-modified plant. In yet another specific, non-limiting example, a modified plant with an altered trait includes an increased oil content, increased protein content, and/or unchanged fiber content relative to a similar non-modified plant.

An "interesting phenotype (trait)" with reference to a modified plant refers to an observable or measurable phenotype demonstrated by a T1 and/or subsequent generation plant, which is not displayed by the corresponding non-modified plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such modified plants may have an improved phenotype, such as an altered oil, protein, and/or fiber phenotype. Meal generated from seeds of a modified plant with an improved phenotype can have improved (increased) meal quality. In a specific, non-limiting example of meal with an improved (increased) quality phenotype, meal is generated from a seed of a modified plant, wherein the seed has increased protein content and/or decreased fiber content, relative to a similar non-modified plant.

The phrase "altered oil content phenotype" refers to a measurable phenotype of a modified plant, where the plant displays a statistically significant increase or decrease in overall oil content (i.e., the percentage of seed mass that is oil), as compared to the similar, but non-modified (for example, a non-transgenic or a non-mutated) plant. A high oil phenotype refers to an increase in overall oil content. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Likewise, a decrease in oil content includes about a 1.0%, 1.5%, 2.0%, 2.5%, 3.0%, 3.5%, 4.0%, 4.5%, 5.0%, 7.5%, 10%, or more decrease in oil content, in various embodiments.

The phrase "altered protein content phenotype" refers to measurable phenotype of a modified plant, where the plant displays a statistically significant increase or decrease in overall protein content (i.e., the percentage of seed mass that is protein), as compared to the similar, but non-modified (for example, non-transgenic or non-mutated) plant. A high protein phenotype refers to an increase in overall protein content. An increase in protein content includes, in various embodiments, about a 1.0%, 1.5%, 2.0%, 2.5%, 3.0%, 3.5%, 4.0%, 4.5%, 5.0%, 7.5%, 10%, or more increase in total protein content. Likewise, an increase in digestible protein content includes, in various embodiments, about a 1.0%, 1.5%, 2.0%, 2.5%, 3.0%, 3.5%, 4.0%, 4.5%, 5.0%, 7.5%, 10%, or more increase in digestible protein content. A decrease in protein content includes about a 1.0%, 1.5%, 2.0%, 2.5%, 3.0%, 3.5%, 4.0%, 4.5%, 5.0%, 7.5%, 10%, or more decrease in total protein content, in various embodiments. Likewise, a decrease in digestible protein content includes, in various embodiments, about a 1.0%, 1.5%, 2.0%, 2.5%, 3.0%, 3.5%, 4.0%, 4.5%, 5.0%, 7.5%, 10%, or more decrease in digestible protein content. The phrase "altered fiber content phenotype" refers to measurable phenotype of a modified plant, where the plant displays a statistically significant increase or decrease in overall fiber content (i.e., the percentage of seed mass that is fiber), as compared to the similar, but non-modified (for example, non-transgenic or non-mutated) plant. A low fiber phenotype refers to decrease in overall fiber content. An increase in fiber content includes about a 1.0%, 1.5%, 2.0%, 2.5%, 3.0%, 3.5%, 4.0%, 4.5%, 5.0%, 7.5%, 10%, or more increase in fiber content. Likewise, a decrease in fiber content includes about a 1.0%, 1.5%, 2.0%, 2.5%, 3.0%, 3.5%, 4.0%, 4.5%, 5.0%, 7.5%, 10%, or more decrease in fiber content.

As used herein, a "mutant" or "mutated" polynucleotide sequence or gene differs from the corresponding wild-type polynucleotide sequence or gene either in terms of sequence or expression, where the difference contributes to an altered plant phenotype or trait. Relative to a plant or plant line, the term "mutant" or "mutated" refers to a plant or plant line which has an altered plant phenotype or trait, where the altered phenotype or trait is associated with the altered expression of a wild-type polynucleotide sequence or gene. The mutated polynucleotide sequence or gene can be generated by genetic engineering methods (such as activation tagging or transformation), by using one or more mutagens (for example, chemical mutagens, radiation, or ultraviolet light), or by using methods to alter a DNA sequence (for example, error prone PCR, DNA shuffling molecular breeding, site-directed mutagenesis, or introducing the gene into a mutagenizing organism such as *E. coli* or yeast strains that are deficient in DNA repair activity).

As used herein, the term "T1" refers to the generation of plants from the seed of T0 plants. The T1 generation is the first set of modified plants that can be selected by application of a selection agent, e.g., an antibiotic or herbicide, for which the modified plant contains the corresponding resistance gene. The term "T2" refers to the generation of plants by self-fertilization of the flowers of T1 plants, previously selected as being modified. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a modified plant cell having an altered phenotype. In particular embodiments, the modified plant cell is a transgenic plant cell. The transgenic plant cell includes a transformation vector comprising an HIO nucleotide sequence that encodes or is complementary to a sequence that encodes an HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are modified plants having an altered phenotype. Modified plants with an altered phenotype may include an improved (increased) oil quantity and/or an improved (increased) meal quality, as compared to the similar, but non-modified (for example, non-transgenic or non-mutated) plant. Modified plants with an altered phenotype may include altered oil, protein, and/or fiber content in any part of the modified plant, for example in the seeds, as compared to the similar, but non-modified (for example, non-transgenic or non-mutated) plant. In some embodiments of a modified plant, for example in plants with an improved or increased oil content phenotype, the altered phenotype includes an increase in the oil content of the seed (a high oil phenotype) from the plant, as compared to the similar, but non-modified (non-transgenic or non-mutated) plant. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. The altered phenotype can be an increase in one or more fatty acids, such as oleic acid, with a concominant decrease in other fatty acids such as linoleic or linolinic acids. A change in fatty acid content includes about a 5%, 10%, 20%, 30%, 40%, 50%, 60%, 70%, 80%, 90%, 100% or more increase in a specific fatty acid. In other embodiments of a modified plant, for example in plants with an improved or increased meal quality phenotype, the altered phenotype may be an increase in protein content in the seed and/or a decrease in the fiber content of the seed. An increase in protein content includes about a 1.0%, 1.5%, 2.0%, 2.5%, 3.0%, 3.5%, 4.0%, 4.5%, 5.0%, 7.5%, 10%, or more increase in protein content, for instance total protein content or digestible protein content. This change in seed protein content can be the result of altered amounts of seed storage proteins such as albumins, globulins prolamins, and glutelins. A decrease in fiber content includes about a 1.0%, 1.5%, 2.0%, 2.5%, 3.0%, 3.5%, 4.0%, 4.5%, 5.0%, 7.5%, 10%, or more decrease in fiber content. This change in fiber content can be the result of altered amounts of fibrous components such as cellulose, hemicellulose, lignin and pectins.

Also provided is seed meal derived from the seeds of modified plants, wherein the seeds have altered (for example, increased) protein (for example, digestible) content and/or altered (for example, decreased) fiber content. Further provided is oil derived from the seeds of modified plants, wherein the seeds have altered oil content. Any of these changes can lead to an increase in the AME from the seed or seed meal from modified plants, relative to control, non-transgenic, or wild-type plants. An increase in the AME includes about a 1.0%, 1.5%, 2.0%, 2.5%, 3.0%, 3.5%, 4.0%, 4.5%, 5.0%, 7.5%, 10%, or more increase in AME in the seed or seed meal, in various embodiments. Also provided herein is meal, feed, or food produced from any part of the modified plant with an altered phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill or limit the growth of the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin, neomycin, G418, bleomycin, methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 or Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Phenotype

An *Arabidopsis* activation tagging screen (ACTTAG) was used to identify the association between 1) ACTTAG plant lines with an altered oil, protein and/or fiber content (see columns 4, 5 and 6 respectively, of Table 1, below) and 2) the nucleic acid sequences identified in column 3 of Tables 2 and 3, wherein each nucleic acid sequence is provided with a gene alias or a HIO designation (HIO#; see column 1 in Tables 1, 2, and 3). The HIO designation is arbitrary and does not necessarily relate to a plant having a high oil (HIO) phenotype.

Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000, *Plant Physiology,* 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

The association of a HIO nucleic acid sequence with an altered phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed HIO nucleic acid sequences and/or polypeptides may be employed in the development of transgenic plants having an altered, for example high oil, phenotype. HIO nucleic acid sequences may be used in the generation of transgenic plants, such as oilseed crops, that provide improved oil yield from oilseed processing and result in an increase in the quantity of oil recovered from seeds of the transgenic plant. HIO nucleic acid sequences may also be used in the generation of transgenic plants, such as feed grain crops, that provide an altered phenotype resulting in increased energy for animal feeding, for example, seeds or seed meal with an altered protein and/or fiber content, resulting in an increase in AME. HIO nucleic acid sequences may further be used to increase the oil content of specialty oil crops, in order to augment yield and/or recovery of desired unusual fatty acids. Specific non-limiting examples of unusual fatty acids are ricinoleic acid, vernolic acid and the very long chain polyunsaturated fatty acids docosahexaenoic acid (DHA) and eicosapentaenoic acid (EPA). Transgenic plants that have been genetically modified to express HIO polypeptides can be used in the production of seeds, wherein the transgenic plants are grown, and oil and seed meal are obtained from plant parts (e.g. seed) using standard methods.

HIO Nucleic Acids and Polypeptides

The HIO designation for each of the HIO nucleic acid sequences discovered in the activation tagging screen described herein are listed in column 1 of Tables 1-3, below. The disclosed HIO polypeptides are listed in column 4 of Tables 2 and 3, below. The HIO designation is arbitrary and does not necessarily relate to a plant having a high oil (HIO) phenotype. As used herein, the gene alias or HIO designation refers to any polypeptide sequence (or the nucleic acid sequence that encodes it) that when expressed in a plant causes an altered phenotype in any part of the plant, for example the seeds. In one embodiment, a HIO polypeptide refers to a full-length HIO protein, or a fragment, derivative (variant), or ortholog or paralog thereof that is "functionally active," such that the protein fragment, derivative, or ortholog or paralog exhibits one or more or the functional activities associated with one or more of the disclosed full-length HIO polypeptides, for example, the amino acid sequences provided in the GenBank entry referenced in column 4 of Table 2, and 3 which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, or an ortholog or paralog thereof. In one preferred embodiment, a functionally active HIO polypeptide causes an altered phenotype in a transgenic plant. In another embodiment, a functionally active HIO polypeptide causes an altered oil, protein, and/or fiber content phenotype (for example, an altered seed meal content phenotype) when mis-expressed in a plant. In other preferred embodiments, mis-expression of the HIO polypeptide causes a high oil (such as, increased oil), high protein (such as, increased total protein or digestible protein), and/or low fiber (such as, decreased fiber) phenotype in a plant. In yet other preferred embodiments, mis-expression of the HIO polypeptide causes unchanged oil, high protein (such as, increased total protein or digestible protein), and/or low fiber (such as, decreased fiber) phenotype in a plant. In another embodiment, mis-expression of the HIO polypeptide causes an improved AME of meal. In yet another embodiment, a functionally active HIO polypeptide can rescue defective (including deficient) endogenous HIO polypeptide activity when expressed in a plant or in plant cells; the rescuing polypeptide may be from the same or from a different species as the species with the defective polypeptide activity. The disclosure also provides feed, meal, grain, food, or seed comprising the HIO polypeptide, or a fragment, derivative (variant), or ortholog or paralog thereof.

In another embodiment, a functionally active fragment of a full length HIO polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, or a naturally occurring ortholog or paralog thereof) retains one or more of the biological properties associated with the full-length HIO polypeptide, such as signaling activity, binding activity, catalytic activity, or cellular or extra-cellular localizing activity. A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 6 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length HIO polypeptides, or fragments thereof, include polypeptides with amino acid insertions, deletions, or substitutions that retain one of more of the biological properties associated with the full-length HIO polypeptide. In some cases, variants are generated that change the post-translational processing of an HIO polypeptide. For instance, variants may have altered protein transport or protein localization characteristics, or altered protein half-life, compared to the native polypeptide.

As used herein, the term "HIO nucleic acid" refers to any polynucleotide that when expressed in a plant causes an altered phenotype in any part of the plant, for example the seeds. In one embodiment, a HIO polynucleotide encompasses nucleic acids with the sequence provided in or complementary to the GenBank entry referenced in column 3 of Tables 2 and 3, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33, as well as functionally active fragments, derivatives, or orthologs or paralogs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. A functionally active HIO nucleic acid also includes genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes an HIO polypeptide.

In one preferred embodiment, a HIO nucleic acid used in the disclosed methods comprises a nucleic acid sequence that encodes, or is complementary to a sequence that encodes, a HIO polypeptide having at least 50%, 60%, 70%, 75%, 80%, 85%, 90%, 95%, 97%, 98%, or 99% sequence identity to a disclosed HIO polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34.

In another embodiment, a HIO polypeptide comprises a polypeptide sequence with at least 50% or 60% identity to a disclosed HIO polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34) and may have at least 70%, 80%, 85%, 90%, 95%, 97%, 98%, or 99% sequence identity to a disclosed HIO polypeptide sequence. In a further embodiment, a HIO polypeptide comprises 50%, 60%, 70%, 80%, 85%, 90%, 95%, 97%, 98%, or 99% sequence identity to a disclosed HIO polypeptide sequence, and may include a conserved protein domain of the HIO polypeptide (such as the protein domain(s) listed in column 6 of Table 2). In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide referenced in column 4 of Table 2. In yet another embodiment, a HIO polypeptide comprises a polypeptide sequence with at least 50%, 60%, 70%, 80%, 90%, 95%, 97%, 98%, or 99% identity to the polypeptide sequence of the GenBank entry referenced in column 4 of Table 2 over its entire length and comprises a conserved protein domain(s) listed in column 6 of Table 2.

In another aspect, a HIO polynucleotide sequence is at least 50% to 60% identical over its entire length to a disclosed HIO nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33, or nucleic acid sequences that are complementary to such a HIO sequence, and may comprise at least 70%, 80%, 85%, 90%, 95%, 97%, 98%, or 99% sequence identity to the disclosed HIO sequence, or a functionally active fragment thereof, or complementary sequences. In another embodiment, a disclosed HIO nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e., the sequences function in substantially the same manner and encode an HIO polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.*, 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed HIO nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6×single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs (and/or paralogs) of a disclosed *Arabidopsis* HIO nucleic acid sequence. Representative putative orthologs (and/or paralogs) of each of the disclosed *Arabidopsis* HIO genes are identified in column 5 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.,* 95:5849-5856; Huynen M A et al., 2000, *Genome Research,* 10:1204-1210).

Programs for multiple sequence alignment, such as CLUSTAL (Thompson J D et al., 1994, *Nucleic Acids Res.* 22:4673-4680) may be used to highlight conserved regions and/or residues of homologous (orthologous and/or paralogous) proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, or SEQ ID NO: 33, under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog (and/or paralog) isolation (see, e.g., Harlow and Lane, 1988, 1999, *Antibodies: A Laboratory Manual*, Cold Spring Harbor Laboratory Press, New York). Western blot analysis can determine that a HIO ortholog (i.e., a protein orthologous to a disclosed HIO polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the HIO nucleic acid into a plant expression vector for transformation of plant cells, and the HIO polypeptide is expressed in the host plant. Transformed plants and plant cells expressing an HIO polypeptide express an altered phenotype and, in one specific, non-limiting example, may have high (increased) oil, high (increased) protein, and/or low (decreased) fiber content.

An "isolated" HIO nucleic acid molecule is other than in the form or setting in which it is found in nature, and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express the HIO polypeptide where, for example, the nucleic acid molecule is in a chromosomal location different from that of natural cells.

Generation of Genetically Modified Plants with an Altered Phenotype

The disclosed HIO nucleic acids and polypeptides may be used in the generation of transgenic plants having a modified or altered phenotype, for example an altered oil, protein, and/or fiber content phenotype. As used herein, an "altered oil content (phenotype)" may refer to altered oil content in any part of the plant. In a preferred embodiment, altered expression of the HIO gene in a plant is used to generate plants with a high oil content (phenotype). As used herein, an "altered total protein content (phenotype)" or an "altered digestible protein content (phenotype)" may refer to altered protein (total or digestible) content in any part of the plant. In a preferred embodiment, altered expression of the HIO gene in a plant is used to generate plants with a high (or increased) total or digestible protein content (phenotype). As used herein, an "altered fiber content (phenotype)" may refer to altered fiber content in any part of the plant. In a preferred embodiment, altered expression of the HIO gene in a plant is used to generate plants with a low (or decreased) fiber content (phenotype). The altered oil, protein and/or fiber content is often observed in seeds. Examples of a transgenic plant include plants comprising a plant transformation vector with a nucleotide sequence that encodes or is complementary to a sequence that encodes an HIO polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34, or an ortholog or paralog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the HIO nucleic acid sequence (or an ortholog, paralog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the HIO nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol,* 91:694-701), maize (Ishida et al., 1996 *Nature Biotechnol.* 14:745-750, Zhang et al., 2002 *Plant Cell Rep.* 21:263-270) sunflower (Everett et al., 1987, *Bio/Technology,* 5:1201), soybean (Christou et al., 1989, *Proc. Natl. Acad. Sci USA,* 86:7500-7504; Kline et al., 1987, *Nature,* 327:70), wheat, rice and oat.

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of a HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci*. (U.S.A.) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al., 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci*. (U.S.A.) 84:6624-6628, 1987), the sucrose synthase promoter (Yang et al., *Proc. Natl. Acad. Sci*. (U.S.A.) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.,* 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol Bio.,* 21:625-640).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 oleosin promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7Sα' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba legumin* (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, *Plant Cell Physiol* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus napin,* 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus oleosin* (Keddie et al., 1994, *Plant Mol. Biol.* 24:327-40), *Arabidopsis oleosin* (Plant et al., 1994, *Plant Mol. Biol.* 25:193-205), *Arabidopsis* FAE1 (Rossak et al., 2001, *Plant*

*Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In another embodiment, the endogenous HIO gene may be placed under the control of a transgenic transcription factor or used to design binding sites that modulates its expression. One such class of transcription factors are the $Cys_2$-$His_2$-zinc finger proteins (ZFPs). ZFPs are common DNA binding proteins and can be designed to specifically bind to specific DNA sequences (Beerli & Barbas, Nat Biotechnol., 2002, 20:135-141.; Gommans et al., J. Mol Biol., 2005, 354:507-519). Individual zinc-finger domains are composed of approximately 30 amino acids, are structurally conserved and can interact with 3-4 bp of DNA. A polypeptide containing multiple zinc-fingers designed to bind to a specific DNA sequence in the promoter of a HIO gene can be synthesized. The principles for designing the zinc finger domains to interact with specific DNA sequences have been described in Segal et al., (Segal et al., Proc Natl Acad Sci USA, 1999, 96:2758-2763), Dreier et al. (Dreier et al., J Mol Biol., 2000, 303:489-502), and Beerli and Barbas (Beerli & Barbas, Nat Biotechnol., 2002, 20:135-141). These DNA binding domains may be fused to effector domains to form a synthetic ZFP that may regulate transcription of genes to which they bind. Effector domains that can activate transcription include but are not limited to the acidic portion of the herpes simplex virus protein VP16 (Sadowski et al., Nature., 1988, 335:563-564) and VP64 (Beerli et al., Proc Natl Acad Sci USA., 1998, 95:14628-14633), and the NF-κB transcription factor p65 domain (Bae et al., Nat Biotechnol., 2003, 21:275-280, Liu et al., J Biol Chem., 2001, 276:11323-11334). Effector domains that can repress transcription include but are not limited to mSIN3 and KRAB (Ayer et al., Mol Cell Biol., 1996, 16:5772-5781, Beerli & Barbas, Nat Biotechnol., 2002, 20:135-141, Beerli et al., Proc Natl Acad Sci USA, 1998, 95:14628-14633, Margolin et al., Proc Natl Acad Sci USA., 1994, 91:4509-4513). These approaches have been shown to work in plants (Guan et al., Proc Natl Acad Sci USA., 2002, 99:13296-13301, Stege et al., Plant J., 2002, 32:1077-1086, Van Eenennaam et al., Metab Eng., 2004, 6:101-108).

In yet another aspect, in some cases it may be desirable to inhibit the expression of the endogenous HIO nucleic acid sequence in a host cell. Exemplary methods for practicing this aspect of the invention include, but are not limited to antisense suppression (Smith, et al., 1988, *Nature,* 334:724-726; van der Krol et al., 1988, *BioTechniques,* 6:958-976); co-suppression (Napoli, et al., 1990, *Plant Cell,* 2:279-289); ribozymes (PCT Publication WO 97/10328); and combinations of sense and antisense (Waterhouse, et al., 1998, *Proc. Natl. Acad. Sci. USA,* 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA,* 85:8805-8809), a partial cDNA sequence including fragments of 5' coding sequence, (Cannon et al., 1990, *Plant Mol Biol.,* 15:39-47), or 3' non-coding sequences (Ch'ng et al., 1989, *Proc. Natl. Acad. Sci. USA,* 86:10006-10010). Cosuppression techniques may use the entire cDNA sequence (Napoli et al., 1990, *Plant Cell,* 2:279-289; van der Krol et al., 1990, *Plant Cell,* 2:291-299), or a partial cDNA sequence (Smith et al., 1990, *Mol. Gen. Genetics,* 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Phenotype

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen (such as ethylmethane sulfonate, methyl methane sulfonate, diethylsulfate, and nitrosoguanidine, or 5-bromo-deoxyuridine) radiation, or ultraviolet light. In some embodiments of the method, the mutated plant can be bred to generate progeny, which inherit the mutation or allele and have an altered phenotype. For example, provided herein is a method of identifying plants that have one or more mutations in the endogenous HIO nucleic acid sequence that confer an altered phenotype and generating progeny of these mutated plants having such a phenotype that are not transgenic. The mutated plants with an altered phenotype can have an altered oil, protein, and/or fiber content, or an altered seed meal content.

In one specific embodiment of the method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the HIO nucleic acid sequence is used to identify whether a mutated plant has a mutation in the HIO nucleic acid sequence. Plants having HIO mutations may then be tested for altered oil, protein, and/or fiber content. To confirm that the HIO mutation causes the modified phenotype, experiments correlating the presence of the modified gene and the modified phenotype through genetic crosses can be performed. TILLING can identify mutations that alter the expression of specific genes or the activity of proteins encoded by these genes (see Colbert et al., 2001, *Plant Physiol.* 126:480-484; McCallum et al., 2000, *Nature Biotechnology* 18:455-457).

In another specific embodiment of the method, a candidate gene/Quantitative Trait Locus (QTLs) approach can be used in a marker-assisted breeding program to identify alleles of or mutations in the HIO nucleic acid sequence or orthologs (and/or paralogs) of the HIO nucleic acid sequence that may confer altered oil, protein, and/or fiber content (see Bert et al., *Theor Appl Genet.,* 2003 June; 107(1):181-9; and Lionneton et al., *Genome,* 2002 December; 45(6):1203-15). Thus, in a further aspect of the disclosure, a HIO nucleic acid is used to identify whether a plant having altered oil, protein, and/or fiber content has a mutation in an endogenous HIO nucleic acid sequence or has a particular allele that causes altered oil, protein, and/or fiber content in the plant.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with a HIO Phenotype by Transformation with an Activation Tagging Construct This Example describes the generation of transgenic plants with altered oil, protein, and/or fiber content.

Mutants were generated using the activation tagging "ACTTAG" vector, pSKI015 (GI#6537289; Weigel D et al., 2000, *Plant Physiology,* 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR total protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A NIR fiber content predicting calibration was developed using crude fiber content data of seed samples following the general method of AOAC Official Method 962.09 (Official Methods of Analysis of AOAC International 17$^{th}$ Edition AOAC, Gaithersburg, Md.). A NIR oleic acid content predicting calibration was developed using oleic acid content data of seed samples determined by following the method of Browse et al. (1986 Anal. Biochem. 152:141-145). A NIR calibration curve for predicting digestible protein content was developed by measuring digestible protein content in a set of seed samples. Total protein content of in a known mass of seed was determined by measuring the total nitrogen content of the seed using the Dumas method (AOAC Official Method 968.06). The seed fiber is extracted from a separate seed sample using the method of Honig and Rackis, (1979, *J. Agri. Food Chem.,* 27: 1262-1266). The undigested protein remaining associated with the fiber is measured by the Dumas method (AOAC Official Method 968.06). Digestible protein content is determined by subtracting the amount of undigested protein associated with the fiber from the total amount of protein in the seed.

Oil, protein and fiber predictions from NIR spectra were compared for 82,274 individual ACTTAG lines. Subsequent to seed compositional analysis, the position of the ACTTAG element in the genome in each line was determined by inverse PCR and sequencing. 37,995 lines with recovered flanking sequences were considered in this analysis.

Seed oil, and protein values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Generally, promoters within 9 kb of the enhancers in the ACTTAG element are considered to be within "activation space." Genes with T-DNA inserts within coding sequences were not considered to be within "activation space." The ACTTAG lines identified are listed in column 3 of Table 1. In some cases more than one ACTTAG line is associated with a gene. The relative oil, protein, fiber and oleic acid values in columns 4, 5, 6 and 7, respectively, are determined by comparing the seed component in the plant identified in column 3 relative to other plants grown at the same time and not displaying the trait.

TABLE 1

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2011 B | At4g10540 | IN081274 | 121.52 | 85.77 | 112.19 | 170.91 |
| HIO2022 A | At1g21160 | IN070576 | 117.87 | 86.36 | 105.35 | 131.71 |
| HIO2022 A | At1g21160 | IN081625 | 108.6 | 94.24 | 102.16 | 127.55 |
| HIO2024 A | At5g43820 | IN078194 | 117.12 | 84.22 | 98.87 | 93.6 |
| HIO2024 A | At5g43820 | IN077533 | 110.52 | 97.43 | 97.63 | 101.01 |
| HIO2029 A | At4g21880 | IN040221 | 112.12 | 91.32 | 105.08 | 98.4 |
| HIO2036 A | At1g35610 | IN003383 | 110.63 | 95.26 | 102.61 | 107.39 |
| HIO2044 A | At1g07200 | IN085633 | 136.02 | 215.34 | 33.73 | |
| HIO2044 A | At1g07200 | IN065584 | 110.22 | 94.36 | 107.98 | 109.02 |
| HIO2062 B | At3g21530 | IN075911 | 112.25 | 97.43 | 128.26 | 121.82 |
| HIO2062 B | At3g21530 | IN010283 | 105.43 | 87.91 | 103.95 | 102.14 |
| HIO2070 B | At1g03230 | IN051870 | 110.64 | 97.08 | 92.8 | 99.68 |
| HIO2070 B | At1g03230 | IN027452 | 106.6 | 95.11 | 104.3 | 103.25 |
| HIO2079 B | At1g71420 | IN083604 | 131.01 | 83.85 | 99.94 | 139.75 |
| HIO2079 B | At1g71420 | IN090912 | 111.54 | 94.45 | 102.28 | 121.4 |
| HIO2084 A | At3g12020 | IN003802 | 115.88 | 86.87 | 92.23 | 35.51 |
| HIO2084 A | At3g12020 | IN090757 | 114.25 | 89.69 | 104.06 | 190.46 |
| HIO2091 B | At1g09850 | IN086447 | 139.97 | 124.86 | 65.1 | |
| HIO2091 B | At1g09850 | IN056625 | 104.65 | 106.59 | 100.56 | 103.87 |
| HIO2093 A | At5g61370 | IN088828 | 137.19 | 136.19 | 56.9 | |
| HIO2093 A | At5g61370 | IN013278 | 107.74 | 98.35 | 105.92 | 114.61 |
| HIO2093 C | At5g61390 | IN088828 | 137.19 | 136.19 | 56.9 | |
| HIO2093 C | At5g61390 | IN000614 | 109.24 | 92.2 | 104.2 | 106.81 |
| HIO2094 C | At3g13224 | IN090531 | 128.14 | 75.88 | 117.6 | |
| HIO2094 C | At3g13224 | IN041823 | 108.28 | 98.85 | 97.35 | 102.03 |
| HIO2094 D | At3g13227 | IN090531 | 128.14 | 75.88 | 117.6 | |
| HIO2094 D | At3g13227 | IN041823 | 108.28 | 98.85 | 97.35 | 102.03 |
| HIO2104 B | At4g33900 | IN067514 | 117.59 | 88.13 | 96.25 | 121.81 |

TABLE 2

| 1. Locus | 2. Tair ID | 3. Nucleic Acid seq. GI# | 4. Poly-peptide seq. GI# | 5. Putative biochemical function/protein name | 6. Conserved protein domain |
|---|---|---|---|---|---|
| HIO2022 A | At1g21160 | gi\|42562216 | gi\|15218159 | eukaryotic translation initiation factor 2 family protein/eIF-2 family protein | IPR000795 Protein synthesis factor, GTP-binding<br>IPR002917 GTP-binding protein, HSR1-related<br>IPR004161 Elongation factor Tu, domain 2<br>IPR010528 TolA<br>IPR004130 Conserved hypothetical ATP binding protein |
| HIO2024 A | At5g43820 | gi\|18422375 | gi\|15239991 | pentatricopeptide (PPR) repeat-containing protein | IPR002885 Pentatricopeptide repeat |
| HIO2029 A | At4g21880 | gi\|30685605 | gi\|30685606 | pentatricopeptide (PPR) repeat-containing protein | IPR002885 Pentatricopeptide repeat |
| HIO2036 A | At1g35610 | gi\|18399770 | gi\|15219660 | DC1 domain-containing protein | IPR004146 DC1<br>IPR011424 C1-like<br>IPR001965 Zn-finger-like, PHD finger |
| HIO2044 A | At1g07200 | gi\|30680018 | gi\|22329388 | ATP-dependent Clp protease ClpB protein-related | IPR001270 Chaperonin clpA/B |
| HIO2062 B | At3g21530 | GI:42565085 | gi\|42565086 | endonuclease/exonuclease/ phosphatase family protein | IPR005135 Endonuclease/exonuclease/ phosphatase<br>IPR004808 Exodeoxyribonuclease III xth<br>IPR000097 AP endonuclease, family 1 |
| HIO2070 B | At1g03230 | gi\|42561644 | gi\|18379072 | extracellular dermal glycoprotein, putative/EDGP, putative | |
| HIO2079 B | At1g71420 | gi\|18409850 | gi\|15217470 | pentatricopeptide (PPR) repeat-containing protein | IPR002885 Pentatricopeptide repeat |
| HIO2084 A | At3g12020 | gi\|22331005 | gi\|22331006 | kinesin motor protein-related | IPR001752 Kinesin, motor region |
| HIO2091 B | At1g09850 | gi\|30681401 | gi\|18391078 | cysteine protease, papain-like (XBCP3) | IPR000169 Peptidase, eukaryotic cysteine peptidase active site |

TABLE 2-continued

| 1. Locus | 2. Tair ID | 3. Nucleic Acid seq. GI# | 4. Poly-peptide seq. GI# | 5. Putative biochemical function/protein name | 6. Conserved protein domain |
|---|---|---|---|---|---|
| | | | | | IPR000668 Peptidase C1A, papain<br>IPR000118 Granulin |
| HIO2093 A | At5g61370 | gi\|30697519 | gi\|15240232 | pentatricopeptide (PPR) repeat-containing protein | IPR002885 Pentatricopeptide repeat |
| HIO2093 C | At5g61390 | gi\|42568688 | gi\|42568689 | exonuclease family protein | IPR006055 Exonuclease<br>IPR006054 DNA polymerase III, epsilon subunit |
| HIO2094 C | At3g13224 | GI:30682549 | GI:30682550 | RNA recognition motif (RRM)-containing protein | IPR000504 RNA-binding region RNP-1 (RNA recognition motif)<br>IPR009909 Nmi/IFP 35<br>IPR002343 Paraneoplastic encephalomyelitis antigen |
| HIO2094 C | At3g13224 | GI:30682552 | GI:30682553 | RNA recognition motif (RRM)-containing protein | IPR000504 RNA-binding region RNP-1 (RNA recognition motif)<br>IPR009909 Nmi/IFP 35<br>IPR002343 Paraneoplastic encephalomyelitis antigen |
| HIO2094 D | At3g13227 | GI:30682556 | gi\|22331053 | serine-rich protein-related | |
| HIO2011 B | At4g10540 | gi\|18413350 | gi\|18413351 | subtilase family protein | IPR010259 Proteinase inhibitor I9, subtilisin propeptide<br>IPR003137 Protease-associated PA<br>IPR000209 Peptidase S8 and S53, subtilisin, kexin, sedolisin |
| HIO2104 B | At4g33900 | gi\|18418316 | gi\|18418317 | kelch repeat-containing F-box family protein | IPR006652 Kelch repeat<br>IPR011498 Kelch<br>IPR001810 Cyclin-like F-box |

TABLE 3

| | | | | 5. Orthologs | | |
|---|---|---|---|---|---|---|
| 1. Locus | 2. Tair ID | 3. Nucleic Acid seq. GI# | 4. Polypeptide seq. GI# | Nucleic Acid GI# | Polypeptide GI# | Species |
| HIO2022 A | At1g21160 | gi\|42562216 | gi\|15218159 | gi\|42563274 | gi\|42563275 | *Arabidopsis thaliana* |
| | | | | gi\|30699194 | gi\|30699195 | *Arabidopsis thaliana* |
| | | | | gi\|23452070 | gi\|23452071 | *Pisum sativum* |
| HIO2024 A | At5g43820 | gi\|18422375 | gi\|15239991 | gi\|30685153 | gi\|15242190 | *Arabidopsis thaliana* |
| | | | | gi\|50918926 | gi\|50918927 | *Oryza sativa* (*japonica* cultivar-group) |
| | | | | gi\|34896697 | gi\|34896698 | *Oryza sativa* (*japonica* cultivar-group) |
| HIO2029 A | At4g21880 | gi\|30685605 | gi\|30685606 | gi\|30679876 | gi\|30679877 | *Arabidopsis thaliana* |
| | | | | gi\|50905060 | gi\|50905061 | *Oryza sativa* (*japonica* cultivar-group) |
| | | | | gi\|18415436 | gi\|15235288 | *Arabidopsis thaliana* |
| HIO2036 A | At1g35610 | gi\|18399770 | gi\|15219660 | gi\|18400150 | gi\|15231357 | *Arabidopsis thaliana* |
| | | | | gi\|42572370 | gi\|42572371 | *Arabidopsis thaliana* |
| | | | | gi\|18399212 | gi\|15229741 | *Arabidopsis thaliana* |
| HIO2044 A | At1g07200 | gi\|30680018 | gi\|22329388 | gi\|30680018 | gi\|22329388 | *Arabidopsis thaliana* |
| | | | | gi\|42569462 | gi\|18402202 | *Arabidopsis thaliana* |
| | | | | gi\|42568597 | gi\|15242850 | *Arabidopsis thaliana* |
| HIO2062 B | At3g21530 | GI:42565085 | gi\|42565086 | gi\|42570014 | gi\|18407510 | *Arabidopsis thaliana* |
| | | | | gi\|34898867 | gi\|34898868 | *Oryza sativa* (*japonica* cultivar-group) |

TABLE 3-continued

| 1. Locus | 2. Tair ID | 3. Nucleic Acid seq. GI# | 4. Polypeptide seq. GI# | 5. Orthologs | | |
|---|---|---|---|---|---|---|
| | | | | Nucleic Acid GI# | Polypeptide GI# | Species |
| | | | | gi\|21 229478 | gi\|21231641 | *Xanthomonas campestris* pv. *campestris* str. ATCC 33913 |
| HIO2070 B | At1g03230 | gi\|42561 644 | gi\|18379072 | gi\|30678499 | gi\|1 5218740 | *Arabidopsis thaliana* |
| | | | | gi\|285740 | gi\|285741 | *Daucus carota* |
| | | | | gi\|32482805 | gi\|32482806 | *Solanum tuberosum* |
| HIO2079 B | At1g71420 | gi\|18409850 | gi\|15217470 | gi\|18416131 | gi\|1 5242550 | *Arabidopsis thaliana* |
| | | | | gi\|30693149 | gi\|30693150 | *Arabidopsis thaliana* |
| | | | | gi\|50899005 | gi\|50899006 | *Oryza sativa* (*japonica* cultivar-group) |
| HIO2084 A | At3g12020 | gi\|22331005 | gi\|22331006 | gi\|22326628 | gi\|22326629 | *Arabidopsis thaliana* |
| | | | | gi\|30687505 | gi\|30687506 | *Arabidopsis thaliana* |
| | | | | gi\|50924423 | gi\|50924424 | *Oryza sativa* (*japonica* cultivar-group) |
| HIO2091 B | At1g09850 | gi\|30681401 | gi\|18391078 | gi\|50932272 | gi\|50932273 | Oryza sativa (*japonica* cultivar-group) |
| | | | | gi\|30694200 | gi\|1 8422289 | *Arabidopsis thaliana* |
| | | | | gi\|30141018 | gi\|30141019 | *Helianthus annuus* |
| HIO2093 A | At5g61370 | gi\|30697519 | gi\|15240232 | gi\|37534457 | gi\|37534458 | *Oryza sativa* (*japonica* cultivar-group) |
| | | | | gi\|30697448 | gi\|15239488 | *Arabidopsis thaliana* |
| | | | | gi\|30693231 | gi\|15229604 | *Arabidopsis thaliana* |
| HIO2093 C | At5g61390 | gi\|42568688 | gi\|42568689 | gi\|42567730 | gi\|15240840 | *Arabidopsis thaliana* |
| | | | | gi\|22330631 | gi\|15221225 | *Arabidopsis thaliana* |
| | | | | gi\|37534221 | gi\|37534222 | *Oryza sativa* (*japonica* cultivar-group) |
| HIO2094 C | At3g13224 | GI:30682549 | GI:30682550 | gi\|30682552 | gi\|30682553 | *Arabidopsis thaliana* |
| | | | | gi\|50944098 | gi\|50944099 | *Oryza sativa* (*japonica* cultivar-group) |
| | | | | gi\|50947154 | gi\|50947155 | *Oryza sativa* (*japonica* cultivar-group) |
| | | | | GI:51964985 | GI:51964986 | *Oryza sativa* (*japonica* cultivar-group) |
| HIO2094 C | At3g13224 | GI:30682552 | GI:30682553 | gi\|30682549 | gi\|30682550 | *Arabidopsis thaliana* |
| | | | | gi\|50944098 | gi\|50944099 | *Oryza sativa* (*japonica* cultivar-group) |
| | | | | gi\|50947154 | gi\|50947155 | *Oryza sativa* (*japonica* cultivar-group) |
| | | | | GI:51964985 | GI:51964986 | *Oryza sativa* (*japonica* cultivar-group) |
| HIO2094 D | At3g13227 | GI:30682556 | gi\|22331053 | GI:4105789 | GI:4105790 | *Petunia* x *hybrida* |
| | | | | GI:50905728 | GI:50905729 | *Oryza sativa* (*japonica* cultivar-group) |
| | | | | GI:30697586 | GI:15220581 | *Arabidopsis thaliana* |

TABLE 3-continued

| 1. Locus | 2. Tair ID | 3. Nucleic Acid seq. GI# | 4. Polypeptide seq. GI# | 5. Orthologs Nucleic Acid GI# | Polypeptide GI# | Species |
|---|---|---|---|---|---|---|
| HIO2011 B | At4g10540 | gi\|18413350 | gi\|18413351 | gi\|30681486 | gi\|18413353 | *Arabidopsis thaliana* |
| | | | | gi\|18413344 | gi\|18413345 | *Arabidopsis thaliana* |
| | | | | gi\|30692780 | gi\|18398655 | *Arabidopsis thaliana* |
| HIO2104 B | At4g33900 | gi\|18418316 | gi\|18418317 | GM8416176 | gi\|15236530 | *Arabidopsis thaliana* |
| | | | | GI:18418391 | gi\|15235260 | *Arabidopsis thaliana* |
| | | | | GI:18407622 | gi\|15229754 | *Arabidopsis thaliana* |

Example 2

Analysis of the *Arabidopsis* HIO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318), PSORT (Nakai K, and Horton P, 1999, *Trends Biochem. Sci.* 24:34-6), and/or CLUSTAL (Thompson J D et al., 1994, *Nucleic Acids Res.* 22:4673-4680).

Example 3

Recapitulation Experiments

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value$\leqq$0.05. These constructs are listed in Table 4. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

TABLE 4

| 1. Alias | 2. Tair | 3. Construct | ANOVA 4. Protein | 5. Oil | 6. Digestible Protein | 7. Fiber | Average 8. Protein | 9. Oil | 10. Digestible Protein | 11. Fiber |
|---|---|---|---|---|---|---|---|---|---|---|
| HIO2011 B | At4g10540 | CsVMV::At4g10540 | 0.498 | 0.736 | 0.854 | 0.789 | 98.5% | 100.7% | 100.2% | 100.3% |
| HIO2011 B | At4g10540 | Pru::At4g10540 | 0.680 | 0.107 | **0.004** | **0.002** | 99.4% | 103.3% | 102.9% | 95.9% |
| HIO2022 A | At1g21160 | CsVMV::At1g21160 | 0.245 | 0.689 | 0.084 | 0.067 | 103.5% | 98.2% | 99.6% | 100.7% |
| HIO2022 A | At1g21160 | Pru::At1g21160 | 0.538 | 0.119 | **0.034** | **0.003** | 101.5% | 102.3% | 102.9% | 96.0% |
| HIO2024 A | At5g43820 | CsVMV::At5g43820 | 0.582 | 0.131 | **0.005** | **0.047** | 99.3% | 102.6% | 102.4% | 96.9% |
| HIO2024 A | At5g43820 | Pru::At5g43820 | 0.074 | 0.864 | **0.033** | **0.039** | 103.5% | 99.8% | 102.0% | 97.3% |
| HIO2029 A | At4g21880 | CsVMV::At4g21880 | 0.119 | 0.159 | **0.002** | 0.372 | 101.4% | 98.3% | 102.1% | 99.2% |
| HIO2029 A | At4g21880 | Pru::At4g21880 | 0.533 | 0.054 | <.0001 | <.0001 | 101.1% | 102.8% | 104.2% | 94.5% |
| HIO2036 A | At1g35610 | CsVMV::At1g35610 | **0.040** | **0.001** | 0.314 | **0.005** | 97.0% | 106.5% | 100.9% | 96.3% |
| HIO2036 A | At1g35610 | Pru::At1g35610 | 0.776 | 0.780 | **0.008** | **0.025** | 100.6% | 100.6% | 103.0% | 97.2% |
| HIO2044 A | At1g07200 | CsVMV::At1g07200 | 0.815 | 0.336 | **0.037** | 0.069 | 100.3% | 101.8% | 101.7% | 97.7% |
| HIO2044 A | At1g07200 | Pru::At1g07200 | 0.134 | 0.202 | **0.000** | **0.001** | 102.0% | 102.3% | 103.3% | 95.7% |
| HIO2062 B | At3g21530 | CsVMV::At3g21530 | 0.709 | 0.423 | 0.256 | 0.145 | 99.5% | 100.7% | 100.7% | 99.1% |
| HIO2062 B | At3g21530 | Pru::At3g21530 | 0.316 | **0.024** | 0.756 | 0.160 | 98.3% | 102.8% | 99.8% | 98.8% |
| HIO2070 B | At1g03230 | CsVMV::At1g03230 | 0.966 | 0.618 | 0.258 | **0.044** | 100.1% | 101.1% | 101.0% | 98.1% |
| HIO2070 B | At1g03230 | Pru::At1g03230 | 0.995 | **0.019** | **0.018** | **0.003** | 100.1% | 102.8% | 102.3% | 96.8% |
| HIO2079 B | At1g71420 | CsVMV::At1g71420 | 0.297 | **0.033** | 0.083 | 0.058 | 99.0% | 102.7% | 101.2% | 98.0% |

TABLE 4-continued

| | | | ANOVA | | | | Average | | | |
|---|---|---|---|---|---|---|---|---|---|---|
| 1. Alias | 2. Tair | 3. Construct | 4. Protein | 5. Oil | 6. Digestible Protein | 7. Fiber | 8. Protein | 9. Oil | 10. Digestible Protein | 11. Fiber |
| HIO2079 B | At1g71420 | Pru::At1g71420 | 0.114 | 0.810 | **0.008** | **0.002** | 102.6% | 99.8% | 102.3% | 97.1% |
| HIO2084 A | At3g12020 | CsVMV::At3g12020 | 0.076 | 0.728 | 0.063 | 0.200 | 102.4% | 99.5% | 101.6% | 98.3% |
| HIO2084 A | At3g12020 | Pru::At3g12020 | 0.487 | **0.019** | **0.022** | **0.001** | 98.6% | 103.7% | 102.0% | 96.1% |
| HIO2091 B | At1g09850 | CsVMV::At1g09850 | **0.041** | 0.065 | 0.760 | 0.830 | 97.2% | 102.8% | 99.8% | 100.4% |
| HIO2091 B | At1g09850 | Pru::At1g09850 | 0.354 | 0.170 | 0.475 | 0.748 | 101.9% | 98.4% | 101.1% | 100.2% |
| HIO2093 A | At5g61370 | CsVMV::At5g61370 | 0.337 | 0.098 | 0.224 | 0.074 | 98.8% | 102.4% | 101.0% | 97.9% |
| HIO2093 A | At5g61370 | Pru::At5g61370 | 0.535 | 0.139 | <.0001 | <.0001 | 100.8% | 101.9% | 103.4% | 94.0% |
| HIO2093 C | At5g61390 | CsVMV::At5g61390 | 0.058 | 0.065 | 0.064 | 0.051 | 97.1% | 103.0% | 101.1% | 98.1% |
| HIO2093 C | At5g61390 | Pru::At5g61390 | 0.949 | 0.068 | **0.005** | **0.000** | 100.1% | 101.9% | 102.7% | 95.6% |
| HIO2094 C | At3g13224 | CsVMV::At3g13224 | 0.710 | 0.065 | 0.186 | 0.070 | 99.5% | 101.7% | 101.2% | 98.2% |
| HIO2094 C | At3g13224 | Pru::At3g13224 | **0.034** | 0.173 | **0.025** | 0.125 | 104.5% | 98.4% | 102.6% | 98.0% |
| HIO2094 D | At3g13227 | CsVMV::At3g13227 | 0.096 | **0.030** | 0.153 | **0.042** | 97.3% | 104.5% | 101.2% | 97.2% |
| HIO2094 D | At3g13227 | Pru::At3g13227 | **0.042** | **0.004** | 0.430 | <.0001 | 97.9% | 97.8% | 101.3% | 105.0% |
| HIO2104 B | At4g33900 | CsVMV::At4g33900 | **0.846** | **0.722** | 0.374 | 0.064 | 100.0% | 99.6% | 99.5% | 102.5% |
| HIO2104 B | At4g33900 | Pru::At4g33900 | **0.152** | **0.015** | 0.048 | 0.002 | 98.3% | 103.5% | 101.7% | 95.6% |

It is claimed:

1. A method of generating a plant having an increased oil content, comprising:

identifying a plant that has an allele in its ortholog of the *A. thaliana* HIO2084A gene, where the wild-type *A. thaliana* HIO2084A gene has the nucleic acid set forth as SEQ ID NO: 17, which allele results in increased oil content compared to plants lacking the allele; and generating progeny of said identified plant, wherein the generated progeny inherit the allele and have the high oil phenotype.

2. The method of claim 1 that employs candidate gene/QTL methodology.

3. The method of claim 1 that employs TILLING methodology.

4. A method of generating a plant having an improved meal quality phenotype comprising:

identifying a plant that has an allele in its ortholog of the *A. thaliana* HIO2084A gene, where the wild-type *A. thaliana* HIO2084A gene has the nucleic acid sequence set forth as SEQ ID NO: 17, which allele results in increased meal quality compared to plants lacking the allele; and generating progeny of said identified plant, wherein the generated progeny inherit the allele and have the increased meal quality, thereby generating a plant having an improved meal quality phenotype.

5. The method of claim 4 that employs candidate gene/QTL methodology.

6. The method of claim 4 that employs TILLING methodology.

* * * * *

SEQUENCE LISTING

```
<160> NUMBER OF SEQ ID NOS: 34

<210> SEQ ID NO 1
<211> LENGTH: 3603
<212> TYPE: DNA
<213> ORGANISM: Arabidopsis thaliana

<400> SEQUENCE: 1

ctcaaatata tctctgcaac gaaaagaaat cacctgctta ctcttctcct gaaagacctg      60

atcttctccg gtgaattgtt ttttgttccg tcaatcttcc gagtttgttt ttgcctaata     120

tgaagttaaa cccattacag aaaaaggcta tattcatatt tgatttctat caatggatcc     180

gaggaattcg agtgcgtggg gtgggggtga tggtctcccc cttatctcat ccatgggagg     240

tgttgaatca aagaatagat gctgtgtgac tgacgacgat ggctctattg gtacgaagct     300

atgtgagaaa cctaaagctg aggagattga tttttctgct cggaaaaaga agttgaaatc     360

gaagaaaggc gggtctgtta gctttgctct tctcgatgtt gaagatgaca aggaggaagc     420

agaggatgga gacgacaaaa atccttctat taggagtgat gaggtggttg gagaaacttc     480

aatgagtaag aaaaagaaga aggataagag tggcaagcat ggggtatgtg aagaagatga     540

tgatgcggac aagattcttg ctcaacatgg gataacaact actgtttcaa cagggcctga     600

agcggagata gctctagctc aacctgagca agttgcatct gcagatgggg ctgttgacaa     660

ggacggagaa gaaaagactg ttgagtcagc tacagcgaag aaaaagaaaa agaagaagga     720

caaggacaag aaagcaagtg cttctttagc tatttcttct gtggaggcta aggaggatag     780

acaagggaag aaagatgtaa agattaaagt agcggaaaag aaagttccta aacatgttcg     840

agagaagcaa gagactcttg cgcggtggaa agaagctgaa gatgggaaga agaaggaaga     900

agaagagaga ttgaggaaag aggaagagga gcgccgtata gaggaagagc gagaaaggga     960

agctgaagag attaggcaga agagaaagat caggaaaatg gagaagaagc aagaaggcct    1020

gattctaaca gcaaagcaaa agcgtgatgc tgctaagaat gaggctttca gaaaaagggt    1080

gttgactgat gctggaagtc ttcttgttgc agataaaaac ggtgattcct caaaacgtcc    1140

catatatggc aataaaaaca aattagcttg caaaaaagca aacgatcctg cttctgtcca    1200

ggctaaaggt gatggggaaa ccaaggaaaa tcatgcagca gatgaaccat gtactttacc    1260
```

-continued

```
tgacttggtt tcagttgaag atagaagggt tggtattatc gaatcagtag acacagaaga   1320
gacacatgaa tctgttgatg tatcacaaga gaatggtgat gaggaagatg tgtgggatgc   1380
aaaaactaat tttaccatca agggtgattc tgatgatgag gaggaaaaac ctcagcctgt   1440
gttcaagaaa ggtttaaaag acactgcatc aaaggcacat gattcagata gaccaacagt   1500
gaagcctgga ggttctggca agccaaaaac agctgccaaa aaagctatgc ctaaggtgga   1560
tgatactacc cggccgaaag atacttctaa aaaggatgaa ggcttagtac tgaatgaact   1620
tgctaaagaa gtagaagaaa atcttcgctc tccaatttgc tgcatcatgg gtcatgttga   1680
ttctggtaaa acaaagctgt tggattgcat cagaggaaca aatgttcagg aaggtgaagc   1740
tggaggtatt actcaacaga ttggtgcaac ctttttccct gcagaaaaca tccgtgagag   1800
gaccaaagag ttacaagcta atgctaaact caaggtgcca ggtatattgg ttatcgatac   1860
acctggacac gagtcattca caaatctgcg gtcaaggggt tcaaatttgt gtgaccttgc   1920
aattctagtg gttgatataa tgcgaggtct agagccacaa accatagaat ctcttaatct   1980
tttgagaaga aggaatgtaa agttcattat tgccttgaat aaggtggata ggctatatgg   2040
gtgggaaaaa agcaagaatg ctcctataag gaagacaatg atgcaacaaa cgggagatgt   2100
ggttaaggaa tttaaaatga ggctaaaccg agttcaaaac cagttccaag aacaaggact   2160
caacagtatg ctttattaca agaacagaga aatgggagaa actatcagta tcctacctgc   2220
tagcgctatt agtggggaag ggattccaga tcttttactg ttcttggttc aatgggctca   2280
gaaaacgatg gtggagaaac ttacatatgt tgacaaagtg cagtgtaccg tccttgaggt   2340
caaagttatt gaaggccatg gtattacagt tgatgttgtt ttggtcaacg gtgtactccg   2400
tgaaggtgat caaattgttg tttgtgggtc acagggacca attgtaacaa ctattagatc   2460
attgttgact ccttatccta tgaacgagat gcgggtgacg ggtacctata tgcctcacag   2520
agaagtaaag gctgcgcagg gtatcaaaat tgctgcacag ggccttgaac acgccattgc   2580
tggtactgcc ttgcatgtga ttggacctaa tgaggacatg gaagaagcca agaaaaatgc   2640
catggaagat attgagtcag ttatgaaccg cattgacaaa agtggtgaag gcgtttatgt   2700
acaagcatct acattagggt ccttggaagc attgctcgag ttcttgaagt cctcagatgt   2760
aaaaatacct gtcagtggta ttggcatagg acctgtgcat aagaaggata tcatgaaggc   2820
cggggtaatg ctagagaaga aaaaagagtt tgcaacgatt ttggcctttg atgtgaaaat   2880
aagtgcagaa gctcgtgaac ttgcagacaa aatgggagta aaaatcttct gcgatgatac   2940
catctattgt ctgttcgata agtttaagag ttacatagag ggtatcaaag aggagaaaaa   3000
gaaagaaaca gcttgtgaag cagttttccc atgtatcctt cagattttac caaaccatat   3060
ctacaatcag agggacccaa ttatccttgg agttaaagtc aatgatggaa tactaaaggt   3120
tggaactccc atttgcattg ttaaaaggat tgagaatgta agagtgttta tggacattgg   3180
gcgcgtctca tcaattaaga ataacaacaa catgccagtt gattatgcaa ggaaaggaca   3240
ggaggtggct attaagatca ttgcttctaa cccagaagaa cagaaaatgt ttgggaggca   3300
ctttggtgta gacgacaggc ttatcagtca catttctagt cgatccgtgg acgtaatcag   3360
aactaattac tggaatgagt tatctaacga cgagaaggat cttgttttga gacttaaaag   3420
gatattcaag atacaatgaa gatttttgag atttgagagt gagggactta aacttatgta   3480
tttttttct tttttgaag tgctgatttt tttatttttt tttcgttttt aataatatag   3540
acaaacaact cctttaatgc ccctaaatac tttatggaag caattgtctt ttgtttttgg   3600
```

-continued

```
cta                                                                     3603


<210> SEQ ID NO 2
<211> LENGTH: 1088
<212> TYPE: PRT
<213> ORGANISM: Arabidopsis thaliana

<400> SEQUENCE: 2

Met Asp Pro Arg Asn Ser Ser Ala Trp Gly Gly Gly Asp Gly Leu Pro
1               5                   10                  15

Leu Ile Ser Ser Met Gly Gly Val Glu Ser Lys Asn Arg Cys Cys Val
            20                  25                  30

Thr Asp Asp Asp Gly Ser Ile Gly Thr Lys Leu Cys Glu Lys Pro Lys
        35                  40                  45

Ala Glu Glu Ile Asp Phe Ser Ala Arg Lys Lys Lys Leu Lys Ser Lys
    50                  55                  60

Lys Gly Gly Ser Val Ser Phe Ala Leu Leu Asp Val Glu Asp Asp Lys
65                  70                  75                  80

Glu Glu Ala Glu Asp Gly Asp Asp Lys Asn Pro Ser Ile Arg Ser Asp
                85                  90                  95

Glu Val Val Gly Glu Thr Ser Met Ser Lys Lys Lys Lys Lys Asp Lys
            100                 105                 110

Ser Gly Lys His Gly Val Cys Glu Glu Asp Asp Asp Ala Asp Lys Ile
        115                 120                 125

Leu Ala Gln His Gly Ile Thr Thr Thr Val Ser Thr Gly Pro Glu Ala
    130                 135                 140

Glu Ile Ala Leu Ala Gln Pro Glu Gln Val Ala Ser Ala Asp Gly Ala
145                 150                 155                 160

Val Asp Lys Asp Gly Glu Glu Lys Thr Val Glu Ser Ala Thr Ala Lys
                165                 170                 175

Lys Lys Lys Lys Lys Lys Asp Lys Asp Lys Lys Ala Ser Ala Ser Leu
            180                 185                 190

Ala Ile Ser Ser Val Glu Ala Lys Glu Asp Arg Gln Gly Lys Lys Asp
        195                 200                 205

Val Lys Ile Lys Val Ala Glu Lys Lys Val Pro Lys His Val Arg Glu
    210                 215                 220

Lys Gln Glu Thr Leu Ala Arg Trp Lys Glu Ala Glu Asp Gly Lys Lys
225                 230                 235                 240

Lys Glu Glu Glu Glu Arg Leu Arg Lys Glu Glu Glu Glu Arg Arg Ile
                245                 250                 255

Glu Glu Glu Arg Glu Arg Glu Ala Glu Glu Ile Arg Gln Lys Arg Lys
            260                 265                 270

Ile Arg Lys Met Glu Lys Lys Gln Glu Gly Leu Ile Leu Thr Ala Lys
        275                 280                 285

Gln Lys Arg Asp Ala Ala Lys Asn Glu Ala Phe Arg Lys Arg Val Leu
    290                 295                 300

Thr Asp Ala Gly Ser Leu Leu Val Ala Asp Lys Asn Gly Asp Ser Ser
305                 310                 315                 320

Lys Arg Pro Ile Tyr Gly Asn Lys Asn Lys Leu Ala Cys Lys Lys Ala
                325                 330                 335

Asn Asp Pro Ala Ser Val Gln Ala Lys Gly Asp Gly Glu Thr Lys Glu
            340                 345                 350

Asn His Ala Ala Asp Glu Pro Cys Thr Leu Pro Asp Leu Val Ser Val
        355                 360                 365
```

-continued

```
Glu Asp Arg Arg Val Gly Ile Ile Glu Ser Val Asp Thr Glu Glu Thr
    370                 375                 380

His Glu Ser Val Asp Val Ser Gln Glu Asn Gly Asp Glu Glu Asp Val
385                 390                 395                 400

Trp Asp Ala Lys Thr Asn Phe Thr Ile Lys Gly Asp Ser Asp Asp Glu
                405                 410                 415

Glu Glu Lys Pro Gln Pro Val Phe Lys Lys Gly Leu Lys Asp Thr Ala
            420                 425                 430

Ser Lys Ala His Asp Ser Asp Arg Pro Thr Val Lys Pro Gly Gly Ser
        435                 440                 445

Gly Lys Pro Lys Thr Ala Ala Lys Lys Ala Met Pro Lys Val Asp Asp
    450                 455                 460

Thr Thr Arg Pro Lys Asp Thr Ser Lys Lys Asp Glu Gly Leu Val Leu
465                 470                 475                 480

Asn Glu Leu Ala Lys Glu Val Glu Glu Asn Leu Arg Ser Pro Ile Cys
                485                 490                 495

Cys Ile Met Gly His Val Asp Ser Gly Lys Thr Lys Leu Leu Asp Cys
            500                 505                 510

Ile Arg Gly Thr Asn Val Gln Glu Gly Glu Ala Gly Gly Ile Thr Gln
        515                 520                 525

Gln Ile Gly Ala Thr Phe Phe Pro Ala Glu Asn Ile Arg Glu Arg Thr
    530                 535                 540

Lys Glu Leu Gln Ala Asn Ala Lys Leu Lys Val Pro Gly Ile Leu Val
545                 550                 555                 560

Ile Asp Thr Pro Gly His Glu Ser Phe Thr Asn Leu Arg Ser Arg Gly
                565                 570                 575

Ser Asn Leu Cys Asp Leu Ala Ile Leu Val Val Asp Ile Met Arg Gly
            580                 585                 590

Leu Glu Pro Gln Thr Ile Glu Ser Leu Asn Leu Leu Arg Arg Arg Asn
        595                 600                 605

Val Lys Phe Ile Ile Ala Leu Asn Lys Val Asp Arg Leu Tyr Gly Trp
    610                 615                 620

Glu Lys Ser Lys Asn Ala Pro Ile Arg Lys Thr Met Met Gln Gln Thr
625                 630                 635                 640

Gly Asp Val Val Lys Glu Phe Lys Met Arg Leu Asn Arg Val Gln Asn
                645                 650                 655

Gln Phe Gln Glu Gln Gly Leu Asn Ser Met Leu Tyr Tyr Lys Asn Arg
            660                 665                 670

Glu Met Gly Glu Thr Ile Ser Ile Leu Pro Ala Ser Ala Ile Ser Gly
        675                 680                 685

Glu Gly Ile Pro Asp Leu Leu Leu Phe Leu Val Gln Trp Ala Gln Lys
    690                 695                 700

Thr Met Val Glu Lys Leu Thr Tyr Val Asp Lys Val Gln Cys Thr Val
705                 710                 715                 720

Leu Glu Val Lys Val Ile Glu Gly His Gly Ile Thr Val Asp Val Val
                725                 730                 735

Leu Val Asn Gly Val Leu Arg Glu Gly Asp Gln Ile Val Val Cys Gly
            740                 745                 750

Ser Gln Gly Pro Ile Val Thr Thr Ile Arg Ser Leu Leu Thr Pro Tyr
        755                 760                 765

Pro Met Asn Glu Met Arg Val Thr Gly Thr Tyr Met Pro His Arg Glu
    770                 775                 780

Val Lys Ala Ala Gln Gly Ile Lys Ile Ala Ala Gln Gly Leu Glu His
```

-continued

```
785                 790                 795                 800

Ala Ile Ala Gly Thr Ala Leu His Val Ile Gly Pro Asn Glu Asp Met
                805                 810                 815

Glu Glu Ala Lys Lys Asn Ala Met Glu Asp Ile Glu Ser Val Met Asn
            820                 825                 830

Arg Ile Asp Lys Ser Gly Glu Gly Val Tyr Val Gln Ala Ser Thr Leu
        835                 840                 845

Gly Ser Leu Glu Ala Leu Leu Glu Phe Leu Lys Ser Ser Asp Val Lys
    850                 855                 860

Ile Pro Val Ser Gly Ile Gly Ile Gly Pro Val His Lys Lys Asp Ile
865                 870                 875                 880

Met Lys Ala Gly Val Met Leu Glu Lys Lys Lys Glu Phe Ala Thr Ile
                885                 890                 895

Leu Ala Phe Asp Val Lys Ile Ser Ala Glu Ala Arg Glu Leu Ala Asp
            900                 905                 910

Lys Met Gly Val Lys Ile Phe Cys Asp Asp Thr Ile Tyr Cys Leu Phe
        915                 920                 925

Asp Lys Phe Lys Ser Tyr Ile Glu Gly Ile Lys Glu Glu Lys Lys Lys
    930                 935                 940

Glu Thr Ala Cys Glu Ala Val Phe Pro Cys Ile Leu Gln Ile Leu Pro
945                 950                 955                 960

Asn His Ile Tyr Asn Gln Arg Asp Pro Ile Ile Leu Gly Val Lys Val
                965                 970                 975

Asn Asp Gly Ile Leu Lys Val Gly Thr Pro Ile Cys Ile Val Lys Arg
            980                 985                 990

Ile Glu Asn Val Arg Val Phe Met  Asp Ile Gly Arg Val  Ser Ser Ile
        995                 1000                1005

Lys Asn  Asn Asn Asn Met Pro  Val Asp Tyr Ala Arg  Lys Gly Gln
    1010                1015                1020

Glu Val  Ala Ile Lys Ile Ile  Ala Ser Asn Pro Glu  Glu Gln Lys
    1025                1030                1035

Met Phe  Gly Arg His Phe Gly  Val Asp Asp Arg Leu  Ile Ser His
    1040                1045                1050

Ile Ser  Ser Arg Ser Val Asp  Val Ile Arg Thr Asn  Tyr Trp Asn
    1055                1060                1065

Glu Leu  Ser Asn Asp Glu Lys  Asp Leu Val Leu Arg  Leu Lys Arg
    1070                1075                1080

Ile Phe  Lys Ile Gln
    1085


<210> SEQ ID NO 3
<211> LENGTH: 2043
<212> TYPE: DNA
<213> ORGANISM: Arabidopsis thaliana

<400> SEQUENCE: 3

atgcttagga gatggaacat agttattgaa tcgctacgtc gcgttcatag cagtgattta      60

gaaaacctaa tttcggcttc cctatacaat cgaacacttt gcacagcctc agaatcattg     120

aatcatggtg ttgttgatga gagttatgtt ctagctgaat tatcttcatt gcttccaatt     180

tcatctaata aaacctcagt gtcaaaggaa gacagtagct caaagaatca agtagctatt     240

gattcgtttt tgtcagcaga ggacaaactt agaggtgtgt ttcttcagaa attgaaaggc     300

aagtctgcta ttcagaagag tttgagtagt cttggtattg gtttgagtat tgacattgtt     360
```

-continued

```
gccgatgtat tgaatcgagg gaatttaagc ggcgaagcga tggtaacgtt ctttgattgg    420

gcggttcgtg agcctggtgt gactaaagat gttggtagct acagtgtgat tttaagagcg    480

ttaggaagga gaaagctttt ctcttttatg atggatgttc taaagggaat ggtatgtgaa    540

ggtgttaatc ctgatctgga gtgtttaact attgctatgg atagctttgt tagggttcat    600

tatgtgcgta gagcgataga gttgtttgag gaaagtgaaa gttttggggt gaaatgtagt    660

actgagtctt tcaatgcatt gttacggtgt ctatgtgagc gttcacatgt gagtgctgca    720

aagtcagtat ttaatgctaa gaaaggtaat ataccttttg atagttgtag ttataacatt    780

atgattagtg ggtggtcaaa gctcggtgag gttgaagaga tggaaaaggt tttgaaggag    840

atggtggaga gtggatttgg tcctgactgt ttgtcttata gccatcttat tgaagggttg    900

ggaagaactg gtcgtatcaa tgattctgtt gagatctttg ataatataaa acacaagggt    960

aatgttcctg atgcaaatgt ttacaatgct atgatctgta atttcatatc tgctcgagat   1020

tttgatgagt ctatgaggta ctaccgaagg atgctggatg aggaatgtga acctaacttg   1080

gaaacctatt ccaagcttgt ttctgggctc attaaaggcc gtaaggtttc tgatgcgctt   1140

gagatattcg aagagatgtt atcaagaggg gttcttccca ccacagggct tgttacctct   1200

ttcctcaagc ctctttgcag ctatggtcca ccacacgctg caatggttat ctatcagaaa   1260

tcaagaaaag ccgggtgtag gatatcagaa agcgcatata agctgttgct taagcggcta   1320

tcaagatttg gaaaatgcgg gatgctgttg aacgtatggg atgaaatgca agagtctgga   1380

tatccttctg acgtggaagt ctacgagtat attgtggatg ggctctgtat cattgggcat   1440

ctagagaatg ctgtgcttgt gatggaagaa gctatgcgta aagggttttg cccaaaccgc   1500

tttgtttata gtaggcttag cataattagg aaatggcagc agaagttcag aaaagggaag   1560

gaggagatgg aaaagtggga ggcacttcaa gttcgatggg tgtccctctt caggaacgct   1620

tcttctatca tccagagatt acaggaaatg caaaatcatg ggagctatgg agctttgaga   1680

tgcctgaaag ggattgaaga cgcagttgtg cagcaacaga tgggtcaact ggagtctcta   1740

ttgcgttcca tgaaaaacgt tatggaggaa ttctggggct gtgttttgac atttgagaag   1800

ctacatcggg acggtttaca gttacgtgaa attgaatcaa gcaagaggcg agtagaggaa   1860

cgaattggag taaaaccgtg cattactgat tgcttggagg gactttctat tctttatgac   1920

atgcatcaat cagatcctgg tgatctaaac gcgctacaat acctcgtggt tgatcagccg   1980

aatatcccga aagatgaagt acaacacatt ttcgatgtca tattcgcgga agagatcaaa   2040

tga                                                                 2043
```

<210> SEQ ID NO 4
<211> LENGTH: 680
<212> TYPE: PRT
<213> ORGANISM: Arabidopsis thaliana

<400> SEQUENCE: 4

```
Met Leu Arg Arg Trp Asn Ile Val Ile Glu Ser Leu Arg Arg Val His
1               5                   10                  15

Ser Ser Asp Leu Glu Asn Leu Ile Ser Ala Ser Leu Tyr Asn Arg Thr
            20                  25                  30

Leu Cys Thr Ala Ser Glu Ser Leu Asn His Gly Val Val Asp Glu Ser
        35                  40                  45

Tyr Val Leu Ala Glu Leu Ser Ser Leu Leu Pro Ile Ser Ser Asn Lys
    50                  55                  60

Thr Ser Val Ser Lys Glu Asp Ser Ser Ser Lys Asn Gln Val Ala Ile
```

-continued

```
65                  70                  75                  80

Asp Ser Phe Leu Ser Ala Glu Asp Lys Leu Arg Gly Val Phe Leu Gln
                85                  90                  95

Lys Leu Lys Gly Lys Ser Ala Ile Gln Lys Ser Leu Ser Ser Leu Gly
            100                 105                 110

Ile Gly Leu Ser Ile Asp Ile Val Ala Asp Val Leu Asn Arg Gly Asn
        115                 120                 125

Leu Ser Gly Glu Ala Met Val Thr Phe Phe Asp Trp Ala Val Arg Glu
    130                 135                 140

Pro Gly Val Thr Lys Asp Val Gly Ser Tyr Ser Val Ile Leu Arg Ala
145                 150                 155                 160

Leu Gly Arg Arg Lys Leu Phe Ser Phe Met Met Asp Val Leu Lys Gly
                165                 170                 175

Met Val Cys Glu Gly Val Asn Pro Asp Leu Glu Cys Leu Thr Ile Ala
            180                 185                 190

Met Asp Ser Phe Val Arg Val His Tyr Val Arg Arg Ala Ile Glu Leu
        195                 200                 205

Phe Glu Glu Ser Glu Ser Phe Gly Val Lys Cys Ser Thr Glu Ser Phe
    210                 215                 220

Asn Ala Leu Leu Arg Cys Leu Cys Glu Arg Ser His Val Ser Ala Ala
225                 230                 235                 240

Lys Ser Val Phe Asn Ala Lys Lys Gly Asn Ile Pro Phe Asp Ser Cys
                245                 250                 255

Ser Tyr Asn Ile Met Ile Ser Gly Trp Ser Lys Leu Gly Glu Val Glu
            260                 265                 270

Glu Met Glu Lys Val Leu Lys Glu Met Val Glu Ser Gly Phe Gly Pro
        275                 280                 285

Asp Cys Leu Ser Tyr Ser His Leu Ile Glu Gly Leu Gly Arg Thr Gly
    290                 295                 300

Arg Ile Asn Asp Ser Val Glu Ile Phe Asp Asn Ile Lys His Lys Gly
305                 310                 315                 320

Asn Val Pro Asp Ala Asn Val Tyr Asn Ala Met Ile Cys Asn Phe Ile
                325                 330                 335

Ser Ala Arg Asp Phe Asp Glu Ser Met Arg Tyr Tyr Arg Arg Met Leu
            340                 345                 350

Asp Glu Glu Cys Glu Pro Asn Leu Glu Thr Tyr Ser Lys Leu Val Ser
        355                 360                 365

Gly Leu Ile Lys Gly Arg Lys Val Ser Asp Ala Leu Glu Ile Phe Glu
    370                 375                 380

Glu Met Leu Ser Arg Gly Val Leu Pro Thr Thr Gly Leu Val Thr Ser
385                 390                 395                 400

Phe Leu Lys Pro Leu Cys Ser Tyr Gly Pro Pro His Ala Ala Met Val
                405                 410                 415

Ile Tyr Gln Lys Ser Arg Lys Ala Gly Cys Arg Ile Ser Glu Ser Ala
            420                 425                 430

Tyr Lys Leu Leu Leu Lys Arg Leu Ser Arg Phe Gly Lys Cys Gly Met
        435                 440                 445

Leu Leu Asn Val Trp Asp Glu Met Gln Glu Ser Gly Tyr Pro Ser Asp
    450                 455                 460

Val Glu Val Tyr Glu Tyr Ile Val Asp Gly Leu Cys Ile Ile Gly His
465                 470                 475                 480

Leu Glu Asn Ala Val Leu Val Met Glu Glu Ala Met Arg Lys Gly Phe
                485                 490                 495
```

```
Cys Pro Asn Arg Phe Val Tyr Ser Arg Leu Ser Ile Ile Arg Lys Trp
            500                 505                 510

Gln Gln Lys Phe Arg Lys Gly Lys Glu Glu Met Glu Lys Trp Glu Ala
        515                 520                 525

Leu Gln Val Arg Trp Val Ser Leu Phe Arg Asn Ala Ser Ser Ile Ile
    530                 535                 540

Gln Arg Leu Gln Glu Met Gln Asn His Gly Ser Tyr Gly Ala Leu Arg
545                 550                 555                 560

Cys Leu Lys Gly Ile Glu Asp Ala Val Val Gln Gln Gln Met Gly Gln
                565                 570                 575

Leu Glu Ser Leu Leu Arg Ser Met Lys Asn Val Met Glu Glu Phe Trp
            580                 585                 590

Gly Cys Val Leu Thr Phe Glu Lys Leu His Arg Asp Gly Leu Gln Leu
        595                 600                 605

Arg Glu Ile Glu Ser Ser Lys Arg Arg Val Glu Glu Arg Ile Gly Val
    610                 615                 620

Lys Pro Cys Ile Thr Asp Cys Leu Glu Gly Leu Ser Ile Leu Tyr Asp
625                 630                 635                 640

Met His Gln Ser Asp Pro Gly Asp Leu Asn Ala Leu Gln Tyr Leu Val
                645                 650                 655

Val Asp Gln Pro Asn Ile Pro Lys Asp Glu Val Gln His Ile Phe Asp
            660                 665                 670

Val Ile Phe Ala Glu Glu Ile Lys
        675                 680


<210> SEQ ID NO 5
<211> LENGTH: 2589
<212> TYPE: DNA
<213> ORGANISM: Arabidopsis thaliana

<400> SEQUENCE: 5

cgttctaggc cttgattcga ttttgttaac tgttgtaaat gtgaaaaaac aatggcttta     60

aaggcgaaga aaagcttaag cgcgatattt cgctttgcga tgagaaacgc tgccaaaact    120

gccgaagttg aagccaaagc cgtagccgga gattctctga tttcagacac tggaccagtg    180

tcaatgtctt taataccgga ttttctctca tcgcttaagt ctccggaaga ttcttccaac    240

attggtcaag attttggtga accggcactt gcgggtcagg tctcgtctgc gttagatgtt    300

aaatctattg gatataatct tcttcgagaa agaaatggcg agaaagtttt tccgaagaac    360

gtattggaaa ccttagattt actgtctagg aaaggttgtt cgtcgcaaaa gccaaagcag    420

gcttcacgtg gtaggatgct gacagaaaat taccagaaca aacagtctga gattatggag    480

aagcttgcca agggatgtgt tcggaagttg ggaactgaga ctatgtttga ggtgttgact    540

aaaatgggga aagaagcggg tgagaaagaa tacaatgcaa tgactaaact ttgcatacaa    600

cgtgcgagga gaagcaatga tgcagaatat gctcttgatc aaattgggaa ggctattgaa    660

catctcaaag aaatgagaca gcttggattc tctattggag aaggagctta tggccctttt    720

tttaagtact tagttgatat ggaaatggta gcggagttcc aaattctcaa ggattttatt    780

aaggaggcat gtcctgagtc ttgtgggaga cttgtctact atgaaatgct tctttggatc    840

caagtcaacg acgaagagaa gatccacaaa ctttgcaata aagttgatga tagtgggcta    900

agtttatcaa tcctacaaga tggagtggag acagtttcaa atctcatatt cagctatgca    960

acctgcatcc caaattcaac ggtagaggat gccattttca agtttaacaa gttgcatgaa   1020
```

-continued

```
gaactagata tcgtgccttc atctacatct tatgagaatc ttgtcagtta tctttgtggc   1080

tcaaatgagg tggtcactgc tcttgatata gttgaaaata tgtgtgaagc aggtctggta   1140

atatcagcaa acatcctgca ctcattgtta caggccattg agcagattct tgagtttaat   1200

ttggtgcaaa gaatctattc aataatgagc aacaagagtg tgaagccaaa tagtgagact   1260

ttcaggaaat ctataaattt gtgcataaga atcaaagata ctctagcaat gaagtatgaa   1320

tatgctgttt ctcacagaac tttttgttat ccaaccataa caatttgcta tcaacctatt   1380

ggttccgtgc agtttgaagg tgcatataac atgcttggta atttaaagaa tttcaatttg   1440

gcaccgaact ctagcatgta caattctata atggcaggat atttccggga gaaaaaagtg   1500

aacagtgcct taaaggtcct caaggaaatg aaagaagctg atgttaaacc tgattcggtg   1560

acttttagct atctaataaa ctattgtggc gaggaggcga ctattgcgaa gtattataag   1620

gagatgaagc aagcaggagt tgaagttaat aagcacgttt acatgtccct tgttaaagca   1680

tatgcatcat gcggacagtt tgaaaaggca aaacaggtgc tcatggacct ggaagttccg   1740

gctaaggatc acaatgagct gaaaagtgta cttatatctg ctctggcatc aaatggaaat   1800

ataacagagg ctttaagtat ttatgaagaa atgaagaaac tccgctgccc cgtagagcca   1860

aaagctatct tatctcttat agagaactct gattcaaacg cagagctggg aacgttggtt   1920

gaactcactc atgagctgcg tgattctaaa ttttggatag atggtttctt caaaattatc   1980

gtgtttgctg ttcgcaacaa tagatcaagc tctattctgg atttgttaga gcagaccaaa   2040

aaccacttgt ccaaggatga cgtcggtgtg gaatattggt ttgaagaggt gtttaagtca   2100

atagcggaaa cagagtctag tgatgtgaag gtagggctgg acttggtgag ttttatgaaa   2160

gaagagcttg agttatgtcc ttcaagaaaa tgtctggatt ttcttctaca tgcttgtgtc   2220

aatgccaaag ataagcagag cgctctactg gtatgggaag agtaccaatg tgcagaactt   2280

ccttacaatg tcatcaacta tttaaggcaa gagctctttt atctcctaca tttaaaaggg   2340

atgcccgtat tgttcaccgc ctcaaccgct cctgcccagc ttgagtaccc atccaggtca   2400

cagttcaagg ctacaatgat atccggtgaa gtcaggtatg ttacctcgtc ttggtgcaaa   2460

ccttacacaa agctcacctt aactctactg tttgttgttg aggtggttgc tattgtacca   2520

gataagtcag atggaacttc aggtccgatc attatgatct gcacggttcc taaaccatta   2580

agcaagtga                                                            2589
```

<210> SEQ ID NO 6
<211> LENGTH: 845
<212> TYPE: PRT
<213> ORGANISM: Arabidopsis thaliana

<400> SEQUENCE: 6

```
Met Ala Leu Lys Ala Lys Lys Ser Leu Ser Ala Ile Phe Arg Phe Ala
1               5                   10                  15

Met Arg Asn Ala Ala Lys Thr Ala Glu Val Glu Ala Lys Ala Val Ala
            20                  25                  30

Gly Asp Ser Leu Ile Ser Asp Thr Gly Pro Val Ser Met Ser Leu Ile
        35                  40                  45

Pro Asp Phe Leu Ser Ser Leu Lys Ser Pro Glu Asp Ser Ser Asn Ile
    50                  55                  60

Gly Gln Asp Phe Gly Glu Pro Ala Leu Ala Gly Gln Val Ser Ser Ala
65                  70                  75                  80

Leu Asp Val Lys Ser Ile Gly Tyr Asn Leu Leu Arg Glu Arg Asn Gly
                85                  90                  95
```

-continued

```
Glu Lys Val Phe Pro Lys Asn Val Leu Glu Thr Leu Asp Leu Leu Ser
            100                 105                 110

Arg Lys Gly Cys Ser Ser Gln Lys Pro Lys Gln Ala Ser Arg Gly Arg
        115                 120                 125

Met Leu Thr Glu Asn Tyr Gln Asn Lys Gln Ser Glu Ile Met Glu Lys
    130                 135                 140

Leu Ala Lys Gly Cys Val Arg Lys Leu Gly Thr Glu Thr Met Phe Glu
145                 150                 155                 160

Val Leu Thr Lys Met Gly Lys Glu Ala Gly Glu Lys Glu Tyr Asn Ala
                165                 170                 175

Met Thr Lys Leu Cys Ile Gln Arg Ala Arg Arg Ser Asn Asp Ala Glu
            180                 185                 190

Tyr Ala Leu Asp Gln Ile Gly Lys Ala Ile Glu His Leu Lys Glu Met
        195                 200                 205

Arg Gln Leu Gly Phe Ser Ile Gly Glu Gly Ala Tyr Gly Pro Phe Phe
    210                 215                 220

Lys Tyr Leu Val Asp Met Glu Met Val Ala Glu Phe Gln Ile Leu Lys
225                 230                 235                 240

Asp Phe Ile Lys Glu Ala Cys Pro Glu Ser Cys Gly Arg Leu Val Tyr
                245                 250                 255

Tyr Glu Met Leu Leu Trp Ile Gln Val Asn Asp Glu Glu Lys Ile His
            260                 265                 270

Lys Leu Cys Asn Lys Val Asp Asp Ser Gly Leu Ser Leu Ser Ile Leu
        275                 280                 285

Gln Asp Gly Val Glu Thr Val Ser Asn Leu Ile Phe Ser Tyr Ala Thr
    290                 295                 300

Cys Ile Pro Asn Ser Thr Val Glu Asp Ala Ile Phe Lys Phe Asn Lys
305                 310                 315                 320

Leu His Glu Glu Leu Asp Ile Val Pro Ser Ser Thr Ser Tyr Glu Asn
                325                 330                 335

Leu Val Ser Tyr Leu Cys Gly Ser Asn Glu Val Val Thr Ala Leu Asp
            340                 345                 350

Ile Val Glu Asn Met Cys Glu Ala Gly Leu Val Ile Ser Ala Asn Ile
        355                 360                 365

Leu His Ser Leu Leu Gln Ala Ile Glu Gln Ile Leu Glu Phe Asn Leu
    370                 375                 380

Val Gln Arg Ile Tyr Ser Ile Met Ser Asn Lys Ser Val Lys Pro Asn
385                 390                 395                 400

Ser Glu Thr Phe Arg Lys Ser Ile Asn Leu Cys Ile Arg Ile Lys Asp
                405                 410                 415

Thr Leu Ala Met Lys Tyr Glu Tyr Ala Val Ser His Arg Thr Phe Cys
            420                 425                 430

Tyr Pro Thr Ile Thr Ile Cys Tyr Gln Pro Ile Gly Ser Val Gln Phe
        435                 440                 445

Glu Gly Ala Tyr Asn Met Leu Gly Asn Leu Lys Asn Phe Asn Leu Ala
    450                 455                 460

Pro Asn Ser Ser Met Tyr Asn Ser Ile Met Ala Gly Tyr Phe Arg Glu
465                 470                 475                 480

Lys Lys Val Asn Ser Ala Leu Lys Val Leu Lys Glu Met Lys Glu Ala
                485                 490                 495

Asp Val Lys Pro Asp Ser Val Thr Phe Ser Tyr Leu Ile Asn Tyr Cys
            500                 505                 510
```

-continued

```
Gly Glu Glu Ala Thr Ile Ala Lys Tyr Tyr Lys Glu Met Lys Gln Ala
        515                 520                 525

Gly Val Glu Val Asn Lys His Val Tyr Met Ser Leu Val Lys Ala Tyr
    530                 535                 540

Ala Ser Cys Gly Gln Phe Glu Lys Ala Lys Gln Val Leu Met Asp Leu
545                 550                 555                 560

Glu Val Pro Ala Lys Asp His Asn Glu Leu Lys Ser Val Leu Ile Ser
                565                 570                 575

Ala Leu Ala Ser Asn Gly Asn Ile Thr Glu Ala Leu Ser Ile Tyr Glu
            580                 585                 590

Glu Met Lys Lys Leu Arg Cys Pro Val Glu Pro Lys Ala Ile Leu Ser
        595                 600                 605

Leu Ile Glu Asn Ser Asp Ser Asn Ala Glu Leu Gly Thr Leu Val Glu
    610                 615                 620

Leu Thr His Glu Leu Arg Asp Ser Lys Phe Trp Ile Asp Gly Phe Phe
625                 630                 635                 640

Lys Ile Ile Val Phe Ala Val Arg Asn Asn Arg Ser Ser Ser Ile Leu
                645                 650                 655

Asp Leu Leu Glu Gln Thr Lys Asn His Leu Ser Lys Asp Asp Val Gly
            660                 665                 670

Val Glu Tyr Trp Phe Glu Glu Val Phe Lys Ser Ile Ala Glu Thr Glu
        675                 680                 685

Ser Ser Asp Val Lys Val Gly Leu Asp Leu Val Ser Phe Met Lys Glu
    690                 695                 700

Glu Leu Glu Leu Cys Pro Ser Arg Lys Cys Leu Asp Phe Leu Leu His
705                 710                 715                 720

Ala Cys Val Asn Ala Lys Asp Lys Gln Ser Ala Leu Leu Val Trp Glu
                725                 730                 735

Glu Tyr Gln Cys Ala Glu Leu Pro Tyr Asn Val Ile Asn Tyr Leu Arg
            740                 745                 750

Gln Glu Leu Phe Tyr Leu Leu His Leu Lys Gly Met Pro Val Leu Phe
        755                 760                 765

Thr Ala Ser Thr Ala Pro Ala Gln Leu Glu Tyr Pro Ser Arg Ser Gln
    770                 775                 780

Phe Lys Ala Thr Met Ile Ser Gly Glu Val Arg Tyr Val Thr Ser Ser
785                 790                 795                 800

Trp Cys Lys Pro Tyr Thr Lys Leu Thr Leu Thr Leu Leu Phe Val Val
                805                 810                 815

Glu Val Val Ala Ile Val Pro Asp Lys Ser Asp Gly Thr Ser Gly Pro
            820                 825                 830

Ile Ile Met Ile Cys Thr Val Pro Lys Pro Leu Ser Lys
        835                 840                 845


<210> SEQ ID NO 7
<211> LENGTH: 1839
<212> TYPE: DNA
<213> ORGANISM: Arabidopsis thaliana

<400> SEQUENCE: 7

atgggttttg aagatggacc aagatgtctt atgtctcatc cagctcaccc ttctcataac      60

ttgtccgttc gatacagatt caactttcgt atcggttgct ttacatgtgg cgggaaagca     120

gctgctacga cgccggattg tctctactac tactgcacca cctgcgaggt gacgttccac     180

aatggttgcc atcaacgtcc aagaaggata acacatcctt atcacctcca acatcctctt     240
```

-continued

```
actctcttct atcgaaaccc cgaaaccaga gttatatcca acatcatccc tgatgcttgt    300

cctggtaaaa ttgaggatac atcaggtcca gagaagtatg aattcgtgga tatcgtcccg    360

tataagtctg atatcatatt caacaaatgc acttggtgtg caaaagattt caaaggtgat    420

tggttttatc gttgtttgat ctgtagtttt tgcttggatc tctcttgtgc ggcaactctt    480

ccacttctta ctattacaaa cccgaaaagc catcaccact ctctcgtctt cttacccccgg    540

ccattattag ttccatgtga tgcttgtggg ttggttgacg ggttggaacc aagttatgct    600

tgtttccaat gtaattacat ggttcatcag aattgcatag acttaccccg agtcataaaa    660

atcacgcgtc acccgcaccg gctctctcat actccttatt gttcatcttt gacttcgtca    720

tgccaaatct gctataaaga ggttgatatc aagtatgggc aatattcttg ccatctccaa    780

gattgttttt atgtagtcca ttctaaatgt gcaacacatg aaaatgtttg ggatgggaag    840

gaactcgagt gggaaatcga gtctgatgaa actgaagata tttcaccttt taggaaccta    900

ggtgatggtt tcataaagca tttttgtcac aaacaccgtt tgaagctcaa gaatcatgat    960

ggtgctcgag acacagaaaa gcaatgtcga gcgtgcatat atccaattgt ttctcaccaa   1020

ttttaccatt gcaagaaatg caattactct ctccacgagg tatgtgctgg cctttctcga   1080

aaactggatc atgcattgca caatcacact cttatcctat ctccatctcc cggaaagttt   1140

tgttgttcag cttgttcccg agaatccact ggtttcagtt acatatgctc taataaaggt   1200

tgccaagatt ttgttctaga tgttcgatgc atctcagtgc tagagtattt catccataga   1260

agtcacgaac atcccatttt tatctccaca tcctacaaca gtaaagacga gatcctctgc   1320

aaagtttgca agaaaaagatg tttgggggct catctacagt gtacgttatg cgagtttact   1380

atgtgttact catgtgctat cattccagat gaaatacact acaaatttga caagcatcct   1440

ctcacccttt cttgtgggga aagcgcggat aacacgtatt ggtgcgaggt gtgtgaaaaa   1500

caattggatc caaaagaatg gttctacaca tgtaacaaat gttgcatcac catccacctt   1560

cattgcatat ttggatcttc tgtctttatg aaacctggtt ccatatttcg tgattattat   1620

ggaaaggtgc aagtttttcg aaacaatagt aacactcgac aactctgtta tatgtgtcac   1680

aaccgttgta ccggtttgat cttctacgaa ggctacagaa ggaatgctac atattactac   1740

aatcatagca atcgatcaac tcatagaatg attttttgct ctttggaatg tgagatatta   1800

gggatgagaa aacgtcgtct catccgtctt ccgaggtaa                          1839
```

<210> SEQ ID NO 8
<211> LENGTH: 612
<212> TYPE: PRT
<213> ORGANISM: Arabidopsis thaliana

<400> SEQUENCE: 8

```
Met Gly Phe Glu Asp Gly Pro Arg Cys Leu Met Ser His Pro Ala His
1               5                   10                  15

Pro Ser His Asn Leu Ser Val Arg Tyr Arg Phe Asn Phe Arg Ile Gly
            20                  25                  30

Cys Phe Thr Cys Gly Gly Lys Ala Ala Ala Thr Thr Pro Asp Cys Leu
        35                  40                  45

Tyr Tyr Tyr Cys Thr Thr Cys Glu Val Thr Phe His Asn Gly Cys His
    50                  55                  60

Gln Arg Pro Arg Arg Ile Thr His Pro Tyr His Leu Gln His Pro Leu
65                  70                  75                  80

Thr Leu Phe Tyr Arg Asn Pro Glu Thr Arg Val Ile Ser Asn Ile Ile
                85                  90                  95
```

-continued

```
Pro Asp Ala Cys Pro Gly Lys Ile Glu Asp Thr Ser Gly Pro Glu Lys
            100                 105                 110

Tyr Glu Phe Val Asp Ile Val Pro Tyr Lys Ser Asp Ile Ile Phe Asn
        115                 120                 125

Lys Cys Thr Trp Cys Ala Lys Asp Phe Lys Gly Asp Trp Phe Tyr Arg
    130                 135                 140

Cys Leu Ile Cys Ser Phe Cys Leu Asp Leu Ser Cys Ala Ala Thr Leu
145                 150                 155                 160

Pro Leu Leu Thr Ile Thr Asn Pro Lys Ser His His His Ser Leu Val
                165                 170                 175

Phe Leu Pro Arg Pro Leu Leu Val Pro Cys Asp Ala Cys Gly Leu Val
            180                 185                 190

Asp Gly Leu Glu Pro Ser Tyr Ala Cys Phe Gln Cys Asn Tyr Met Val
        195                 200                 205

His Gln Asn Cys Ile Asp Leu Pro Arg Val Ile Lys Ile Thr Arg His
    210                 215                 220

Pro His Arg Leu Ser His Thr Pro Tyr Cys Ser Ser Leu Thr Ser Ser
225                 230                 235                 240

Cys Gln Ile Cys Tyr Lys Glu Val Asp Ile Lys Tyr Gly Gln Tyr Ser
                245                 250                 255

Cys His Leu Gln Asp Cys Phe Tyr Val Val His Ser Lys Cys Ala Thr
            260                 265                 270

His Glu Asn Val Trp Asp Gly Lys Glu Leu Glu Trp Glu Ile Glu Ser
        275                 280                 285

Asp Glu Thr Glu Asp Ile Ser Pro Phe Arg Asn Leu Gly Asp Gly Phe
    290                 295                 300

Ile Lys His Phe Cys His Lys His Arg Leu Lys Leu Lys Asn His Asp
305                 310                 315                 320

Gly Ala Arg Asp Thr Glu Lys Gln Cys Arg Ala Cys Ile Tyr Pro Ile
                325                 330                 335

Val Ser His Gln Phe Tyr His Cys Lys Lys Cys Asn Tyr Ser Leu His
            340                 345                 350

Glu Val Cys Ala Gly Leu Ser Arg Lys Leu Asp His Ala Leu His Asn
        355                 360                 365

His Thr Leu Ile Leu Ser Pro Ser Pro Gly Lys Phe Cys Cys Ser Ala
    370                 375                 380

Cys Ser Arg Glu Ser Thr Gly Phe Ser Tyr Ile Cys Ser Asn Lys Gly
385                 390                 395                 400

Cys Gln Asp Phe Val Leu Asp Val Arg Cys Ile Ser Val Leu Glu Tyr
                405                 410                 415

Phe Ile His Arg Ser His Glu His Pro Ile Phe Ile Ser Thr Ser Tyr
            420                 425                 430

Asn Ser Lys Asp Glu Ile Leu Cys Lys Val Cys Lys Lys Arg Cys Leu
        435                 440                 445

Gly Ala His Leu Gln Cys Thr Leu Cys Glu Phe Thr Met Cys Tyr Ser
    450                 455                 460

Cys Ala Ile Ile Pro Asp Glu Ile His Tyr Lys Phe Asp Lys His Pro
465                 470                 475                 480

Leu Thr Leu Ser Cys Gly Glu Ser Ala Asp Asn Thr Tyr Trp Cys Glu
                485                 490                 495

Val Cys Glu Lys Gln Leu Asp Pro Lys Glu Trp Phe Tyr Thr Cys Asn
            500                 505                 510
```

```
Lys Cys Cys Ile Thr Ile His Leu His Cys Ile Phe Gly Ser Ser Val
        515                 520                 525

Phe Met Lys Pro Gly Ser Ile Phe Arg Asp Tyr Tyr Gly Lys Val Gln
    530                 535                 540

Val Phe Arg Asn Asn Ser Asn Thr Arg Gln Leu Cys Tyr Met Cys His
545                 550                 555                 560

Asn Arg Cys Thr Gly Leu Ile Phe Tyr Glu Gly Tyr Arg Arg Asn Ala
                565                 570                 575

Thr Tyr Tyr Tyr Asn His Ser Asn Arg Ser Thr His Arg Met Ile Phe
            580                 585                 590

Cys Ser Leu Glu Cys Glu Ile Leu Gly Met Arg Lys Arg Arg Leu Ile
        595                 600                 605

Arg Leu Pro Arg
    610


<210> SEQ ID NO 9
<211> LENGTH: 2037
<212> TYPE: DNA
<213> ORGANISM: Arabidopsis thaliana

<400> SEQUENCE: 9

tgttcccttt ggagggttct tctcatcaac atcaaatttc agagttccat tgagtagcac     60

agtgaatcag acgctctcta gatgccacct ctgcaacgag aagtatttgc aagaagtagc    120

cgctgttctc aaggccggtt cgagtctttc tctggctgac aaatgttccg agaagttagc    180

cccatggcta cgggctattg agaccaaaga agacaaggga ataacaggca gcagtaagtg    240

caggctttag atgacgctaa tacatcagcc tcgcaaaccg ctgctctaca gaagaaatgg    300

gacaacatat gccaaagtat ccatcacact ccggcgtttc ctaaacttgg ttttcagtcg    360

gtgagtccgc agttcccagt tcagactgag aagagtgtga gaactcctac aagctatttg    420

gagacgccta aactgctgaa tccgccaatc tcaaagccaa aacctatgga ggatcttacg    480

gcatcggtga ctaaccgcac agtgagtttg cctttgagct gtgttactac agattttggg    540

ttgggagtaa tctatgcatc caaaaaccag gaatcaaaaa caacgaggga gaaaccgatg    600

ctggtgactc taaactcttc tttagaacat acatatcaga aagatttcaa gtctctcaga    660

gaaatactct ctcgtaaagt tgcctggcag accgaagctg taaatgccat aagccaaatt    720

atctgcggat gcaaaaccga ctccacgcga agaaaccaag caagcggaat ttggctggct    780

cttcttggac ccgataaagt ggggaagaag aaagtggcga tgactctttc tgaagtcttc    840

tttggtggta aagtcaatta catatgtgta gattttgggg cagagcattg ttcccttgat    900

gacaaattca gaggcaaaac agtggtggat tacgtaaccg gtgagttatc taggaaacca    960

cactctgttg ttttactcga aaacgtggaa aaagctgagt tcccggatca gatgagattg   1020

tctgaagctg tgagtacggg gaaaatccgt gatttgcatg gaagagtgat tagtatgaaa   1080

aatgtgattg ttgttgtgac gtctgggatt gccaaggata atgccactga ccatgttatt   1140

aaacctgtga agtttcctga ggagcaagtt ctcagcgcga gaagctggaa actgcagata   1200

aagctaggag atgctactaa atttggggta aataagagaa aatatgagct agaaacagcg   1260

caacgtgcag tgaaggtgca acgttcatat ctggatctga atcttccagt gaatgaaaca   1320

gaatttagcc ctgatcatga ggcagaggac agggacgctt ggttcgatga attcattgaa   1380

aaagtagatg gaaaagtgac gttcaaaccg gttgatttcg atgagttagc caagaacatt   1440

caagagaaga ttggttcaca ttttgagcgg tgctttggat ccgaaacaca tctagaactt   1500
```

-continued

```
gataaagaag tgatccttca gattctggcg gcttcatggt catcattatc atcgggcgaa   1560

gaagaaggga gaacaatagt tgatcagtgg atgcaaacag ttcttgctcg aagctttgct   1620

gaagcaaaac agaagtacgg ttcgaatccc atgttgggcg tgaagctggt tgcttcttct   1680

agcggcttag cttccggagt agaattgccg gcgaaggtgg atgtgatatg gtgacatgca   1740

tatatataaa tgaggtaata ataaagagtt ataatcctca gattgttttt ctcatggaaa   1800

gtttttgct tgtgtaaatt acaatgtaaa atggctaagc tatcacttgg tagataggtt    1860

tgtttaggag taccaatttg ccacatcttt tttggcattt tgagttttag gtatttctcc   1920

taaaattttc cccaacttcc aaatttagat gaattaaacc atcttctctg taaccgagtt   1980

tgttgtatat tatgttacgt ttgtcgaaat atagaaacga tgctttccac gccgatc      2037


<210> SEQ ID NO 10
<211> LENGTH: 422
<212> TYPE: PRT
<213> ORGANISM: Arabidopsis thaliana

<400> SEQUENCE: 10

Met Glu Asp Leu Thr Ala Ser Val Thr Asn Arg Thr Val Ser Leu Pro
1               5                   10                  15

Leu Ser Cys Val Thr Thr Asp Phe Gly Leu Gly Val Ile Tyr Ala Ser
            20                  25                  30

Lys Asn Gln Glu Ser Lys Thr Thr Arg Glu Lys Pro Met Leu Val Thr
        35                  40                  45

Leu Asn Ser Ser Leu Glu His Thr Tyr Gln Lys Asp Phe Lys Ser Leu
    50                  55                  60

Arg Glu Ile Leu Ser Arg Lys Val Ala Trp Gln Thr Glu Ala Val Asn
65                  70                  75                  80

Ala Ile Ser Gln Ile Ile Cys Gly Cys Lys Thr Asp Ser Thr Arg Arg
                85                  90                  95

Asn Gln Ala Ser Gly Ile Trp Leu Ala Leu Leu Gly Pro Asp Lys Val
            100                 105                 110

Gly Lys Lys Lys Val Ala Met Thr Leu Ser Glu Val Phe Phe Gly Gly
        115                 120                 125

Lys Val Asn Tyr Ile Cys Val Asp Phe Gly Ala Glu His Cys Ser Leu
    130                 135                 140

Asp Asp Lys Phe Arg Gly Lys Thr Val Val Asp Tyr Val Thr Gly Glu
145                 150                 155                 160

Leu Ser Arg Lys Pro His Ser Val Val Leu Leu Glu Asn Val Glu Lys
                165                 170                 175

Ala Glu Phe Pro Asp Gln Met Arg Leu Ser Glu Ala Val Ser Thr Gly
            180                 185                 190

Lys Ile Arg Asp Leu His Gly Arg Val Ile Ser Met Lys Asn Val Ile
        195                 200                 205

Val Val Val Thr Ser Gly Ile Ala Lys Asp Asn Ala Thr Asp His Val
    210                 215                 220

Ile Lys Pro Val Lys Phe Pro Glu Glu Gln Val Leu Ser Ala Arg Ser
225                 230                 235                 240

Trp Lys Leu Gln Ile Lys Leu Gly Asp Ala Thr Lys Phe Gly Val Asn
                245                 250                 255

Lys Arg Lys Tyr Glu Leu Glu Thr Ala Gln Arg Ala Val Lys Val Gln
            260                 265                 270

Arg Ser Tyr Leu Asp Leu Asn Leu Pro Val Asn Glu Thr Glu Phe Ser
        275                 280                 285
```

-continued

```
Pro Asp His Glu Ala Glu Asp Arg Asp Ala Trp Phe Asp Glu Phe Ile
    290                 295                 300

Glu Lys Val Asp Gly Lys Val Thr Phe Lys Pro Val Asp Phe Asp Glu
305                 310                 315                 320

Leu Ala Lys Asn Ile Gln Glu Lys Ile Gly Ser His Phe Glu Arg Cys
                325                 330                 335

Phe Gly Ser Glu Thr His Leu Glu Leu Asp Lys Glu Val Ile Leu Gln
            340                 345                 350

Ile Leu Ala Ala Ser Trp Ser Ser Leu Ser Ser Gly Glu Glu Glu Gly
        355                 360                 365

Arg Thr Ile Val Asp Gln Trp Met Gln Thr Val Leu Ala Arg Ser Phe
    370                 375                 380

Ala Glu Ala Lys Gln Lys Tyr Gly Ser Asn Pro Met Leu Gly Val Lys
385                 390                 395                 400

Leu Val Ala Ser Ser Ser Gly Leu Ala Ser Gly Val Glu Leu Pro Ala
                405                 410                 415

Lys Val Asp Val Ile Trp
            420


<210> SEQ ID NO 11
<211> LENGTH: 1496
<212> TYPE: DNA
<213> ORGANISM: Arabidopsis thaliana

<400> SEQUENCE: 11

tgaaaagttc aaatctttgt tttgaaaact ctcaaagtgt taatcttttg tagctgtttc      60

catttttga agcagaataa cagagagatt acatgttgtg tgtgtttaga aggaagcttg     120

gttgcctttt ttcaagactt agatgggtta tcaagaaacg ggtgagggct agagttatag     180

tcaggaggtt caggaaagca aggtggagag ctcgaagaaa agagagtccg gaatctgaag     240

tttcttctat ccatctgagc tcaaactctg gaagacatat tcgggttgca acgtttaacg     300

tggctatgtt ctcacttgcg cctgttgtgc aaaccatgga ggaaacagct tttcttggtc     360

atctagatag cagcaacatc acatgccctt ctccaaaagg gattctgaag cagtctccat     420

tacattcttc tgcagtcagg aaaccaaagg tttgcattaa tctcccagac aatgagattt     480

ccttagcaca gagctacagc tttctgagta tggtagagaa tgataacgac gggaaggaaa     540

acagaggaag tctctcgatg agatctcccg tgtgtcttcc ctcttgttgg tgggaccaag     600

aaagctttaa cggatacagc agcagaagaa gcatagctga attgttaaga gagttggatg     660

cagacatctt ggctttacaa gacgtgaaag cagaggaaga gacacttatg aaaccattat     720

cagatttggc ttccgcctta ggtatgaaat acgtgtttgc agagagctgg gcgcctgagt     780

atggaaacgc catactatca aaatggccca taaagaagtg gagagttcag agaattgctg     840

atgtagatga ttttaggaat gtgttgaagg tgactgtaga gatcccatgg gctggagatg     900

taaatgtgta ttgtactcaa cttgaccatc tagatgagaa ctggcgtatg aagcagatcg     960

atgcaattac tcgaggagac gaatctcccc acatcctcct tggaggcttg aattctcttg    1020

atggctctga ttattccata gcaagatgga accacatcgt aaagtattac gaggattctg    1080

gaaagccgac gcctagagtt gaagtgatga ggtttctcaa gggaaaagga tacttggatt    1140

caaaagaatt tgcaggagaa tgtgagcctg tagtcattat tgccaaagga caaaatgtac    1200

aaggaacatg caagtacggg acacgggtcg attacattct ggcatctcca gagtcacctt    1260

acgaatttgt tcctggctcg tactcagttg tttcttccaa aggtacttct gatcatcata    1320
```

-continued tagtcaaagt cgatttagtt ataaccaaag agcgatctcg aggtaacttc aaacattcac 1380
gcaagaaagc aaagcagaag atctttcaga taaaagctaa tttgatgtcg aaagatacat 1440
ggaaactagg aaatctgatg tcttcataaa gtttggacac tgattaagaa acaaca 1496

<210> SEQ ID NO 12
<211> LENGTH: 458
<212> TYPE: PRT
<213> ORGANISM: Arabidopsis thaliana

<400> SEQUENCE: 12

Met Leu Cys Val Phe Arg Arg Lys Leu Gly Cys Leu Phe Ser Arg Leu
1 5 10 15

Arg Trp Val Ile Lys Lys Arg Val Arg Ala Arg Val Ile Val Arg Arg
20 25 30

Phe Arg Lys Ala Arg Trp Arg Ala Arg Arg Lys Glu Ser Pro Glu Ser
35 40 45

Glu Val Ser Ser Ile His Leu Ser Ser Asn Ser Gly Arg His Ile Arg
50 55 60

Val Ala Thr Phe Asn Val Ala Met Phe Ser Leu Ala Pro Val Val Gln
65 70 75 80

Thr Met Glu Glu Thr Ala Phe Leu Gly His Leu Asp Ser Ser Asn Ile
85 90 95

Thr Cys Pro Ser Pro Lys Gly Ile Leu Lys Gln Ser Pro Leu His Ser
100 105 110

Ser Ala Val Arg Lys Pro Lys Val Cys Ile Asn Leu Pro Asp Asn Glu
115 120 125

Ile Ser Leu Ala Gln Ser Tyr Ser Phe Leu Ser Met Val Glu Asn Asp
130 135 140

Asn Asp Gly Lys Glu Asn Arg Gly Ser Leu Ser Met Arg Ser Pro Val
145 150 155 160

Cys Leu Pro Ser Cys Trp Trp Asp Gln Glu Ser Phe Asn Gly Tyr Ser
165 170 175

Ser Arg Arg Ser Ile Ala Glu Leu Leu Arg Glu Leu Asp Ala Asp Ile
180 185 190

Leu Ala Leu Gln Asp Val Lys Ala Glu Glu Glu Thr Leu Met Lys Pro
195 200 205

Leu Ser Asp Leu Ala Ser Ala Leu Gly Met Lys Tyr Val Phe Ala Glu
210 215 220

Ser Trp Ala Pro Glu Tyr Gly Asn Ala Ile Leu Ser Lys Trp Pro Ile
225 230 235 240

Lys Lys Trp Arg Val Gln Arg Ile Ala Asp Val Asp Asp Phe Arg Asn
245 250 255

Val Leu Lys Val Thr Val Glu Ile Pro Trp Ala Gly Asp Val Asn Val
260 265 270

Tyr Cys Thr Gln Leu Asp His Leu Asp Glu Asn Trp Arg Met Lys Gln
275 280 285

Ile Asp Ala Ile Thr Arg Gly Asp Glu Ser Pro His Ile Leu Leu Gly
290 295 300

Gly Leu Asn Ser Leu Asp Gly Ser Asp Tyr Ser Ile Ala Arg Trp Asn
305 310 315 320

His Ile Val Lys Tyr Tyr Glu Asp Ser Gly Lys Pro Thr Pro Arg Val
325 330 335

Glu Val Met Arg Phe Leu Lys Gly Lys Gly Tyr Leu Asp Ser Lys Glu

```
            340                 345                 350

Phe Ala Gly Glu Cys Glu Pro Val Val Ile Ile Ala Lys Gly Gln Asn
        355                 360                 365

Val Gln Gly Thr Cys Lys Tyr Gly Thr Arg Val Asp Tyr Ile Leu Ala
    370                 375                 380

Ser Pro Glu Ser Pro Tyr Glu Phe Val Pro Gly Ser Tyr Ser Val Val
385                 390                 395                 400

Ser Ser Lys Gly Thr Ser Asp His His Ile Val Lys Val Asp Leu Val
                405                 410                 415

Ile Thr Lys Glu Arg Ser Arg Gly Asn Phe Lys His Ser Arg Lys Lys
            420                 425                 430

Ala Lys Gln Lys Ile Phe Gln Ile Lys Ala Asn Leu Met Ser Lys Asp
        435                 440                 445

Thr Trp Lys Leu Gly Asn Leu Met Ser Ser
    450                 455


<210> SEQ ID NO 13
<211> LENGTH: 1502
<212> TYPE: DNA
<213> ORGANISM: Arabidopsis thaliana

<400> SEQUENCE: 13

tcctcattca tctctaacaa tggcgtcttc tcgaatcatc atcttctccg ttcttcttct      60

ctccatcttc tcactctcat catctgccca accatctttc cgccccaaag ctctccttct     120

cccagtaaca aaagacccat ctaccctcca gtacacaacc gtcatcaacc aacgcacacc     180

tctcgtcccc gcttccgtcg tattcgacct cggtggtcga gaattctggg tcgactgtga     240

ccaaggctac gtctccacca cttaccgctc tcctcgctgc aactccgctg tctgctcacg     300

cgccggctcc atcgcctgcg gcacatgctt ctctcctccg agacctggct gtagtaacaa     360

cacttgcggc gcttttccag ataactccat caccggatgg gcaacctcgg gcgaatttgc     420

tttagacgtt gtgtctatcc agtccactaa cggatccaat ccgggtcggt tcgttaaaat     480

ccccaatcta atattcagtt gcggatcaac gtctcttctt aaaggactcg ctaaaggagc     540

cgttggtatg gctggaatgg gacgtcacaa catcggctta ccgttgcagt tcgccgccgc     600

gtttagcttc aaccgcaaat tcgccgtgtg tcttacttcc ggtagaggcg tcgccttctt     660

cggcaacgga ccttacgttt tcctccccgg gatccagatc tcaaggcttc aaaagacacc     720

gcttctcatc aatccaggga ccactgtttt tgagttttca aaaggcgaga agtcgccgga     780

gtattttatc ggcgtgacgg cgattaagat cgtcgagaaa acacttccaa tcgatccaac     840

gcttttgaag ataaacgcaa gtactggaat aggaggaacc aaaatcagct ccgtcaatcc     900

ttacacggtg ttggagtcat cgatctacaa agcttttacg tcggagttta ttagacaagc     960

agcggcgagg agcatcaaga gagtagcgtc ggtgaaaccg ttcggcgcgt gtttcagcac    1020

gaagaacgtt ggcgtcacgc gcctaggata cgccgtaccg gagattcagc tcgtgcttca    1080

tagcaaagac gtcgtttgga gaatctttgg agctaactcg atggtgagtg tcagtgatga    1140

cgtcatctgt ttgggtttcg ttgacggagg agtcaaccca ggagcctctg tggtgatcgg    1200

agggttccag ttggaggata atttgatcga atttgatttg gcgagtaaca aatttgggtt    1260

tagttccacg ttattgggcc gtcaaactaa ctgcgccaac tttaatttca cttccactgc    1320

ttgattaaat ttagttgatg cactttctcc aaaataaatg tgtttcagta acactaaata    1380

aatgtattgt attatgttta atttgatcag gagccaatgg aatcatttct aagcattttt    1440
```

```
atcacttgat ctgaataatt atgtaatgag tgagtatttg attttaaaaa tttaaattta   1500

gc                                                                   1502


<210> SEQ ID NO 14
<211> LENGTH: 434
<212> TYPE: PRT
<213> ORGANISM: Arabidopsis thaliana

<400> SEQUENCE: 14

Met Ala Ser Ser Arg Ile Ile Ile Phe Ser Val Leu Leu Leu Ser Ile
1               5                   10                  15

Phe Ser Leu Ser Ser Ser Ala Gln Pro Ser Phe Arg Pro Lys Ala Leu
            20                  25                  30

Leu Leu Pro Val Thr Lys Asp Pro Ser Thr Leu Gln Tyr Thr Thr Val
        35                  40                  45

Ile Asn Gln Arg Thr Pro Leu Val Pro Ala Ser Val Val Phe Asp Leu
    50                  55                  60

Gly Gly Arg Glu Phe Trp Val Asp Cys Asp Gln Gly Tyr Val Ser Thr
65                  70                  75                  80

Thr Tyr Arg Ser Pro Arg Cys Asn Ser Ala Val Cys Ser Arg Ala Gly
                85                  90                  95

Ser Ile Ala Cys Gly Thr Cys Phe Ser Pro Pro Arg Pro Gly Cys Ser
            100                 105                 110

Asn Asn Thr Cys Gly Ala Phe Pro Asp Asn Ser Ile Thr Gly Trp Ala
        115                 120                 125

Thr Ser Gly Glu Phe Ala Leu Asp Val Val Ser Ile Gln Ser Thr Asn
    130                 135                 140

Gly Ser Asn Pro Gly Arg Phe Val Lys Ile Pro Asn Leu Ile Phe Ser
145                 150                 155                 160

Cys Gly Ser Thr Ser Leu Leu Lys Gly Leu Ala Lys Gly Ala Val Gly
                165                 170                 175

Met Ala Gly Met Gly Arg His Asn Ile Gly Leu Pro Leu Gln Phe Ala
            180                 185                 190

Ala Ala Phe Ser Phe Asn Arg Lys Phe Ala Val Cys Leu Thr Ser Gly
        195                 200                 205

Arg Gly Val Ala Phe Phe Gly Asn Gly Pro Tyr Val Phe Leu Pro Gly
    210                 215                 220

Ile Gln Ile Ser Arg Leu Gln Lys Thr Pro Leu Leu Ile Asn Pro Gly
225                 230                 235                 240

Thr Thr Val Phe Glu Phe Ser Lys Gly Glu Lys Ser Pro Glu Tyr Phe
                245                 250                 255

Ile Gly Val Thr Ala Ile Lys Ile Val Glu Lys Thr Leu Pro Ile Asp
            260                 265                 270

Pro Thr Leu Leu Lys Ile Asn Ala Ser Thr Gly Ile Gly Gly Thr Lys
        275                 280                 285

Ile Ser Ser Val Asn Pro Tyr Thr Val Leu Glu Ser Ser Ile Tyr Lys
    290                 295                 300

Ala Phe Thr Ser Glu Phe Ile Arg Gln Ala Ala Ala Arg Ser Ile Lys
305                 310                 315                 320

Arg Val Ala Ser Val Lys Pro Phe Gly Ala Cys Phe Ser Thr Lys Asn
                325                 330                 335

Val Gly Val Thr Arg Leu Gly Tyr Ala Val Pro Glu Ile Gln Leu Val
            340                 345                 350

Leu His Ser Lys Asp Val Val Trp Arg Ile Phe Gly Ala Asn Ser Met
```

```
        355                 360                 365

Val Ser Val Ser Asp Asp Val Ile Cys Leu Gly Phe Val Asp Gly Gly
    370                 375                 380

Val Asn Pro Gly Ala Ser Val Val Ile Gly Gly Phe Gln Leu Glu Asp
385                 390                 395                 400

Asn Leu Ile Glu Phe Asp Leu Ala Ser Asn Lys Phe Gly Phe Ser Ser
                405                 410                 415

Thr Leu Leu Gly Arg Gln Thr Asn Cys Ala Asn Phe Asn Phe Thr Ser
            420                 425                 430

Thr Ala


<210> SEQ ID NO 15
<211> LENGTH: 2238
<212> TYPE: DNA
<213> ORGANISM: Arabidopsis thaliana

<400> SEQUENCE: 15

atgattacaa gcttatctca aatctctttt gggacattga ggcgctttgg ctcttctgtt      60

ttaccttctg cactgaaacg cgaatttgtt gaaggattgc gtacgttagt aaggtctggt     120

gatatccgtc gagctgtttc cttattctat tctgcgccgg tcgagcttca gtctcaacag     180

gcttacgcag ctctgttcca agcatgtgca gagcaacgca atctcctcga tggaatcaac     240

ttgcaccacc acatgctctc acatccctat tgttattcac agaacgttat acttgctaat     300

ttcctcatta atatgtatgc caaatgtggg aatatcttat acgcacgaca ggtgtttgat     360

acaatgcctg agaggaatgt tgtttcatgg actgcattga tcacaggcta tgtacaggct     420

gggaatgagc aagagggatt ctgtcttttc tcgtctatgt tatcccattg tttccctaac     480

gagtttacgc tgtcaagcgt gttaacttca tgtcgatatg agcctggaaa gcaggtacat     540

ggacttgctc tgaaacttgg tttacattgt tcgatctatg tggcgaatgc agttatctct     600

atgtacggta ggtgtcatga tggtgccgca gcatatgaag cttggactgt gtttgaagcc     660

ataaagttta agaatttggt tacttggaac tcaatgattg ctgcttttca gtgctgcaat     720

cttgggaaaa aggccattgg cgtttttatg cggatgcata gtgatggagt gggatttgat     780

cgtgccacgt tgcttaatat atgttcttcc ttgtacaaaa gctctgactt agttcctaat     840

gaggtttcaa agtgttgtct tcaactgcat tctctgactg taaaatccgg gttggtgact     900

cagactgaag tggctactgc attgattaaa gtttattcag aaatgttaga agactatact     960

gactgctaca agctttttat ggaaatgagt cactgcaggg acattgttgc ttggaatggg    1020

attataacag cgtttgcagt gtatgatccg gagagagcta ttcatctctt tggtcagtta    1080

cgtcaggaga agctaagccc tgactggtat actttctcaa gtgtactaaa agcttgtgca    1140

ggacttgtca ctgctcgcca tgctttgtct atacacgctc aagtgatcaa gggtggtttt    1200

ttggctgaca cggtgctgaa caactcatta atccatgcgt atgccaagtg tggctctctt    1260

gacttgtgta tgcgtgtatt tgacgatatg gattcgcggg atgttgtttc ctggaactca    1320

atgctcaagg cttactcatt acatggccaa gtagactcaa ttctaccagt ctttcagaaa    1380

atggacatca accccgattc agcgactttc atagcccttc tctcggcttg cagccacgca    1440

ggacgagtag aagaaggatt gagaatattc agatccatgt ttgagaaacc tgaaactctt    1500

cctcagctaa atcactacgc ttgtgtgatc gatatgctaa gccgagctga gcgttttgct    1560

gaggcagaag aggttatcaa gcagatgcca atggacccag atgctgtagt ttggattgca    1620

ttattgggat catgtagaaa gcacggtaac acccggttgg gtaagttagc ggcagataaa    1680
```

-continued

```
cttaaagagc tagtcgaacc cacaaactca atgagttaca tccagatgtc aaacatatac   1740

aacgcagaag gtagctttaa cgaagccaat cttagcataa aggagatgga aacatggaga   1800

gtacggaaag aaccagactt aagctggaca gagataggaa acaaggttca cgaattcgca   1860

tcgggaggaa gacaccgtcc ggacaaggaa gccgtataca gagaattgaa gagactgatt   1920

agttggttaa aggagatggg ttacgttcca gaaatgaggt cagcttcaca agatatagaa   1980

gacgaagaac aggaggaaga taatttatta catcacagcg agaaacttgc gttagcgttt   2040

gcggttatgg agggaagaaa atcgagtgat tgtggtgtga atttgataca gattatgaag   2100

aacacaagga tctgtattga ttgccataac ttcatgaaat tagcttctaa gcttttggga   2160

aaagagattc ttatgagaga ctcgaatcgg tttcaccatt tcaaagattc ttcttgctcc   2220

tgtaatgact actggtaa                                                 2238
```

```
<210> SEQ ID NO 16
<211> LENGTH: 745
<212> TYPE: PRT
<213> ORGANISM: Arabidopsis thaliana

<400> SEQUENCE: 16

Met Ile Thr Ser Leu Ser Gln Ile Ser Phe Gly Thr Leu Arg Arg Phe
1               5                   10                  15

Gly Ser Ser Val Leu Pro Ser Ala Leu Lys Arg Glu Phe Val Glu Gly
            20                  25                  30

Leu Arg Thr Leu Val Arg Ser Gly Asp Ile Arg Arg Ala Val Ser Leu
        35                  40                  45

Phe Tyr Ser Ala Pro Val Glu Leu Gln Ser Gln Gln Ala Tyr Ala Ala
    50                  55                  60

Leu Phe Gln Ala Cys Ala Glu Gln Arg Asn Leu Leu Asp Gly Ile Asn
65                  70                  75                  80

Leu His His His Met Leu Ser His Pro Tyr Cys Tyr Ser Gln Asn Val
                85                  90                  95

Ile Leu Ala Asn Phe Leu Ile Asn Met Tyr Ala Lys Cys Gly Asn Ile
            100                 105                 110

Leu Tyr Ala Arg Gln Val Phe Asp Thr Met Pro Glu Arg Asn Val Val
        115                 120                 125

Ser Trp Thr Ala Leu Ile Thr Gly Tyr Val Gln Ala Gly Asn Glu Gln
    130                 135                 140

Glu Gly Phe Cys Leu Phe Ser Ser Met Leu Ser His Cys Phe Pro Asn
145                 150                 155                 160

Glu Phe Thr Leu Ser Ser Val Leu Thr Ser Cys Arg Tyr Glu Pro Gly
                165                 170                 175

Lys Gln Val His Gly Leu Ala Leu Lys Leu Gly Leu His Cys Ser Ile
            180                 185                 190

Tyr Val Ala Asn Ala Val Ile Ser Met Tyr Gly Arg Cys His Asp Gly
        195                 200                 205

Ala Ala Ala Tyr Glu Ala Trp Thr Val Phe Glu Ala Ile Lys Phe Lys
    210                 215                 220

Asn Leu Val Thr Trp Asn Ser Met Ile Ala Ala Phe Gln Cys Cys Asn
225                 230                 235                 240

Leu Gly Lys Lys Ala Ile Gly Val Phe Met Arg Met His Ser Asp Gly
                245                 250                 255

Val Gly Phe Asp Arg Ala Thr Leu Leu Asn Ile Cys Ser Ser Leu Tyr
            260                 265                 270
```

```
Lys Ser Ser Asp Leu Val Pro Asn Glu Val Ser Lys Cys Cys Leu Gln
        275                 280                 285

Leu His Ser Leu Thr Val Lys Ser Gly Leu Val Thr Gln Thr Glu Val
    290                 295                 300

Ala Thr Ala Leu Ile Lys Val Tyr Ser Glu Met Leu Glu Asp Tyr Thr
305                 310                 315                 320

Asp Cys Tyr Lys Leu Phe Met Glu Met Ser His Cys Arg Asp Ile Val
                325                 330                 335

Ala Trp Asn Gly Ile Ile Thr Ala Phe Ala Val Tyr Asp Pro Glu Arg
            340                 345                 350

Ala Ile His Leu Phe Gly Gln Leu Arg Gln Glu Lys Leu Ser Pro Asp
        355                 360                 365

Trp Tyr Thr Phe Ser Ser Val Leu Lys Ala Cys Ala Gly Leu Val Thr
    370                 375                 380

Ala Arg His Ala Leu Ser Ile His Ala Gln Val Ile Lys Gly Gly Phe
385                 390                 395                 400

Leu Ala Asp Thr Val Leu Asn Asn Ser Leu Ile His Ala Tyr Ala Lys
                405                 410                 415

Cys Gly Ser Leu Asp Leu Cys Met Arg Val Phe Asp Asp Met Asp Ser
            420                 425                 430

Arg Asp Val Val Ser Trp Asn Ser Met Leu Lys Ala Tyr Ser Leu His
        435                 440                 445

Gly Gln Val Asp Ser Ile Leu Pro Val Phe Gln Lys Met Asp Ile Asn
    450                 455                 460

Pro Asp Ser Ala Thr Phe Ile Ala Leu Leu Ser Ala Cys Ser His Ala
465                 470                 475                 480

Gly Arg Val Glu Glu Gly Leu Arg Ile Phe Arg Ser Met Phe Glu Lys
                485                 490                 495

Pro Glu Thr Leu Pro Gln Leu Asn His Tyr Ala Cys Val Ile Asp Met
            500                 505                 510

Leu Ser Arg Ala Glu Arg Phe Ala Glu Ala Glu Glu Val Ile Lys Gln
        515                 520                 525

Met Pro Met Asp Pro Asp Ala Val Val Trp Ile Ala Leu Leu Gly Ser
    530                 535                 540

Cys Arg Lys His Gly Asn Thr Arg Leu Gly Lys Leu Ala Ala Asp Lys
545                 550                 555                 560

Leu Lys Glu Leu Val Glu Pro Thr Asn Ser Met Ser Tyr Ile Gln Met
                565                 570                 575

Ser Asn Ile Tyr Asn Ala Glu Gly Ser Phe Asn Glu Ala Asn Leu Ser
            580                 585                 590

Ile Lys Glu Met Glu Thr Trp Arg Val Arg Lys Glu Pro Asp Leu Ser
        595                 600                 605

Trp Thr Glu Ile Gly Asn Lys Val His Glu Phe Ala Ser Gly Gly Arg
    610                 615                 620

His Arg Pro Asp Lys Glu Ala Val Tyr Arg Glu Leu Lys Arg Leu Ile
625                 630                 635                 640

Ser Trp Leu Lys Glu Met Gly Tyr Val Pro Glu Met Arg Ser Ala Ser
                645                 650                 655

Gln Asp Ile Glu Asp Glu Glu Gln Glu Glu Asp Asn Leu Leu His His
            660                 665                 670

Ser Glu Lys Leu Ala Leu Ala Phe Ala Val Met Glu Gly Arg Lys Ser
        675                 680                 685
```

-continued

```
Ser Asp Cys Gly Val Asn Leu Ile Gln Ile Met Lys Asn Thr Arg Ile
    690                 695                 700

Cys Ile Asp Cys His Asn Phe Met Lys Leu Ala Ser Lys Leu Leu Gly
705                 710                 715                 720

Lys Glu Ile Leu Met Arg Asp Ser Asn Arg Phe His His Phe Lys Asp
                725                 730                 735

Ser Ser Cys Ser Cys Asn Asp Tyr Trp
            740                 745


<210> SEQ ID NO 17
<211> LENGTH: 3093
<212> TYPE: DNA
<213> ORGANISM: Arabidopsis thaliana

<400> SEQUENCE: 17

atggcatcta gacaaggatc aaaatcgaga aaagcagggt taaagggtgc tgattctact      60

gcatcttcga caacctcgtc ttcgaagctt tatcaagaga cttctataga tggccatagc     120

tcccctgctt cttcatctgc tcaaagcaag cagcagttct tctcaccaga tcccttacca     180

caaactgctc agcggtctaa agaaaacgtc acagtgacag ttcgctttcg cccactcagt     240

ccaagggaaa ttcgccaagg ggaggaggtt gcatggtatg cagatgggga aactatcgtg     300

cgaaatgagc ataatccgac aatagcttat gcctatgacc gtgtctttgg acctacaacc     360

acaacacgca atgtctatga tattgctgca caccatgttg ttaatggggc tatggagggg     420

ataaatggga ccattttcgc atatggagtg acaagcagtg gaaagacaca cacaatgcat     480

ggtgaccaga gatctcctgg tattataccg ttagcagtga aagatgcttt cagcatcatc     540

caagagactc ctaatcgaga atttcttctg cgtatttcct acatggaaat atataatgag     600

gttgtcaatg atttgttgaa tccagcagga cacaatttga ggatcagaga agacaagcag     660

ggaacctttg tcgaagggat taaagaagaa gttgttttat cccctgctca tgcgctttct     720

cttattgcag ctggagaaga gcaacgacat gttggatcca caaattttaa tttgctcagc     780

agccggagcc atacaatatt tacgttgacg atagaaagta gtcccttagg tgacaagagt     840

aaaggtgaag ctgtacacct ctcacaactg aacctcgttg atctggcagg ttccgagagt     900

tcaaaggttg aaaccagtgg tgtaagacgc aaagaaggat catatataaa taaaagtttg     960

ctgacgttag ggactgtgat atcaaagctt acggatgtga gggcttcaca tgtaccatac    1020

agagactcta agttaaccag gatccttcag tcctcattga gtggtcatga ccgagtatct    1080

ctcatttgta ccgtcactcc tgcatcaagc agttcggaag aaacacacaa tacactgaaa    1140

tttgctcatc gtgcaaagca tattgagatt caagctgaac aaaacaagat aattgatgag    1200

aaatcattaa tcaagaagta ccaacgcgag attcgtcaac tgaaggaaga gttggaacag    1260

cttaaacagg aaattgtacc agttcctcag ctgaaggata ttggtgcaga tgatattgtt    1320

cttctgaagc agaagctaga agatggtcaa gtcaagctgc aatctagact cgaagaagag    1380

gaagaagcta aagcagctct cctgagtcga atccaaagat tgacgaaatt aattttggtg    1440

tcgactaaaa atccacaagc atctcgatta cctcatcgtt ttaatccgcg gaggagacat    1500

tcatttgggg aagaagagct tgcttaccta ccatacaaga ggcgggacat gatggacgat    1560

gagcaacttg acctgtatgt ttctgtggag ggaaatcatg agattagaga taatgcgtat    1620

agagaagaaa aaaagacccg caagcacgga ttgttaaatt ggttaaagcc taagaaaaga    1680

gatcacagtt caagtgccag cgaccagtca agtgtggtca aatctaacag cacaccatca    1740

actcctcaag gggaggcag tcatctgcac acagaatcaa gactttcaga aggctcgcct    1800
```

-continued

```
ttgatggaac aactctcaga gcctagggaa gacagagaag ctttagaaga cagttcccat   1860
gaaatggaga ttccggagac tagcaataaa atgagcgatg agttggatct tttgagggaa   1920
cagaaaaaga tattatctga agaggcggca ctgcaattaa gttctttaaa acggatgtca   1980
gatgaagctg caaagtcccc tcaaaatgag gagattaatg aggaaattaa agtactcaat   2040
gacgacatca aagcaaagaa tgaccagatt gctacgttgg agagacagat aatggatttt   2100
gttatgacat ctcatgaggc attggataaa tctgatatca tgcaggcagt tgctgagctg   2160
agggatcaac ttaatgagaa atcttttgaa ctcgaggtga tcgaattgtt tctgtttatg   2220
caatttttct tcatctatgc agaagttaga gatggttttg ctattgcctg gataagatta   2280
ttcattttag ctcaatatta tctctcctca tacctgaata aagtttcttc tgtgtatatt   2340
ataaaatacc agtattcaaa acgccagact atattaacaa tgaagctaat ggttaaagct   2400
gcagataatc gcatcattca gcaaacactc aatgaaaaga catgtgaatg tgaagtgttg   2460
caagaagaag ttgcaaatct aaagcagcag ctctctgagg ccctggaact agcacaggga   2520
actaagatta aagagctgaa acaagacgcc aaggaactaa gtgaatcaaa ggagcagtta   2580
gaactcagaa acaggaaact tgcagaagag agttcatatg caaaaggtct tgcatcagca   2640
gctgcagttg agctcaaggc attatccgaa gaagttgcaa agcttatgaa tcagaacgag   2700
agactagcag ctgagctggc aacacagaag agcccaatcg cacaacgaaa taagacagga   2760
acaacaacaa atgtaaggaa caatggaaga agagagagtc ttgcaaagag gcaagaacat   2820
gacagcccat caatggagct gaagagagaa ctgaggatga gtaaggaacg tgagctatcg   2880
tatgaagctg cacttggtga aaaagaacaa agagaagctg agcttgaaag gatattagaa   2940
gaaacaaaac agagagaagc atatctggag aatgagcttg ctaatatgtg ggttcttgtt   3000
tctaagctga gaagatctca aggagcagat tcagaaatct ctgattctat atcagagacg   3060
cgacaaacgg aacaaacgga aggttcattt tga                                3093
```

<210> SEQ ID NO 18
<211> LENGTH: 1030
<212> TYPE: PRT
<213> ORGANISM: Arabidopsis thaliana

<400> SEQUENCE: 18

```
Met Ala Ser Arg Gln Gly Ser Lys Ser Arg Lys Ala Gly Leu Lys Gly
1               5                   10                  15

Ala Asp Ser Thr Ala Ser Ser Thr Thr Ser Ser Ser Lys Leu Tyr Gln
            20                  25                  30

Glu Thr Ser Ile Asp Gly His Ser Ser Pro Ala Ser Ser Ser Ala Gln
        35                  40                  45

Ser Lys Gln Gln Phe Phe Ser Pro Asp Pro Leu Pro Gln Thr Ala Gln
    50                  55                  60

Arg Ser Lys Glu Asn Val Thr Val Thr Val Arg Phe Arg Pro Leu Ser
65                  70                  75                  80

Pro Arg Glu Ile Arg Gln Gly Glu Glu Val Ala Trp Tyr Ala Asp Gly
                85                  90                  95

Glu Thr Ile Val Arg Asn Glu His Asn Pro Thr Ile Ala Tyr Ala Tyr
            100                 105                 110

Asp Arg Val Phe Gly Pro Thr Thr Thr Thr Arg Asn Val Tyr Asp Ile
        115                 120                 125

Ala Ala His His Val Val Asn Gly Ala Met Glu Gly Ile Asn Gly Thr
    130                 135                 140
```

-continued

```
Ile Phe Ala Tyr Gly Val Thr Ser Ser Gly Lys Thr His Thr Met His
145                 150                 155                 160

Gly Asp Gln Arg Ser Pro Gly Ile Ile Pro Leu Ala Val Lys Asp Ala
                165                 170                 175

Phe Ser Ile Ile Gln Glu Thr Pro Asn Arg Glu Phe Leu Leu Arg Ile
            180                 185                 190

Ser Tyr Met Glu Ile Tyr Asn Glu Val Val Asn Asp Leu Leu Asn Pro
        195                 200                 205

Ala Gly His Asn Leu Arg Ile Arg Glu Asp Lys Gln Gly Thr Phe Val
    210                 215                 220

Glu Gly Ile Lys Glu Glu Val Val Leu Ser Pro Ala His Ala Leu Ser
225                 230                 235                 240

Leu Ile Ala Ala Gly Glu Glu Gln Arg His Val Gly Ser Thr Asn Phe
                245                 250                 255

Asn Leu Leu Ser Ser Arg Ser His Thr Ile Phe Thr Leu Thr Ile Glu
            260                 265                 270

Ser Ser Pro Leu Gly Asp Lys Ser Lys Gly Glu Ala Val His Leu Ser
        275                 280                 285

Gln Leu Asn Leu Val Asp Leu Ala Gly Ser Glu Ser Ser Lys Val Glu
    290                 295                 300

Thr Ser Gly Val Arg Arg Lys Glu Gly Ser Tyr Ile Asn Lys Ser Leu
305                 310                 315                 320

Leu Thr Leu Gly Thr Val Ile Ser Lys Leu Thr Asp Val Arg Ala Ser
                325                 330                 335

His Val Pro Tyr Arg Asp Ser Lys Leu Thr Arg Ile Leu Gln Ser Ser
            340                 345                 350

Leu Ser Gly His Asp Arg Val Ser Leu Ile Cys Thr Val Thr Pro Ala
        355                 360                 365

Ser Ser Ser Ser Glu Glu Thr His Asn Thr Leu Lys Phe Ala His Arg
    370                 375                 380

Ala Lys His Ile Glu Ile Gln Ala Glu Gln Asn Lys Ile Ile Asp Glu
385                 390                 395                 400

Lys Ser Leu Ile Lys Lys Tyr Gln Arg Glu Ile Arg Gln Leu Lys Glu
                405                 410                 415

Glu Leu Glu Gln Leu Lys Gln Glu Ile Val Pro Val Pro Gln Leu Lys
            420                 425                 430

Asp Ile Gly Ala Asp Asp Ile Val Leu Leu Lys Gln Lys Leu Glu Asp
        435                 440                 445

Gly Gln Val Lys Leu Gln Ser Arg Leu Glu Glu Glu Glu Glu Ala Lys
    450                 455                 460

Ala Ala Leu Leu Ser Arg Ile Gln Arg Leu Thr Lys Leu Ile Leu Val
465                 470                 475                 480

Ser Thr Lys Asn Pro Gln Ala Ser Arg Leu Pro His Arg Phe Asn Pro
                485                 490                 495

Arg Arg Arg His Ser Phe Gly Glu Glu Glu Leu Ala Tyr Leu Pro Tyr
            500                 505                 510

Lys Arg Arg Asp Met Met Asp Asp Glu Gln Leu Asp Leu Tyr Val Ser
        515                 520                 525

Val Glu Gly Asn His Glu Ile Arg Asp Asn Ala Tyr Arg Glu Glu Lys
    530                 535                 540

Lys Thr Arg Lys His Gly Leu Leu Asn Trp Leu Lys Pro Lys Lys Arg
545                 550                 555                 560
```

-continued

```
Asp His Ser Ser Ser Ala Ser Asp Gln Ser Ser Val Val Lys Ser Asn
                565                 570                 575

Ser Thr Pro Ser Thr Pro Gln Gly Gly Gly Ser His Leu His Thr Glu
            580                 585                 590

Ser Arg Leu Ser Glu Gly Ser Pro Leu Met Glu Gln Leu Ser Glu Pro
        595                 600                 605

Arg Glu Asp Arg Glu Ala Leu Glu Asp Ser Ser His Glu Met Glu Ile
    610                 615                 620

Pro Glu Thr Ser Asn Lys Met Ser Asp Glu Leu Asp Leu Leu Arg Glu
625                 630                 635                 640

Gln Lys Lys Ile Leu Ser Glu Glu Ala Ala Leu Gln Leu Ser Ser Leu
                645                 650                 655

Lys Arg Met Ser Asp Glu Ala Ala Lys Ser Pro Gln Asn Glu Glu Ile
            660                 665                 670

Asn Glu Glu Ile Lys Val Leu Asn Asp Asp Ile Lys Ala Lys Asn Asp
        675                 680                 685

Gln Ile Ala Thr Leu Glu Arg Gln Ile Met Asp Phe Val Met Thr Ser
    690                 695                 700

His Glu Ala Leu Asp Lys Ser Asp Ile Met Gln Ala Val Ala Glu Leu
705                 710                 715                 720

Arg Asp Gln Leu Asn Glu Lys Ser Phe Glu Leu Glu Val Ile Glu Leu
                725                 730                 735

Phe Leu Phe Met Gln Phe Phe Phe Ile Tyr Ala Glu Val Arg Asp Gly
            740                 745                 750

Phe Ala Ile Ala Trp Ile Arg Leu Phe Ile Leu Ala Gln Tyr Tyr Leu
        755                 760                 765

Ser Ser Tyr Leu Asn Lys Val Ser Ser Val Tyr Ile Ile Lys Tyr Gln
    770                 775                 780

Tyr Ser Lys Arg Gln Thr Ile Leu Thr Met Lys Leu Met Val Lys Ala
785                 790                 795                 800

Ala Asp Asn Arg Ile Ile Gln Gln Thr Leu Asn Glu Lys Thr Cys Glu
                805                 810                 815

Cys Glu Val Leu Gln Glu Glu Val Ala Asn Leu Lys Gln Gln Leu Ser
            820                 825                 830

Glu Ala Leu Glu Leu Ala Gln Gly Thr Lys Ile Lys Glu Leu Lys Gln
        835                 840                 845

Asp Ala Lys Glu Leu Ser Glu Ser Lys Glu Gln Leu Glu Leu Arg Asn
    850                 855                 860

Arg Lys Leu Ala Glu Glu Ser Ser Tyr Ala Lys Gly Leu Ala Ser Ala
865                 870                 875                 880

Ala Ala Val Glu Leu Lys Ala Leu Ser Glu Glu Val Ala Lys Leu Met
                885                 890                 895

Asn Gln Asn Glu Arg Leu Ala Ala Glu Leu Ala Thr Gln Lys Ser Pro
            900                 905                 910

Ile Ala Gln Arg Asn Lys Thr Gly Thr Thr Thr Asn Val Arg Asn Asn
        915                 920                 925

Gly Arg Arg Glu Ser Leu Ala Lys Arg Gln Glu His Asp Ser Pro Ser
    930                 935                 940

Met Glu Leu Lys Arg Glu Leu Arg Met Ser Lys Glu Arg Glu Leu Ser
945                 950                 955                 960

Tyr Glu Ala Ala Leu Gly Glu Lys Glu Gln Arg Glu Ala Glu Leu Glu
                965                 970                 975

Arg Ile Leu Glu Glu Thr Lys Gln Arg Glu Ala Tyr Leu Glu Asn Glu
```

-continued

```
            980                 985                 990

Leu Ala Asn Met Trp Val Leu Val  Ser Lys Leu Arg Arg  Ser Gln Gly
        995                 1000                1005

Ala Asp  Ser Glu Ile Ser Asp  Ser Ile Ser Glu Thr  Arg Gln Thr
    1010                1015                1020

Glu Gln  Thr Glu Gly Ser Phe
    1025                1030


<210> SEQ ID NO 19
<211> LENGTH: 1638
<212> TYPE: DNA
<213> ORGANISM: Arabidopsis thaliana

<400> SEQUENCE: 19

ttctaggcca aaactatctc cacgattcta acaaacaaaa attacagaaa tgtcaatgtc     60

atcgtcctcc tttatctctc tcactttctt cttccttctt ctcgtttctt catcgtcatc    120

ttccgatgac atctctgagc tattcgacga ctggtgccag aaacatggca aaacgtacgg    180

ttcagaagaa gagaggcaac agaggattca aatctttaaa gataatcacg acttcgttac    240

gcaacacaat ctcatcacta acgctactta ctctctctct ctcaatgctt tcgcggatct    300

gactcaccac gagttcaagg cttctcgtct tggtctctct gtttccgctc cgtcggtgat    360

aatggctagt aagggacaga gtctcggtgg tagcgtaaag gttccagatt ctgttgattg    420

gagaaagaag ggagctgtta ctaatgtcaa agatcaagga agctgcgggg catgttggtc    480

gttctcggcg actggagcta tggagggaat taaccagata gtaacaggag atctcatcag    540

cctctctgag caggaactga ttgattgtga caagtcctac aatgctggct gtaatggtgg    600

tctcatggac tatgcttttg aatttgtcat taaaaaccat ggaatagaca cagagaaaga    660

ctatccttat caagaacgtg atggcacctg taagaaggat aagttgaaac aaaaggttgt    720

gacaattgat agctatgctg gtgtaaaatc aaatgatgag aaagcgttaa tggaggctgt    780

agcggctcag ccagttagtg ttggcatctg tggaagcgag agagcgtttc agctatattc    840

tagtggaata ttctctggcc cgtgttcgac atcattggat catgctgtgc tcatagtagg    900

atatggttca cagaatggtg ttgattattg gattgtgaaa aactcatggg gaaaaagttg    960

gggaatggat gggtttatgc acatgcagcg taacactgaa aattcagacg gcgtttgcgg   1020

aatcaacatg cttgcttcat atcccatcaa gacacatcca aacccgcctc caccgtcccc   1080

tcctggccct acaaaatgca acctttcac gtattgttca tctggagaga cttgttgctg   1140

tgcaagagaa ttgtttggtt tatgcttctc atggaaatgc tgcgagatag aatccgctgt   1200

gtgttgcaag gatggtcgtc attgttgtcc acatgattac cctgtttgtg atacaaccag   1260

aagtctctgc cttaagaaaa ctggtaattt cactgcgatc aagcccttct ggaagaagaa   1320

ttcttcaaaa caacttggcc gatttgagga atgggttatg tgagagaagt tttacgcaca   1380

tgttacagaa aattcaaact catccataca aaaacctcgt agattcgatt atctgcgagg   1440

ggattatttg tagctgttat tgagatagat atatacgata tcatcacgga tgtattttta   1500

gtctctcatt tggatgtata caacttctga gtcaataaag gacacttgca ggacaagcac   1560

agtatttgta tctgcaagac acataaagta ataagagtat catctatgta tattatagag   1620

agactaagct tcactgtt                                                 1638


<210> SEQ ID NO 20
<211> LENGTH: 437
<212> TYPE: PRT
```

<213> ORGANISM: Arabidopsis thaliana

<400> SEQUENCE: 20

```
Met Ser Met Ser Ser Ser Ser Phe Ile Ser Leu Thr Phe Phe Phe Leu
1               5                   10                  15

Leu Leu Val Ser Ser Ser Ser Ser Ser Asp Asp Ile Ser Glu Leu Phe
            20                  25                  30

Asp Asp Trp Cys Gln Lys His Gly Lys Thr Tyr Gly Ser Glu Glu Glu
        35                  40                  45

Arg Gln Gln Arg Ile Gln Ile Phe Lys Asp Asn His Asp Phe Val Thr
    50                  55                  60

Gln His Asn Leu Ile Thr Asn Ala Thr Tyr Ser Leu Ser Leu Asn Ala
65                  70                  75                  80

Phe Ala Asp Leu Thr His His Glu Phe Lys Ala Ser Arg Leu Gly Leu
                85                  90                  95

Ser Val Ser Ala Pro Ser Val Ile Met Ala Ser Lys Gly Gln Ser Leu
            100                 105                 110

Gly Gly Ser Val Lys Val Pro Asp Ser Val Asp Trp Arg Lys Lys Gly
        115                 120                 125

Ala Val Thr Asn Val Lys Asp Gln Gly Ser Cys Gly Ala Cys Trp Ser
    130                 135                 140

Phe Ser Ala Thr Gly Ala Met Glu Gly Ile Asn Gln Ile Val Thr Gly
145                 150                 155                 160

Asp Leu Ile Ser Leu Ser Glu Gln Glu Leu Ile Asp Cys Asp Lys Ser
                165                 170                 175

Tyr Asn Ala Gly Cys Asn Gly Gly Leu Met Asp Tyr Ala Phe Glu Phe
            180                 185                 190

Val Ile Lys Asn His Gly Ile Asp Thr Glu Lys Asp Tyr Pro Tyr Gln
        195                 200                 205

Glu Arg Asp Gly Thr Cys Lys Lys Asp Lys Leu Lys Gln Lys Val Val
    210                 215                 220

Thr Ile Asp Ser Tyr Ala Gly Val Lys Ser Asn Asp Glu Lys Ala Leu
225                 230                 235                 240

Met Glu Ala Val Ala Ala Gln Pro Val Ser Val Gly Ile Cys Gly Ser
                245                 250                 255

Glu Arg Ala Phe Gln Leu Tyr Ser Ser Gly Ile Phe Ser Gly Pro Cys
            260                 265                 270

Ser Thr Ser Leu Asp His Ala Val Leu Ile Val Gly Tyr Gly Ser Gln
        275                 280                 285

Asn Gly Val Asp Tyr Trp Ile Val Lys Asn Ser Trp Gly Lys Ser Trp
    290                 295                 300

Gly Met Asp Gly Phe Met His Met Gln Arg Asn Thr Glu Asn Ser Asp
305                 310                 315                 320

Gly Val Cys Gly Ile Asn Met Leu Ala Ser Tyr Pro Ile Lys Thr His
                325                 330                 335

Pro Asn Pro Pro Pro Pro Ser Pro Pro Gly Pro Thr Lys Cys Asn Leu
            340                 345                 350

Phe Thr Tyr Cys Ser Ser Gly Glu Thr Cys Cys Cys Ala Arg Glu Leu
        355                 360                 365

Phe Gly Leu Cys Phe Ser Trp Lys Cys Cys Glu Ile Glu Ser Ala Val
    370                 375                 380

Cys Cys Lys Asp Gly Arg His Cys Cys Pro His Asp Tyr Pro Val Cys
385                 390                 395                 400
```

-continued

```
Asp Thr Thr Arg Ser Leu Cys Leu Lys Lys Thr Gly Asn Phe Thr Ala
                405                 410                 415

Ile Lys Pro Phe Trp Lys Lys Asn Ser Ser Lys Gln Leu Gly Arg Phe
            420                 425                 430

Glu Glu Trp Val Met
        435


<210> SEQ ID NO 21
<211> LENGTH: 1862
<212> TYPE: DNA
<213> ORGANISM: Arabidopsis thaliana

<400> SEQUENCE: 21

atgaaatctg caaatttagg tcttttaata gaaatctgaa tttcatgttg ctgaaagaat      60

ttacaacgaa gttgtaaata ctctgagaaa catgtaagtc aggagagagt cccttctatg     120

gtttatattt ggcggctttt aagaagcata cgcatatcaa gtgtttgatg aaattcctca     180

gagaagatga tgtccaccac agtcagatta aacaggttta cgtatctaac gagtactgca     240

aaactgacac gttacttttg ctctcaccat ttagttgacc gatcggaaac ggcgttgcat     300

gaagttattc ggatagtttc ttctccagtt ggtggtctag atgaccttga agaaaacttg     360

aaccaggttt ctgtttctcc atcatcaaac cttgttaccc aagtgattga gtcttgcaag     420

aacgagactt caccgagaag gctgttgagg tttttctcct ggtcgtgtaa aagcttggga     480

tctagtttac acgacaagga attcaactat gtcctaagag ttttggctga gaagaaggat     540

cacacagcta tgcagatact cttatcagat ctcaggaagg agaatcgggc gatggacaag     600

caaacgttta gcattgtcgc tgaaactctg gttaaggttg gtaaggaaga agatgcaata     660

ggtatcttca agatcttgga caaattttct tgcccacaag atggtttcac tgtgacggct     720

attataagcg ctctttgttc cagaggacat gtgaagagag cattgggagt tatgcatcat     780

cacaaggatg taatatccgg gaatgaattg tctgtgtata gaagtctttt attcgggtgg     840

tcggtacaaa gaaacgtgaa ggaagcaaga agagttatac aagatatgaa atcagcaggg     900

attacaccgg atttgttctg tttcaactcg ttgctgacct gcctttgcga aagaaacgtg     960

aatcgaaacc cgtctgggct tgttcctgaa gctttgaata ttatgttgga gatgaggtct    1020

tacaaaatcc aacctacgtc tatgagttac aacattttgc tctcttgttt gggaaggact    1080

aggagggtga gagagtcctg ccagatttta gaacagatga aaagatcggg atgtgatccg    1140

gatacaggga gctattactt cgttgtgagg gtcctgtatt tgacaggaag gtttggtaaa    1200

ggcaaccaaa ttgtggatga gatgatcgag agaggattta gacccgaacg caaattctat    1260

tatgatctga tcggggttct ttgtggggtc gagcgggtta actttgctct tcaattgttt    1320

gagaagatga agagaagctc agtgggtggt tatggtcagg tttatgatct gctcatacca    1380

aaactatgta aaggaggaaa ctttgagaaa ggaagagagc tttgggaaga ggcattgtca    1440

attgatgtta cacttagttg ctccattagt ttgcttgatc catctgtcac agaggttttc    1500

aaacctatga agatgaaaga agaagctgca atggtggatc gtcgtgctct taacttgaag    1560

attcacgcta gaatgaacaa aacaaagcca aaactgaaac taaaaccgaa acgcaggagc    1620

aagacaaaga agaagaatct gcaacattga ttgatttctt ctacccattg ttaagaacat    1680

ctgatatagc aggcaatgta tcacaagaaa ctcaagtaag atgttctgct tttatgtat     1740

tagtagtaat gcagaagcaa aggacatgag attcttttgt tgttctcttt gtcccattga    1800

ttcttattac gaaaaatatg ggttctgaag aatacaaaac aagagacaag aatattgtga    1860
```

-continued tc 1862

<210> SEQ ID NO 22
<211> LENGTH: 487
<212> TYPE: PRT
<213> ORGANISM: Arabidopsis thaliana

<400> SEQUENCE: 22

Met Met Ser Thr Thr Val Arg Leu Asn Arg Phe Thr Tyr Leu Thr Ser
1 5 10 15

Thr Ala Lys Leu Thr Arg Tyr Phe Cys Ser His His Leu Val Asp Arg
20 25 30

Ser Glu Thr Ala Leu His Glu Val Ile Arg Ile Val Ser Ser Pro Val
35 40 45

Gly Gly Leu Asp Asp Leu Glu Glu Asn Leu Asn Gln Val Ser Val Ser
50 55 60

Pro Ser Ser Asn Leu Val Thr Gln Val Ile Glu Ser Cys Lys Asn Glu
65 70 75 80

Thr Ser Pro Arg Arg Leu Leu Arg Phe Phe Ser Trp Ser Cys Lys Ser
85 90 95

Leu Gly Ser Ser Leu His Asp Lys Glu Phe Asn Tyr Val Leu Arg Val
100 105 110

Leu Ala Glu Lys Lys Asp His Thr Ala Met Gln Ile Leu Leu Ser Asp
115 120 125

Leu Arg Lys Glu Asn Arg Ala Met Asp Lys Gln Thr Phe Ser Ile Val
130 135 140

Ala Glu Thr Leu Val Lys Val Gly Lys Glu Glu Asp Ala Ile Gly Ile
145 150 155 160

Phe Lys Ile Leu Asp Lys Phe Ser Cys Pro Gln Asp Gly Phe Thr Val
165 170 175

Thr Ala Ile Ile Ser Ala Leu Cys Ser Arg Gly His Val Lys Arg Ala
180 185 190

Leu Gly Val Met His His His Lys Asp Val Ile Ser Gly Asn Glu Leu
195 200 205

Ser Val Tyr Arg Ser Leu Leu Phe Gly Trp Ser Val Gln Arg Asn Val
210 215 220

Lys Glu Ala Arg Arg Val Ile Gln Asp Met Lys Ser Ala Gly Ile Thr
225 230 235 240

Pro Asp Leu Phe Cys Phe Asn Ser Leu Leu Thr Cys Leu Cys Glu Arg
245 250 255

Asn Val Asn Arg Asn Pro Ser Gly Leu Val Pro Glu Ala Leu Asn Ile
260 265 270

Met Leu Glu Met Arg Ser Tyr Lys Ile Gln Pro Thr Ser Met Ser Tyr
275 280 285

Asn Ile Leu Leu Ser Cys Leu Gly Arg Thr Arg Arg Val Arg Glu Ser
290 295 300

Cys Gln Ile Leu Glu Gln Met Lys Arg Ser Gly Cys Asp Pro Asp Thr
305 310 315 320

Gly Ser Tyr Tyr Phe Val Val Arg Val Leu Tyr Leu Thr Gly Arg Phe
325 330 335

Gly Lys Gly Asn Gln Ile Val Asp Glu Met Ile Glu Arg Gly Phe Arg
340 345 350

Pro Glu Arg Lys Phe Tyr Tyr Asp Leu Ile Gly Val Leu Cys Gly Val
355 360 365

-continued

```
Glu Arg Val Asn Phe Ala Leu Gln Leu Phe Glu Lys Met Lys Arg Ser
    370                 375                 380

Ser Val Gly Gly Tyr Gly Gln Val Tyr Asp Leu Leu Ile Pro Lys Leu
385                 390                 395                 400

Cys Lys Gly Gly Asn Phe Glu Lys Gly Arg Glu Leu Trp Glu Glu Ala
                405                 410                 415

Leu Ser Ile Asp Val Thr Leu Ser Cys Ser Ile Ser Leu Leu Asp Pro
            420                 425                 430

Ser Val Thr Glu Val Phe Lys Pro Met Lys Met Lys Glu Glu Ala Ala
        435                 440                 445

Met Val Asp Arg Arg Ala Leu Asn Leu Lys Ile His Ala Arg Met Asn
    450                 455                 460

Lys Thr Lys Pro Lys Leu Lys Leu Lys Pro Lys Arg Arg Ser Lys Thr
465                 470                 475                 480

Lys Lys Lys Asn Leu Gln His
                485


<210> SEQ ID NO 23
<211> LENGTH: 1691
<212> TYPE: DNA
<213> ORGANISM: Arabidopsis thaliana

<400> SEQUENCE: 23

agttatcttc atacttcata taaatctctg ctcattttcg ataaaaagtt gaatcctttt      60

cacattttcc gctcaattcg atcttacatg ttaacaatgg ttggtctaac tccagctgag     120

gatcgttcag agattgcctt tttcgacgtc gagacgacaa ttccgttccg agttggtcag     180

gggtacgcga ttctggagtt tggatcgatt ctggtttgcc ccaagaagct tgtggagctg     240

aaaaactact ctgttctggt tcgtcctgct aatctcaacc tcatcacgcc tcggtccgtg     300

aagtgcaacg gcatcaaacg cgaagacgtc gaatcagctc ttacctttgc agatatcgcc     360

gacaccgtct acgatattct ccatggaagg atatgggcag gtcataacat attgaagttc     420

gattgtccaa ggataagaga agcatttgct gagattggac gagatccacc agagccaaag     480

ggcaccattg actccttggc tttgcttact caaaggtttg ggagaagagc tggtgatatg     540

aagatggcga ctttggctac atactttgga cttggaaacc agacgcatag gagtctggac     600

gatgtaagga tgaacttcga ggttctcaag tattgtgcca ctgttttgtt cttggagtca     660

agtcttccag atgaacttat agagaactcg gttactacta ctactcctga aactagttca     720

agaaggcgta ggactataaa aaaatctcct ctgcaatctc ccactgatca gcagacagga     780

gagaacatga caactatacc tattttatca tttgtttcat ccgcagaagc tcaaacggat     840

ccatttgata tgagcacttt gaggaacgaa atagcccctg aagttcttca atcagatgtt     900

cccatggaag aagaacaaaa tcagcagtct gagactgttg cctctgaagg taccggtgac     960

caggaaggat tcatggagct agataaaata tctgtttcaa gtatcagagc aactcatgtc    1020

ccgctatatg acgggagcca aacaatgaag ctgcaactct tccttgggga cagacccctt    1080

cagctccatt gtcctcgtct gaaagtacgg tttggaatca atgggaaatt tatggataaa    1140

gctggaagac ggaggttgaa ctttgtaatt gatctgtatc caagtctctg caacgtactt    1200

caagaatgcg acagtgctgc acagacaata tctgttgatt caggcagtgg ttctgactgg    1260

aaccctctag tcattccaat gaaaggattt ctgaactgtc ccactgcaag gatacatata    1320

cccacagagt taaatggaga tatagatcgg tacgcagctg agatacacca gaaagagttc    1380

tctggagcta ctgctactca gaaactcatt tctagcaacc ccaaggctga agagattgag    1440
```

```
tctttgttga atccgagaac tgttcttgac gctttcttgt ctctggagcc atatgattat   1500

cagcagagag ccggaatccg tctagttgct agaaagcttg ttatacatta gtggacctta   1560

ctcaatagca ccacagagaa ttaaagaaat cagagtttag tggactgtag agatttattt   1620

atgtagtcat gaaagaaaca cagaactgtt gttcctgaca gtagatatac agctgattat   1680

gttcttagtt t                                                        1691


<210> SEQ ID NO 24
<211> LENGTH: 487
<212> TYPE: PRT
<213> ORGANISM: Arabidopsis thaliana

<400> SEQUENCE: 24

Met Leu Thr Met Val Gly Leu Thr Pro Ala Glu Asp Arg Ser Glu Ile
1               5                   10                  15

Ala Phe Phe Asp Val Glu Thr Thr Ile Pro Phe Arg Val Gly Gln Gly
            20                  25                  30

Tyr Ala Ile Leu Glu Phe Gly Ser Ile Leu Val Cys Pro Lys Lys Leu
        35                  40                  45

Val Glu Leu Lys Asn Tyr Ser Val Leu Val Arg Pro Ala Asn Leu Asn
    50                  55                  60

Leu Ile Thr Pro Arg Ser Val Lys Cys Asn Gly Ile Lys Arg Glu Asp
65                  70                  75                  80

Val Glu Ser Ala Leu Thr Phe Ala Asp Ile Ala Asp Thr Val Tyr Asp
                85                  90                  95

Ile Leu His Gly Arg Ile Trp Ala Gly His Asn Ile Leu Lys Phe Asp
            100                 105                 110

Cys Pro Arg Ile Arg Glu Ala Phe Ala Glu Ile Gly Arg Asp Pro Pro
        115                 120                 125

Glu Pro Lys Gly Thr Ile Asp Ser Leu Ala Leu Leu Thr Gln Arg Phe
    130                 135                 140

Gly Arg Arg Ala Gly Asp Met Lys Met Ala Thr Leu Ala Thr Tyr Phe
145                 150                 155                 160

Gly Leu Gly Asn Gln Thr His Arg Ser Leu Asp Asp Val Arg Met Asn
                165                 170                 175

Phe Glu Val Leu Lys Tyr Cys Ala Thr Val Leu Phe Leu Glu Ser Ser
            180                 185                 190

Leu Pro Asp Glu Leu Ile Glu Asn Ser Val Thr Thr Thr Thr Pro Glu
        195                 200                 205

Thr Ser Ser Arg Arg Arg Arg Thr Ile Lys Lys Ser Pro Leu Gln Ser
    210                 215                 220

Pro Thr Asp Gln Gln Thr Gly Glu Asn Met Thr Thr Ile Pro Ile Leu
225                 230                 235                 240

Ser Phe Val Ser Ser Ala Glu Ala Gln Thr Asp Pro Phe Asp Met Ser
                245                 250                 255

Thr Leu Arg Asn Glu Ile Ala Pro Glu Val Leu Gln Ser Asp Val Pro
            260                 265                 270

Met Glu Glu Glu Gln Asn Gln Gln Ser Glu Thr Val Ala Ser Glu Gly
        275                 280                 285

Thr Gly Asp Gln Glu Gly Phe Met Glu Leu Asp Lys Ile Ser Val Ser
    290                 295                 300

Ser Ile Arg Ala Thr His Val Pro Leu Tyr Asp Gly Ser Gln Thr Met
305                 310                 315                 320
```

-continued

```
Lys Leu Gln Leu Phe Leu Gly Asp Arg Pro Leu Gln Leu His Cys Pro
                325                 330                 335

Arg Leu Lys Val Arg Phe Gly Ile Asn Gly Lys Phe Met Asp Lys Ala
            340                 345                 350

Gly Arg Arg Arg Leu Asn Phe Val Ile Asp Leu Tyr Pro Ser Leu Cys
        355                 360                 365

Asn Val Leu Gln Glu Cys Asp Ser Ala Ala Gln Thr Ile Ser Val Asp
    370                 375                 380

Ser Gly Ser Gly Ser Asp Trp Asn Pro Leu Val Ile Pro Met Lys Gly
385                 390                 395                 400

Phe Leu Asn Cys Pro Thr Ala Arg Ile His Ile Pro Thr Glu Leu Asn
                405                 410                 415

Gly Asp Ile Asp Arg Tyr Ala Ala Glu Ile His Gln Lys Glu Phe Ser
            420                 425                 430

Gly Ala Thr Ala Thr Gln Lys Leu Ile Ser Ser Asn Pro Lys Ala Glu
        435                 440                 445

Glu Ile Glu Ser Leu Leu Asn Pro Arg Thr Val Leu Asp Ala Phe Leu
    450                 455                 460

Ser Leu Glu Pro Tyr Asp Tyr Gln Gln Arg Ala Gly Ile Arg Leu Val
465                 470                 475                 480

Ala Arg Lys Leu Val Ile His
                485
```

<210> SEQ ID NO 25
<211> LENGTH: 2179
<212> TYPE: DNA
<213> ORGANISM: Arabidopsis thaliana

<400> SEQUENCE: 25

```
gaagagacat cagatcttat caaaacccta gctttcggtg tctctctcga tcctttagct     60

caatcgaaaa ctgaatttag gagctgcgat gggttccaga tctcgtaatg ataatttcca    120

gtccggcgat ggcgctagtc ctgggaaaat attcattgga ggattgcaca aagacacgac    180

taatactgtg ttcaataagc actttggcaa gtacggggag attacagatt ctgtcattat    240

gcgagatcga catactggac aacctagggg tttcggtttc atcaccttcg ctgacccttc    300

tgttgttgac aaagttatcg aagatactca tgtcatcaat ggcaaacagg ttgagatcaa    360

aaggactatt ccgaaaggtg ctggtggcaa tcagtcaaag gacatcaaaa caaagaagat    420

tttcgttggt ggtataccct caacggttac agaagatgaa cttaaggact tctttgccaa    480

gtatgggaac gtggtggagc accaggttat tcgagaccat gaaacaaaca ggtccagagg    540

ttttggtttt gtaatttttg atagcgaaga agtcgtagat gaattattgt ccaaaggaaa    600

catgatcgat atggcagaca ctcaggtaag cttgtacaaa tggggattag aattttggtt    660

catgatgaca tatttatctt ggtttcaatt tgatattttc tccttgttcc tttcattata    720

cacgtttaac ttagttagaa ttctacccac tagcttacca aatgtaagga gcttgtcaca    780

gtaagatagg aaatccctgc tatagtttgg gtccttagca tagctaggtt aattaagttg    840

ctttgttgta ggtggagatc aagaaagctg aaccaaagaa atctctaaac cgttcacctc    900

cttcttacgg tagtcaccct agaggtcgtt cttctaacga tagttatgca agttatggtg    960

gaccttacgg aggttttgat ggagggtatg gtcatcctcc aggtcccatt aggtcacatg   1020

gaggtcctgc tagtagatat gctgggggat atgggtatgg tcgtggcagt gtaggccctg   1080

aatttggagg aggttataat aattatgggg gtggtagttt aggaggttac cggaatgaac   1140
```

-continued

```
caccccttgg ctattctagt cgttttggac cctatgggag tgggtttggt ggtgagggat   1200

atggccgtgg aggagaagga gcctatttgg gatatcctcg tggaggaggg gaaggctatg   1260

ggggatatgg tgggcctggt tacggcggtg catatgaatc tggtggccca ggtggcagtt   1320

atgaaggagc aggtggtcca tatgggaggg gttatagtag cagtagtcga taccatccgt   1380

atgcaaggta gggtcgaggt aatagcaatc agttggagct atagaagctt ctctcacagg   1440

ttcctctaga ttgttccaat tgctctaggt gcattctaga gttatcatgt agcgccaaca   1500

tcaggaaggg ttgctaagga caggaagagc atcaaaaagc ttttattagt catcttttag   1560

ttgtgtgttt acctaattta agtgttgtct tatctctata acttagattg tgttatgtag   1620

actttagcat atttgggctt ggagtttgtt tctcactggc acaagaatga tttatcattt   1680

ggtagtcttg ttagatgatc aattactcgc ttagcttagt tttcacaatc atacgaatta   1740

gcttaagaag ctctgcaaaa tgtgcactca tctattcttt agagctcaag ttgaatgctt   1800

tatgtggtct cttgtatctc tgtacatttt gttgtgctga acaaaggttt gacggcagtt   1860

agtgcatgtg taagtaggca tatttttgtc agctgcatac gtaggttcta gctacaaatt   1920

ggaattgtat gtgtttgaaa acgtaaaatc aattataaat gtttttgaaa atcatctata   1980

caagcatggt tatttggttc ttgtttcctt atttttttcgg gtaagggcca cggataattg   2040

gttagacatt ggttctaata atgtgggttt tgttatctgt aatttctcgt caaaatgatg   2100

tactgtatca ttaaatgaat atcacttatt gtacatgctt ttataagtta attgaaatcc   2160

aaactctttt acgttttaa                                                2179
```

<210> SEQ ID NO 26
<211> LENGTH: 231
<212> TYPE: PRT
<213> ORGANISM: Arabidopsis thaliana

<400> SEQUENCE: 26

```
Met Gly Ser Arg Ser Arg Asn Asp Asn Phe Gln Ser Gly Asp Gly Ala
1               5                   10                  15

Ser Pro Gly Lys Ile Phe Ile Gly Gly Leu His Lys Asp Thr Thr Asn
            20                  25                  30

Thr Val Phe Asn Lys His Phe Gly Lys Tyr Gly Glu Ile Thr Asp Ser
        35                  40                  45

Val Ile Met Arg Asp Arg His Thr Gly Gln Pro Arg Gly Phe Gly Phe
    50                  55                  60

Ile Thr Phe Ala Asp Pro Ser Val Val Asp Lys Val Ile Glu Asp Thr
65                  70                  75                  80

His Val Ile Asn Gly Lys Gln Val Glu Ile Lys Arg Thr Ile Pro Lys
                85                  90                  95

Gly Ala Gly Gly Asn Gln Ser Lys Asp Ile Lys Thr Lys Lys Ile Phe
            100                 105                 110

Val Gly Gly Ile Pro Ser Thr Val Thr Glu Asp Glu Leu Lys Asp Phe
        115                 120                 125

Phe Ala Lys Tyr Gly Asn Val Val Glu His Gln Val Ile Arg Asp His
    130                 135                 140

Glu Thr Asn Arg Ser Arg Gly Phe Gly Phe Val Ile Phe Asp Ser Glu
145                 150                 155                 160

Glu Val Val Asp Glu Leu Leu Ser Lys Gly Asn Met Ile Asp Met Ala
                165                 170                 175

Asp Thr Gln Val Ser Leu Tyr Lys Trp Gly Leu Glu Phe Trp Phe Met
            180                 185                 190
```

```
Met Thr Tyr Leu Ser Trp Phe Gln Phe Asp Ile Phe Ser Leu Phe Leu
        195                 200                 205

Ser Leu Tyr Thr Phe Asn Leu Val Arg Ile Leu Pro Thr Ser Leu Pro
    210                 215                 220

Asn Val Arg Ser Leu Ser Gln
225                 230


<210> SEQ ID NO 27
<211> LENGTH: 1959
<212> TYPE: DNA
<213> ORGANISM: Arabidopsis thaliana

<400> SEQUENCE: 27

aattagatga agagacatca gatcttatca aaaccctagc tttcggtgtc tctctcgatc     60

ctttagctca atcgaaaact gaatttagga gctgcgatgg gttccagatc tcgtaatgat    120

aatttccagt ccggcgatgg cgctagtcct gggaaaatat tcattggagg attgcacaaa    180

gacacgacta atactgtgtt caataagcac tttggcaagt acggggagat tacagattct    240

gtcattatgc gagatcgaca tactggacaa cctaggggtt tcggtttcat caccttcgct    300

gacccttctg ttgttgacaa agttatcgaa gatactcatg tcatcaatgg caaacaggtt    360

gagatcaaaa ggactattcc gaaaggtgct ggtggcaatc agtcaaagga catcaaaaca    420

aagaagattt tcgttggtgg tataccctca acggttacag aagatgaact taaggacttc    480

tttgccaagt atgggaacgt ggtggagcac caggttattc gagaccatga aacaaacagg    540

tccagaggtt ttggttttgt aatttttgat agcgaagaag tcgtagatga attattgtcc    600

aaaggaaaca tgatcgatat ggcagacact caggtggaga tcaagaaagc tgaaccaaag    660

aaatctctaa accgttcacc tccttcttac ggtagtcacc ctagaggtcg ttcttctaac    720

gatagttatg caagttatgg tggaccttac ggaggttttg atggagggta tggtcatcct    780

ccaggtccca ttaggtcaca tggaggtcct gctagtagat atgctggggg atatgggtat    840

ggtcgtggca gtgtaggccc tgaatttgga ggaggttata ataattatgg gggtggtagt    900

ttaggaggtt accggaatga accacccctt ggctattcta gtcgttttgg accctatggg    960

agtgggtttg gtggtgaggg atatggccgt ggaggagaag gagcctattt gggatatcct   1020

cgtggaggag gggaaggcta tgggggatat ggtgggcctg gttacggcgg tgcatatgaa   1080

tctggtggcc caggtggcag ttatgaagga gcaggtggtc catatgggag ggggttatagt  1140

agcagtagtc gataccatcc gtatgcaagg tagggtcgag gtaatagcaa tcagttggag   1200

ctatagaagc ttctctcaca ggttcctcta gattgttcca attgctctag gtgcattcta   1260

gagttatcat gtagcgccaa catcaggaag ggttgctaag gacaggaaga gcatcaaaaa   1320

gcttttatta gtcatctttt agttgtgtgt ttacctaatt taagtgttgt cttatctcta   1380

taacttagat tgtgttatgt agactttagc atatttgggc ttggagtttg tttctcactg   1440

gcacaagaat gatttatcat ttggtagtct tgttagatga tcaattactc gcttagctta   1500

gttttcacaa tcatacgaat tagcttaaga agctctgcaa aatgtgcact catctattct   1560

ttagagctca agttgaatgc tttatgtggt ctcttgtatc tctgtacatt ttgttgtgct   1620

gaacaaaggt ttgacggcag ttagtgcatg tgtaagtagg catatttttg tcagctgcat   1680

acgtaggttc tagctacaaa ttggaattgt atgtgtttga aaacgtaaaa tcaattataa   1740

atgtttttga aaatcatcta tacaagcatg gttatttggt tcttgtttcc ttattttttc   1800

gggtaagggc cacggataat tggttagaca ttggttctaa taatgtgggt tttgttatct   1860
```

-continued

```
gtaatttctc gtcaaaatga tgtactgtat cattaaatga atatcactta ttgtacatgc   1920

ttttataagt taattgaaat ccaaactctt ttacgtttt                          1959


<210> SEQ ID NO 28
<211> LENGTH: 358
<212> TYPE: PRT
<213> ORGANISM: Arabidopsis thaliana

<400> SEQUENCE: 28

Met Gly Ser Arg Ser Arg Asn Asp Asn Phe Gln Ser Gly Asp Gly Ala
1               5                   10                  15

Ser Pro Gly Lys Ile Phe Ile Gly Gly Leu His Lys Asp Thr Thr Asn
            20                  25                  30

Thr Val Phe Asn Lys His Phe Gly Lys Tyr Gly Glu Ile Thr Asp Ser
        35                  40                  45

Val Ile Met Arg Asp Arg His Thr Gly Gln Pro Arg Gly Phe Gly Phe
    50                  55                  60

Ile Thr Phe Ala Asp Pro Ser Val Val Asp Lys Val Ile Glu Asp Thr
65                  70                  75                  80

His Val Ile Asn Gly Lys Gln Val Glu Ile Lys Arg Thr Ile Pro Lys
                85                  90                  95

Gly Ala Gly Gly Asn Gln Ser Lys Asp Ile Lys Thr Lys Lys Ile Phe
            100                 105                 110

Val Gly Gly Ile Pro Ser Thr Val Thr Glu Asp Glu Leu Lys Asp Phe
        115                 120                 125

Phe Ala Lys Tyr Gly Asn Val Val Glu His Gln Val Ile Arg Asp His
    130                 135                 140

Glu Thr Asn Arg Ser Arg Gly Phe Gly Phe Val Ile Phe Asp Ser Glu
145                 150                 155                 160

Glu Val Val Asp Glu Leu Leu Ser Lys Gly Asn Met Ile Asp Met Ala
                165                 170                 175

Asp Thr Gln Val Glu Ile Lys Lys Ala Glu Pro Lys Lys Ser Leu Asn
            180                 185                 190

Arg Ser Pro Pro Ser Tyr Gly Ser His Pro Arg Gly Arg Ser Ser Asn
        195                 200                 205

Asp Ser Tyr Ala Ser Tyr Gly Gly Pro Tyr Gly Gly Phe Asp Gly Gly
    210                 215                 220

Tyr Gly His Pro Pro Gly Pro Ile Arg Ser His Gly Gly Pro Ala Ser
225                 230                 235                 240

Arg Tyr Ala Gly Gly Tyr Gly Tyr Gly Arg Gly Ser Val Gly Pro Glu
                245                 250                 255

Phe Gly Gly Gly Tyr Asn Asn Tyr Gly Gly Gly Ser Leu Gly Gly Tyr
            260                 265                 270

Arg Asn Glu Pro Pro Leu Gly Tyr Ser Ser Arg Phe Gly Pro Tyr Gly
        275                 280                 285

Ser Gly Phe Gly Gly Glu Gly Tyr Gly Arg Gly Gly Glu Gly Ala Tyr
    290                 295                 300

Leu Gly Tyr Pro Arg Gly Gly Gly Glu Gly Tyr Gly Gly Tyr Gly Gly
305                 310                 315                 320

Pro Gly Tyr Gly Gly Ala Tyr Glu Ser Gly Gly Pro Gly Gly Ser Tyr
                325                 330                 335

Glu Gly Ala Gly Gly Pro Tyr Gly Arg Gly Tyr Ser Ser Ser Ser Arg
            340                 345                 350
```

-continued

```
Tyr His Pro Tyr Ala Arg
        355


<210> SEQ ID NO 29
<211> LENGTH: 500
<212> TYPE: DNA
<213> ORGANISM: Arabidopsis thaliana

<400> SEQUENCE: 29

gaaggaaaaa gaaaaaacac aaatggaagg gaaagaggaa gaagcaaaga ggaggatgat      60

gatgaagatc aaacttaagg agacagaagc agacgtaagc caagacgaca ttaaaagaca     120

agaagcttac aacatgtctc cacgcgtacg tcgtggtggt ggtggtggcg gtggctcggt     180

aggtatgagc aagtcatcga gcgtgaggca aaactgttta tgcgcaccaa ctacacaccc     240

tggctccttc aggtgccgtt accaccgtcg taacgctgga ctcgggatgt ctcgtggcac     300

atccgttccc tctaaccttt ccatgttggc tggtggagac tctaattctc ccaagtgatg     360

attaatatat attatgtgtt tcttctcatc aatttaaaat tctcgtatgt gtctgtgtat     420

atacaaaaat gcataagtcg agaaatctct ggatattcac tttgctgttt gcacaaatga     480

aataaattca aatgatcgtg                                                 500


<210> SEQ ID NO 30
<211> LENGTH: 111
<212> TYPE: PRT
<213> ORGANISM: Arabidopsis thaliana

<400> SEQUENCE: 30

Met Glu Gly Lys Glu Glu Glu Ala Lys Arg Arg Met Met Met Lys Ile
1               5                   10                  15

Lys Leu Lys Glu Thr Glu Ala Asp Val Ser Gln Asp Asp Ile Lys Arg
            20                  25                  30

Gln Glu Ala Tyr Asn Met Ser Pro Arg Val Arg Arg Gly Gly Gly Gly
        35                  40                  45

Gly Gly Gly Ser Val Gly Met Ser Lys Ser Ser Ser Val Arg Gln Asn
    50                  55                  60

Cys Leu Cys Ala Pro Thr Thr His Pro Gly Ser Phe Arg Cys Arg Tyr
65                  70                  75                  80

His Arg Arg Asn Ala Gly Leu Gly Met Ser Arg Gly Thr Ser Val Pro
                85                  90                  95

Ser Asn Leu Ser Met Leu Ala Gly Gly Asp Ser Asn Ser Pro Lys
            100                 105                 110


<210> SEQ ID NO 31
<211> LENGTH: 2328
<212> TYPE: DNA
<213> ORGANISM: Arabidopsis thaliana

<400> SEQUENCE: 31

atgaagagtt gcagaacctt aatttttgtg gcaataattc tcaacgggct gagtactttc      60

gttgcacatg ccggtgctga gagcaaggtt cacatagttt atttgggtga gaagcagcac     120

gatgatcccg agtttgtcac ggaatctcat catcggatgt tgtggtcact tcttggaagt     180

aaagaggatg cccatagttc aatggtccat agttaccgac atggcttctc gggttttgca     240

gccaagctta ccaagtccca agccaagaag cttgcagatt tacctgaagt tgttcacgtc     300

acgccggata gcttctacca actagataca actcggactt gggactactt aggcctttcc     360

gtcgccaatc ctaaaaatct tctaaatgac actaatatgg gtgaagaagt tatcattggc     420
```

```
attgtagact caggagtttg gccagaatct gaagtcttta atgacaatgg gattggacca    480

gtgccaagcc actggaaagg aggctgtgta tcaggagaga atttcacttc ctctcagtgc    540

aacaaaaagc ttataggagc caaatacttc atcaatgggt ttcttgcgac gcacgaaagc    600

ttcaactcca cagaatcact tgactttatt tcccctagag accgtagcgg acatggcacg    660

catgtagcca ccatagcggg tggttcctac gtgcctagca taagctacaa ggggttagct    720

ggagggactg tgagaggtgg ggcaccacgt gctcgtatag cgatgtacaa agcttgttgg    780

tatctagatc gttttgacat aaatacatgt tcatctgctg atatcttgaa agctatggat    840

gaagctatgc atgatggtgt tgatgttttg tccttgtcta tcggctatcg ttttccttac    900

ttcccagaaa ctgatgttcg cgccgtgata gccacgggag cattccatgc tgttttaaag    960

ggtatcacag ttgtttgttc gggaggtaac tctggtcctg cggctcagac tgtgggaaac   1020

acggctccat ggattttgac agtggctgca actactttag accgatcttt tcccacacct   1080

atcacacttg ggaacaataa actgatattg ggtcaagcaa tgtacaccgg tccagaactt   1140

ggcttcacta gcttggttta cccagagaat ccagggaaca gcaacgagag tttttctggt   1200

gactgtgagc ttctattttt caactccaat catacaatgg cggggaaagt cgtgttatgc   1260

ttcacaacat caacacgtta catcactgta tcaagtgctg tgtcttatgt gaaggaagct   1320

ggtggtcttg gcgtaattgt agcaagaaac cccggcgaca atctttcacc atgtgaagat   1380

gattttcctt gtgttgctgt tgactacgag cttgggacag atatactttt atacatacgt   1440

tccacaggat tacctgttgt gaagatacaa ccttctaaaa cacttgttgg acaaccagtg   1500

ggcacaaagg ttgcagattt ctcatcaaga ggacctaatt caattgagcc tgccatcctc   1560

aaaccggata tagcagcacc aggagtgagc atattagcgg ctacaactac caataaaact   1620

ttcaacgacc gaggattcat ttcttgtca gggacatcaa tggcagctcc taccatttca   1680

ggagttgttg ctcttctcaa agctctgcac cgtgattggt ctcctgctgc cattagatca   1740

gccattgtca ccacagcttg gagaacagat ccatttggag agcagatatt tgcagaaggg   1800

tcacctcgga agctagctga tccgtttgac tatggtggag gccttgtgaa tccagagaaa   1860

gctgcaaaac ctggtcttgt atatgacttg ggacttgaag actatgttct ctacatgtgc   1920

tctgttggtt acaacgagac atcaatctct caacttgtcg gaaaaggaac agtttgttcg   1980

aatcccaaac catctgttct tgattttaac ttgccttcca tcacaatccc aaacctcaaa   2040

gatgaagtca ctctcaccag aaccctcact aacgttggac aacttgagtc ggtctataaa   2100

gttgtgatcg agccaccgat aggcattcaa gtgactgtga caccagagac gcttctgttt   2160

aactctacaa ccaaaagggt ctcttttaaa gtcaaagttt cgaccacaca caaaatcaac   2220

acaggttact tctttggaag cttgacttgg agtgactctc tacataatgt gaccattcct   2280

ctctctgtga gaactcaaat tttgcagaac tactacgatg aaaactga                2328
```

<210> SEQ ID NO 32
<211> LENGTH: 775
<212> TYPE: PRT
<213> ORGANISM: Arabidopsis thaliana

<400> SEQUENCE: 32

```
Met Lys Ser Cys Arg Thr Leu Ile Phe Val Ala Ile Ile Leu Asn Gly
1               5                   10                  15

Leu Ser Thr Phe Val Ala His Ala Gly Ala Glu Ser Lys Val His Ile
            20                  25                  30
```

-continued

```
Val Tyr Leu Gly Glu Lys Gln His Asp Asp Pro Glu Phe Val Thr Glu
        35                  40                  45

Ser His His Arg Met Leu Trp Ser Leu Leu Gly Ser Lys Glu Asp Ala
    50                  55                  60

His Ser Ser Met Val His Ser Tyr Arg His Gly Phe Ser Gly Phe Ala
65                  70                  75                  80

Ala Lys Leu Thr Lys Ser Gln Ala Lys Lys Leu Ala Asp Leu Pro Glu
                85                  90                  95

Val Val His Val Thr Pro Asp Ser Phe Tyr Gln Leu Asp Thr Thr Arg
            100                 105                 110

Thr Trp Asp Tyr Leu Gly Leu Ser Val Ala Asn Pro Lys Asn Leu Leu
        115                 120                 125

Asn Asp Thr Asn Met Gly Glu Glu Val Ile Ile Gly Ile Val Asp Ser
    130                 135                 140

Gly Val Trp Pro Glu Ser Glu Val Phe Asn Asp Asn Gly Ile Gly Pro
145                 150                 155                 160

Val Pro Ser His Trp Lys Gly Gly Cys Val Ser Gly Glu Asn Phe Thr
                165                 170                 175

Ser Ser Gln Cys Asn Lys Lys Leu Ile Gly Ala Lys Tyr Phe Ile Asn
            180                 185                 190

Gly Phe Leu Ala Thr His Glu Ser Phe Asn Ser Thr Glu Ser Leu Asp
        195                 200                 205

Phe Ile Ser Pro Arg Asp Arg Ser Gly His Gly Thr His Val Ala Thr
    210                 215                 220

Ile Ala Gly Gly Ser Tyr Val Pro Ser Ile Ser Tyr Lys Gly Leu Ala
225                 230                 235                 240

Gly Gly Thr Val Arg Gly Gly Ala Pro Arg Ala Arg Ile Ala Met Tyr
                245                 250                 255

Lys Ala Cys Trp Tyr Leu Asp Arg Phe Asp Ile Asn Thr Cys Ser Ser
            260                 265                 270

Ala Asp Ile Leu Lys Ala Met Asp Glu Ala Met His Asp Gly Val Asp
        275                 280                 285

Val Leu Ser Leu Ser Ile Gly Tyr Arg Phe Pro Tyr Phe Pro Glu Thr
    290                 295                 300

Asp Val Arg Ala Val Ile Ala Thr Gly Ala Phe His Ala Val Leu Lys
305                 310                 315                 320

Gly Ile Thr Val Val Cys Ser Gly Gly Asn Ser Gly Pro Ala Ala Gln
                325                 330                 335

Thr Val Gly Asn Thr Ala Pro Trp Ile Leu Thr Val Ala Ala Thr Thr
            340                 345                 350

Leu Asp Arg Ser Phe Pro Thr Pro Ile Thr Leu Gly Asn Asn Lys Leu
        355                 360                 365

Ile Leu Gly Gln Ala Met Tyr Thr Gly Pro Glu Leu Gly Phe Thr Ser
    370                 375                 380

Leu Val Tyr Pro Glu Asn Pro Gly Asn Ser Asn Glu Ser Phe Ser Gly
385                 390                 395                 400

Asp Cys Glu Leu Leu Phe Phe Asn Ser Asn His Thr Met Ala Gly Lys
                405                 410                 415

Val Val Leu Cys Phe Thr Thr Ser Thr Arg Tyr Ile Thr Val Ser Ser
            420                 425                 430

Ala Val Ser Tyr Val Lys Glu Ala Gly Gly Leu Gly Val Ile Val Ala
        435                 440                 445

Arg Asn Pro Gly Asp Asn Leu Ser Pro Cys Glu Asp Asp Phe Pro Cys
```

-continued

```
    450                 455                 460

Val Ala Val Asp Tyr Glu Leu Gly Thr Asp Ile Leu Leu Tyr Ile Arg
465                 470                 475                 480

Ser Thr Gly Leu Pro Val Val Lys Ile Gln Pro Ser Lys Thr Leu Val
                485                 490                 495

Gly Gln Pro Val Gly Thr Lys Val Ala Asp Phe Ser Ser Arg Gly Pro
            500                 505                 510

Asn Ser Ile Glu Pro Ala Ile Leu Lys Pro Asp Ile Ala Ala Pro Gly
        515                 520                 525

Val Ser Ile Leu Ala Ala Thr Thr Thr Asn Lys Thr Phe Asn Asp Arg
    530                 535                 540

Gly Phe Ile Phe Leu Ser Gly Thr Ser Met Ala Ala Pro Thr Ile Ser
545                 550                 555                 560

Gly Val Val Ala Leu Leu Lys Ala Leu His Arg Asp Trp Ser Pro Ala
                565                 570                 575

Ala Ile Arg Ser Ala Ile Val Thr Thr Ala Trp Arg Thr Asp Pro Phe
            580                 585                 590

Gly Glu Gln Ile Phe Ala Glu Gly Ser Pro Arg Lys Leu Ala Asp Pro
        595                 600                 605

Phe Asp Tyr Gly Gly Gly Leu Val Asn Pro Glu Lys Ala Ala Lys Pro
    610                 615                 620

Gly Leu Val Tyr Asp Leu Gly Leu Glu Asp Tyr Val Leu Tyr Met Cys
625                 630                 635                 640

Ser Val Gly Tyr Asn Glu Thr Ser Ile Ser Gln Leu Val Gly Lys Gly
                645                 650                 655

Thr Val Cys Ser Asn Pro Lys Pro Ser Val Leu Asp Phe Asn Leu Pro
            660                 665                 670

Ser Ile Thr Ile Pro Asn Leu Lys Asp Glu Val Thr Leu Thr Arg Thr
        675                 680                 685

Leu Thr Asn Val Gly Gln Leu Glu Ser Val Tyr Lys Val Val Ile Glu
    690                 695                 700

Pro Pro Ile Gly Ile Gln Val Thr Val Thr Pro Glu Thr Leu Leu Phe
705                 710                 715                 720

Asn Ser Thr Thr Lys Arg Val Ser Phe Lys Val Lys Val Ser Thr Thr
                725                 730                 735

His Lys Ile Asn Thr Gly Tyr Phe Phe Gly Ser Leu Thr Trp Ser Asp
            740                 745                 750

Ser Leu His Asn Val Thr Ile Pro Leu Ser Val Arg Thr Gln Ile Leu
        755                 760                 765

Gln Asn Tyr Tyr Asp Glu Asn
    770                 775
```

<210> SEQ ID NO 33
<211> LENGTH: 1140
<212> TYPE: DNA
<213> ORGANISM: Arabidopsis thaliana

<400> SEQUENCE: 33

```
atggaatatg gagaagaacc ctcgattaaa agatttctaa tgcttcctga tgatttggta      60

tttaactgct tagctcgcgt ctcaagatta cattatccaa ctctctcatt agtctccaaa     120

aaatttcgct ttcttcttgc ttcaaaggag ctttaccaaa cccgaatcct cttaggcgga     180

acggagagtt gtctttacgt gtgcgtacga ctccataccg attctgaaca actacattgg     240

ttcattatct accagggacc aaatagctcc aaaaaagttt tggtcccgat ttcatctccc     300
```

```
aattttactt ccgcagccct gccgggtttt gtagtggtcg gtcatgagat atatgccatt    360

ggcggtggat cagagaataa aaacgcttcg ataaatgcaa ctggatcaaa gacttataac    420

gctttgtcta gcgttatggt tatggactct cgttctcaca catggcgtga agctccaagc    480

atgcgggtgg cccgtgtgtt tccatctgct tgtaccctcg atgggagaat atatgttacg    540

ggaggctgcg aaaatctcaa ttcaatgaat tggatggaga tttttgatac gaagactcaa    600

acttgggagt tttacagat ccctagcgag gaggtatgca aaggctctga gtacttaagc     660

ataagttatc aaagaaccgt ctatgtaggg tctagggaaa aagatgtcac ttacaagatg    720

cataaaggta aatggagagg ggcagacata tgcctgaatc atggatggag tctggatcca    780

tcatcttgtt gtgtgataga gaacgtgttc taccgttgca gtcttgggga tgtacgttgg    840

tatgacctca agaaaagaga atgggcagct ttgaagggtt tggaaggact gcctactttt    900

actaattatt atagaaattt taaatcggcg gatcattgtg gaaaattggc gatttcttgg    960

gaggagtatg tgttagttga tgacgaaaca aagatttggt gtgcggaaat tgcgattcaa   1020

aaacgccaaa atggagaaat ttggggaacg cttgagtggt ttgacaatgt gtttatatcc   1080

agtggaccaa accgtcatgt ggatttatta gtgaatgctc ttactgcaac agtttggtga   1140
```

```
<210> SEQ ID NO 34
<211> LENGTH: 379
<212> TYPE: PRT
<213> ORGANISM: Arabidopsis thaliana

<400> SEQUENCE: 34

Met Glu Tyr Gly Glu Glu Pro Ser Ile Lys Arg Phe Leu Met Leu Pro
1               5                   10                  15

Asp Asp Leu Val Phe Asn Cys Leu Ala Arg Val Ser Arg Leu His Tyr
            20                  25                  30

Pro Thr Leu Ser Leu Val Ser Lys Lys Phe Arg Phe Leu Leu Ala Ser
        35                  40                  45

Lys Glu Leu Tyr Gln Thr Arg Ile Leu Leu Gly Gly Thr Glu Ser Cys
    50                  55                  60

Leu Tyr Val Cys Val Arg Leu His Thr Asp Ser Glu Gln Leu His Trp
65                  70                  75                  80

Phe Ile Ile Tyr Gln Gly Pro Asn Ser Ser Lys Lys Val Leu Val Pro
                85                  90                  95

Ile Ser Ser Pro Asn Phe Thr Ser Ala Ala Leu Pro Gly Phe Val Val
            100                 105                 110

Val Gly His Glu Ile Tyr Ala Ile Gly Gly Gly Ser Glu Asn Lys Asn
        115                 120                 125

Ala Ser Ile Asn Ala Thr Gly Ser Lys Thr Tyr Asn Ala Leu Ser Ser
    130                 135                 140

Val Met Val Met Asp Ser Arg Ser His Thr Trp Arg Glu Ala Pro Ser
145                 150                 155                 160

Met Arg Val Ala Arg Val Phe Pro Ser Ala Cys Thr Leu Asp Gly Arg
                165                 170                 175

Ile Tyr Val Thr Gly Gly Cys Glu Asn Leu Asn Ser Met Asn Trp Met
            180                 185                 190

Glu Ile Phe Asp Thr Lys Thr Gln Thr Trp Glu Phe Leu Gln Ile Pro
        195                 200                 205

Ser Glu Glu Val Cys Lys Gly Ser Glu Tyr Leu Ser Ile Ser Tyr Gln
    210                 215                 220
```

-continued

```
Arg Thr Val Tyr Val Gly Ser Arg Glu Lys Asp Val Thr Tyr Lys Met
225                 230                 235                 240

His Lys Gly Lys Trp Arg Gly Ala Asp Ile Cys Leu Asn His Gly Trp
                245                 250                 255

Ser Leu Asp Pro Ser Ser Cys Cys Val Ile Glu Asn Val Phe Tyr Arg
            260                 265                 270

Cys Ser Leu Gly Asp Val Arg Trp Tyr Asp Leu Lys Lys Arg Glu Trp
        275                 280                 285

Ala Ala Leu Lys Gly Leu Glu Gly Leu Pro Thr Phe Thr Asn Tyr Tyr
    290                 295                 300

Arg Asn Phe Lys Ser Ala Asp His Cys Gly Lys Leu Ala Ile Ser Trp
305                 310                 315                 320

Glu Glu Tyr Val Leu Val Asp Asp Glu Thr Lys Ile Trp Cys Ala Glu
                325                 330                 335

Ile Ala Ile Gln Lys Arg Gln Asn Gly Glu Ile Trp Gly Thr Leu Glu
            340                 345                 350

Trp Phe Asp Asn Val Phe Ile Ser Ser Gly Pro Asn Arg His Val Asp
        355                 360                 365

Leu Leu Val Asn Ala Leu Thr Ala Thr Val Trp
    370                 375
```